(12) United States Patent  
Haruta

(10) Patent No.: US 10,792,253 B2  
(45) Date of Patent: Oct. 6, 2020

(54) PHARMACEUTICAL COMPOSITIONS

(71) Applicant: Shin Nippon Biomedical Laboratories, Ltd., Kagoshima-shi (JP)

(72) Inventor: Shunji Haruta, Kagoshima (JP)

(73) Assignee: Shin Nippon Biomedical Laboratories, Ltd., Kagoshima (JP)

(*) Notice: Subject to any disclaimer, the term of this patent is extended or adjusted under 35 U.S.C. 154(b) by 0 days.

(21) Appl. No.: 15/668,871

(22) Filed: Aug. 4, 2017

(65) Prior Publication Data

US 2018/0036247 A1 Feb. 8, 2018

Related U.S. Application Data

(60) Provisional application No. 62/371,298, filed on Aug. 5, 2016.

(51) Int. Cl.
| | | |
|---|---|---|
| *A61K 9/14* | (2006.01) | |
| *A61K 9/16* | (2006.01) | |
| *A61K 31/517* | (2006.01) | |
| *A61K 31/48* | (2006.01) | |
| *A61K 31/515* | (2006.01) | |
| *A61K 9/00* | (2006.01) | |
| *A61K 9/19* | (2006.01) | |
| *A61K 31/405* | (2006.01) | |
| *A61K 31/4985* | (2006.01) | |
| *A61K 31/568* | (2006.01) | |

(52) U.S. Cl.
CPC .......... *A61K 9/1652* (2013.01); *A61K 9/0043* (2013.01); *A61K 9/146* (2013.01); *A61K 9/1623* (2013.01); *A61K 9/1694* (2013.01); *A61K 9/19* (2013.01); *A61K 31/405* (2013.01); *A61K 31/48* (2013.01); *A61K 31/4985* (2013.01); *A61K 31/515* (2013.01); *A61K 31/517* (2013.01); *A61K 31/568* (2013.01); *C07B 2200/13* (2013.01)

(58) Field of Classification Search
CPC .... A61K 9/1676; A61K 31/405; A61K 31/48; A61K 31/4985; A61K 31/515
See application file for complete search history.

(56) References Cited

U.S. PATENT DOCUMENTS

| 5,169,849 A | 12/1992 | Kiechel et al. |
| 6,291,445 B1 * | 9/2001 | Nilsson ............... A61K 9/0043 514/174 |
| 6,835,389 B1 * | 12/2004 | Dohi .................... A61K 9/146 424/434 |

(Continued)

FOREIGN PATENT DOCUMENTS

| WO | WO-2004075824 A2 | 9/2004 |
| WO | WO-2004075824 A3 | 10/2004 |

(Continued)

OTHER PUBLICATIONS

Berge, et al. Pharmaceutical Salts, J Pharm Sci. Jan. 1977;66(1):1-19.

(Continued)

*Primary Examiner* — Lakshmi S Channavajjala  
(74) *Attorney, Agent, or Firm* — Wilson Sonsini Goodrich & Rosati, P.C.

(57) ABSTRACT

Disclosed herein are pharmaceutical powder compositions, methods of making such compositions, and uses thereof.

20 Claims, 8 Drawing Sheets

(56) References Cited

U.S. PATENT DOCUMENTS

| | | | |
|---|---|---|---|
| 2006/0147388 A1* | 7/2006 | Merkus | A61K 9/0043 |
| | | | 424/46 |
| 2010/0291221 A1* | 11/2010 | Cook | A61K 9/008 |
| | | | 424/489 |
| 2011/0045088 A1 | 2/2011 | Tsutsui et al. | |
| 2016/0228433 A1 | 8/2016 | Haruta et al. | |

FOREIGN PATENT DOCUMENTS

| WO | WO-2012105236 A1 | 8/2012 |
|---|---|---|
| WO | WO-2018025089 A2 | 2/2018 |
| WO | WO-2018025089 A3 | 3/2018 |

OTHER PUBLICATIONS

Kim, Budesonide/cyclodextrin complex-loaded lyophilized microparticles for intranasal application, Drug Development and Industrial Pharmacy, Apr. 3, 2013, 40(6):743-748.

PCT/IB2017/001121 International Search Report and Written Opinion dated Jan. 26, 2018.

Wiley, Evaluation of Drug Candidates for Preclinical Development: Pharmacokinetics, Metabolism. Pharmaceutics and Toxicology, 2010, p. 209.

\* cited by examiner i) Non-treated DHE ii) DHE/MCC Mixture Blended in a Bottle a) DHE/MCC Mixture Grinded in a Mortar b) DHE/MCC Mixture Spray-Dried with MCC c) DHE/MCC/HPMC Mixture Spray-Dried with MCC and HPMC d) DHE/HPMC Mixture Spray-Dried with HPMC e) DHE/PVP Mixture Spray-Dried with PVP

PHARMACEUTICAL COMPOSITIONS

CROSS-REFERENCE

The present application claims the benefit of U.S. Provisional Application Ser. No. 62/371,298, filed Aug. 5, 2016, which is incorporated herein by reference in its entirety.

INCORPORATION BY REFERENCE

All publications, patents, and patent applications disclosed herein are incorporated by reference to the same extent as if each individual publication, patent, or patent application was specifically and individually indicated to be incorporated by reference. In the event of a conflict between a term disclosed herein and a term in an incorporated reference, the term herein controls.

BRIEF SUMMARY

The inventive embodiments provided in this Brief Summary are meant to be illustrative only and to provide an overview of selective embodiments disclosed herein. The Brief Summary, being illustrative and selective, does not limit the scope of any claim, does not provide the entire scope of inventive embodiments disclosed or contemplated herein, and should not be construed as limiting or constraining the scope of this disclosure or any claimed inventive embodiment.

In some cases, the present disclosure provides for an intranasal pharmaceutical powder composition comprising particles that comprise an active agent and at least one member selected from the group consisting of a thickening agent, a carrier, a pH adjusting agent, a sugar alcohol, and any combination thereof, wherein: at least about 20 percent by weight of the active agent in the particles is amorphous as determined by X-ray diffraction; when the active agent has a crystalline form, a solubility of the active agent in a crystalline form in an aqueous liquid ranges from about 0.1 µg/mL to about 1 mg/mL in water at a temperature of 37±0.5° C.; the particles have an average particle size of about 10 microns to about 300 microns, as measured by laser diffraction; and when the intranasal pharmaceutical powder composition is administered, a pharmacokinetic parameter of the active agent improves by at least about 15%, compared to a corresponding composition that comprises the active agent in a crystalline form when intranasally administered, as measured by a same method. In some instances, the pharmaceutical powder composition comprises the active agent, the thickening agent, the carrier, and the sugar alcohol. In some instances, the pharmaceutical powder composition further comprises particles that comprise the active agent and are free from the thickening agent, the carrier, or a combination thereof. In some instances, the active agent is a non-peptide/non-protein drug. In some instances, the active agent is selected from the group consisting of an ergot alkaloid, 5-hydroxytryptaminel (5-HT1) receptor agonist, CGRP antagonist, NK-1 receptor antagonist, antihistamine, antiemetic agent, decongestant, opioid receptor agonist, antibiotic, antifungal agent, sulfa drug, antituberculosis drug, antimicrobial agent, antiviral agent, hypnotic sedative, antiepileptic agent, narcotic analgesic, nonnarcotic analgesic, sedative drug, psychotherapeutic agent, muscle relaxant, antiallergic agent, anti-rheumatic drug, cardiotonic drug, antiarrhythmic agent, antihypertensive agent, diuretic agent, coronary vasodilator, antidementia drug, brain activator, brain circulation ameliorating agent, antiparkinsonian agent, antihyperlipidemic drug, antiulcer drug, obesity drug, diabetic drug, hemostatic drug, antithrombotic agent, migraine drug, antitussive drug, expectorant, respiratory stimulant, asthma drug, antidiarrheal drug, nonsteroidal antiinflammatory agent, antipodagric, therapeutic agent for urinary disease, drug for improving sexual function, agent for the uterus, steroid, prostaglandin, vitamin, antidote, therapeutic agent for heavy metal toxification, quit smoking agent, antianaphylactic agent, antitumor agent, immunostimulator, immunosuppressive drug, and any combination thereof. In some instances, the active agent is selected from the group consisting of didanosine, zidovudine, lamivudine, acyatazanavir, nelfenavir, sanilvudine, emtricitabine, polyinosinic-polycytidylic acid, oseltamivir, zanamivir, valganciclovir, peramivir, laninamivir, favipiravir, amantadine, amphotericin B, miconazole, fluconazole, itraconazole, ketoconazole, ketamine, pentobarbital sodium, thiopental, amopentobarbital, hexobarbital, lidocaine, triazolam, zopiclone, zolpidem, eszopiclone, etizolam, clotiazepam, brotizolam, lormetazepam, estazolam, midazolam, nitrazepam, flunitrazepam, diazepam, chlordiazepoxide HCl, alprazolam, lorazepam, ethyl loflazepate, bromazepam, rilmazafone, chloral hydrate, carbamazepine, clonazepam, zonisamide, sodium valproate, phenytoin, phenobarbital, primidone, gabapentin, opium, morphine, ethylmorphine, oxycodone, hydrocodone, codeine, dihydrocodeine, fentanyl, remifentanil, droperidol, levorphanol, methadone, meperidine, pethidine, buprenorphine, butorphanol, tramadol, tapentadol, nalfurafine, pentazocine, nalbuphine hydrochloride, nalorphine, eptazocine, levallorphan, sulpyrine, aspirin, acetaminophen, ergotamine, dihydroergotamine (DHE), sumatriptan, eletriptan, zolmitriptan, rizatriptan, naratriptan, almotriptan, frovatriptan, avitriptan, lasmiditan, olcegepant, telcagepant, donepezil, suxamethonium, pancuronium, sildenafil, vardenafil, apomorphine, tadalafil, atropine, scopolamine, homatropine methylbromide, chlorpromazine, digitoxin, levomepromazine, thioridazine, acepromazine, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, progesterone, testosterone, dehydroepiandrosterone, estrogen, estradiol, levonorgestrel, protamine, leucovorin, dimercaprol, deferoxamine, sodium thiosulfate, mifepristone, risperidone, olanzapine, thalidomide, civamide, acyclovir, valacyclovir, famciclovir, penciclovir, lopinavir, ritonavir, saquinavir, vidarabine, idoxuridine, nifedipine, nimodipine, amiodarone, loratadine, tretinoin, carmustine, beraprost sodium, and any combination thereof. In some instances, the active agent is a peptide or a peptide-related compound, wherein the peptide or peptide-related compound has a molecular weight of 50,000 Daltons or less. In some instances, the active agent is selected from the group consisting of insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, FK-506, octreotide, carperitide, pramlintide, lanreotide, eptifibatide, albiglutide, pasireotide, teriparatide, exenatide, liraglutide, emfuvirtide, ziconotide, ecallantide, mifamurtide, nesiritide, peglinesatide, afamelanotide, linaclotide, lixisenatide, teduglutide, bentiromide, cureletide diethylamine, degarelix, ghrelin, atrial natriuretic peptide, a peptide analog thereof, and any combination thereof. In some instances, the active agent is a small molecule drug. In some instances, the active agent is an anti-migraine drug. In some instances, the active agent is an ergot alkaloid. In some instances, the active agent is DHE or a pharmaceutically acceptable salt thereof. In some instances, the active agent is DHE mesylate. In some instances, the active agent is indomethacin, midazolam, phenobarbital, or a pharmaceutically acceptable salt of any of the foregoing. In some instances, the active agent has an average particle size of about 5 microns or larger. In some instances, the particles have an average particle size of from about 15 to about 100 μm, or about 15-200 microns, as measured by laser diffraction. In some instances, the particles have an average particle size of from about 20 to about 50 μm, or about 50-150 microns, as measured by laser diffraction. In some instances, the particles are spray dried, freeze-dried, or melt-extruded. In some instances, the active agent is spray dried onto the carrier, the thickening agent, or a combination thereof. In some instances, the solubility is measured at a pH ranging from about 6.8 to about 7.4. In some instances, the particles comprise the carrier that is at least partially water insoluble at 37±0.5° C. In some instances, the water insolubility is measured at a pH ranging from about 6.8 to about 7.4. In some instances, the particles further comprise the thickening agent, and wherein the carrier has lower water solubility than that of the thickening agent. In some instances, the particles comprise the carrier that is at least partially adhesive to mucus. In some instances, the particles comprise the carrier that comprises a polysaccharide, an oligosaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, β cyclodextrin, or any combination thereof. In some instances, the particles comprise the carrier that has an average particle size of from about 5 to about 100 μm, as measured by laser diffraction. In some instances, the carrier has an average particle size of about 20 or about 23 μm, as measured by laser diffraction. In some instances, the particles comprise the thickening agent that is at least partially water soluble at 37±0.5° C. In some instances, the water solubility is measured at a pH ranging from about 6.8 to about 7.4. In some instances, the particles further comprise the carrier, and wherein the thickening agent has higher water solubility than that of the carrier. In some instances, the particles comprise the thickening agent that binds to the active agent. In some instances, the particles further comprise the carrier, and wherein the thickening agent binds to the active agent and the carrier. In some instances, the particles comprise the thickening agent that comprises a polysaccharide. In some instances, the thickening agent comprises hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 μm, about 15 to about 200 microns, as measured by laser diffraction. In some instances, the particles have an average particle size of about 15 μm, or about 50 to 150 microns, as measured by laser diffraction. In some instances, the particles comprise the thickening agent, the sugar alcohol, and the carrier and have an average particle size of from about 10 to about 50 μm, or about 15 to 200 microns, as measured by laser diffraction. In some instances, the particles have an average particle size of about 20 μm, or about 50 to 150 microns, as measured by laser diffraction. In some instances, the pharmaceutical powder composition further comprises a fluidizing agent. In some instances, the fluidizing agent comprises a calcium phosphate. In some instances, the calcium phosphate comprises tribasic calcium phosphate. In some instances, when the intranasal pharmaceutical powder composition is administered to the subject, a pharmacokinetic parameter of the active agent improves by at least about: 20%, 25%, 30%, 40%, 45%, 50%, 60%, 70%, 80%, 90%, 100%, 150%, 200%, 250%, 300%, 400%, or 500%, compared to a corresponding composition that comprises the active agent in a crystalline form when administered. In some instances, the improved pharmacokinetic parameter comprises a greater relative bioavailability from 0 min to 15 min ($rBA_{0-15min}$), a greater relative bioavailability from 0 min to 30 min ($rBA_{0-30min}$), a greater relative bioavailability from 0 min to 60 min ($rBA_{0-60min}$), or any combination thereof. In some instances, the improved pharmacokinetic parameter comprises an average $rBA_{0-15min}$, and the improvement is at least about 100%, e.g., at least about 115% or 150%. In some instances, the average $rBA_{0-15min}$ is about 150% to 1500% in serum of the subject. In some instances, the improved pharmacokinetic parameter comprises an average $rBA_{0-30min}$, and the improvement is at least about 80%, e.g., at least about 115%. In some instances, the improved pharmacokinetic parameter comprises an average $rBA_{0-60min}$, and the improvement is at least 100%, e.g., at least about 115%. In some instances, the improved pharmacokinetic parameter comprises a higher maximum blood concentration ($C_{max}$). In some instances, the improved pharmacokinetic parameter comprises a shorter time to reach maximum blood concentration ($T_{max}$). In some instances, the improved pharmacokinetic parameter comprises an increased area under the curve (AUC) for blood concentration-time profile. In some instances, the pharmaceutical powder composition further comprises an additional active agent. In some instances, the additional active agent comprises caffeine, which is amorphous, crystalline, at least 20% of amorphous by weight of the caffeine, or any combination thereof. In some instances, at least about: 25%, 30%, 40%, 45%, 50%, 55%, 60%, 65%, 70%, 75%, 80%, 85%, 90%, 95%, or 98% by weight of the active agent is amorphous. In some instances, the pharmaceutical powder composition retains at least about: 80%, 85%, 90%, or 95% by weight of the active agent in a closed container after a period of at least about: 30, 60, 120, 180, 360, 720, or 1080 days. In some instances, the container is kept at about 20° C. to about 40° C. at a standard atmosphere pressure with a relative humidity of about 50% to about 75%. In some instances, the container is kept at about 25° C. at a standard atmosphere pressure with a relative humidity of about 50%. In some instances, the crystalline form comprises a polymorph.

In some instances, the intranasal pharmaceutical powder composition comprises indomethacin or a pharmaceutically acceptable salt thereof, microcrystalline cellulose, and mannitol. In some instances, the intranasal pharmaceutical powder composition comprises indomethacin or a pharmaceutically acceptable salt thereof, microcrystalline cellulose, and tribasic calcium phosphate. In some instances, the indomethacin or a pharmaceutically acceptable salt thereof is in a freeze-dried form, amorphous, or a combination thereof. In some instances, the microcrystalline cellulose comprises a first microcrystalline cellulose that has an average particle size of about 20-23 µm and a second microcrystalline cellulose has an average particle size of about 50 µm. In some instances, the pharmaceutical powder composition comprises: indomethacin or a pharmaceutically acceptable salt thereof, e.g., freeze-dried and/or amorphous, which is present in about 1-15% of a total weight of the pharmaceutical powder composition; a first microcrystalline cellulose that is present in about 70-95% of the total weight of the pharmaceutical powder composition, wherein the first microcrystalline cellulose has an average particle size of about 20-23 µm; a second microcrystalline cellulose that is present in about 1-20% of the total weight of the pharmaceutical powder composition, wherein the second microcrystalline cellulose has an average particle size of about 50 µm; and tribasic calcium phosphate that is present in about 0.5-5% of the total weight of the pharmaceutical powder composition. In some instances, the pharmaceutical powder composition comprises: indomethacin or a pharmaceutically acceptable salt thereof, e.g., freeze-dried and/or amorphous, which is present in about 5% of a total weight of the pharmaceutical powder composition; a first microcrystalline cellulose that is present in about 84% of the total weight of the pharmaceutical powder composition, wherein the first microcrystalline cellulose has an average particle size of about 20-23 µm; a second microcrystalline cellulose that is present in about 10% of the total weight of the pharmaceutical powder composition, wherein the second microcrystalline cellulose has an average particle size of about 50 µm; and tribasic calcium phosphate that is present in about 1% of the total weight of the pharmaceutical powder composition. In some instances, the pharmaceutical powder composition comprises: about 0.5-5 mg of indomethacin or a pharmaceutically acceptable salt thereof, e.g., freeze-dried and/or amorphous; about 10-18 mg of microcrystalline cellulose that has an average particle size of about 20-23 µm; about 1-10 mg of microcrystalline cellulose that has an average particle size of about 50 µm; and about 0.1-2 mg of tribasic calcium phosphate. In some instances, the pharmaceutical powder composition comprises: about 1 mg of indomethacin or a pharmaceutically acceptable salt thereof, e.g., freeze-dried and/or amorphous; about 16.8 mg of microcrystalline cellulose that has an average particle size of about 20-23 µm; about 2 mg of microcrystalline cellulose that has an average particle size of about 50 µm; and about 0.2 mg of tribasic calcium phosphate.

In some instances, the intranasal pharmaceutical powder composition comprises testosterone or a pharmaceutically acceptable salt thereof, microcrystalline cellulose, and mannitol. In some instances, the intranasal pharmaceutical powder composition comprises testosterone or a pharmaceutically acceptable salt thereof, microcrystalline cellulose, and tribasic calcium phosphate. In some instances, the indomethacin or a pharmaceutically acceptable salt thereof is a freeze-dried form, amorphous, or a combination thereof. In some instances, the microcrystalline cellulose comprises a first microcrystalline cellulose that has an average particle size of about 20-23 µm and a second microcrystalline cellulose has an average particle size of about 50 µm. In some instances, wherein the pharmaceutical powder composition comprises: testosterone or a pharmaceutically acceptable salt thereof, e.g., freeze-dried and/or amorphous, which is present in about 1-20% of a total weight of the pharmaceutical powder composition; a first microcrystalline cellulose that is present in about 70-95% of the total weight of the pharmaceutical powder composition, wherein the first microcrystalline cellulose has an average particle size of about 20-23 µm; a second microcrystalline cellulose that is present in about 1-20% of the total weight of the pharmaceutical powder composition, wherein the second microcrystalline cellulose has an average particle size of about 50 µm; and tribasic calcium phosphate that is present in about 0.5-5% of the total weight of the pharmaceutical powder composition. In some instances, the pharmaceutical powder composition comprises: testosterone or a pharmaceutically acceptable salt thereof, e.g., freeze-dried and/or amorphous, which is present in about 10% of a total weight of the pharmaceutical powder composition; a first microcrystalline cellulose that is present in about 79% of the total weight of the pharmaceutical powder composition, wherein the first microcrystalline cellulose has an average particle size of about 20-23 µm; a second microcrystalline cellulose that is present in about 10% of the total weight of the pharmaceutical powder composition, wherein the second microcrystalline cellulose has an average particle size of about 50 µm; and tribasic calcium phosphate that is present in about 1% of the total weight of the pharmaceutical powder composition. In some instances, the pharmaceutical powder composition comprises: about 1-10 mg of testosterone or a pharmaceutically acceptable salt thereof, e.g., freeze-dried and/or amorphous; about 10-18 mg of microcrystalline cellulose that has an average particle size of about 20-23 µm; about 1-10 mg of microcrystalline cellulose that has an average particle size of about 50 µm; and about 0.1-2 mg of tribasic calcium phosphate. In some instances, wherein the pharmaceutical powder composition comprises: about 2 mg of testosterone or a pharmaceutically acceptable salt thereof, e.g., freeze-dried and/or amorphous; about 15.8 mg of microcrystalline cellulose that has an average particle size of about 20-23 µm; about 2 mg of microcrystalline cellulose that has an average particle size of about 50 µm; and about 0.2 mg of tribasic calcium phosphate.

In some cases, the present disclosure provides for a method, comprising intranasally administering to a subject a pharmaceutical powder composition comprising particles that comprise an active agent and at least one member selected from the group consisting of a thickening agent, a carrier, a pH adjusting agent, a sugar alcohol, and any combination thereof, wherein at least about 20 percent by weight of the active agent in the particles is amorphous as determined by X-ray diffraction; when the active agent has a crystalline form, a solubility of the active agent in a crystalline form ranges from about 0.1 µg/mL to about 1 mg/mL in water at a temperature of 37±0.5° C. at a pH ranging from about 6.8 to about 7.4; the particles have an average particle size of about 10 microns to about 300 microns, as measured by laser diffraction; and the intranasal administration of the pharmaceutical powder composition improves a pharmacokinetic parameter of the active agent by at least about 15%, when compared to an intranasal administration of a corresponding composition that comprises the active agent in a crystalline form, as measured by a same method. In some instances, the pharmaceutical powder composition comprises the active agent, the thickening agent, the carrier, and the sugar alcohol. In some instances, the pharmaceutical powder composition further comprises particles that comprise the active agent and are free from the thickening agent, the carrier, or a combination thereof. In some instances, the active agent is a non-peptide/non-protein drug. In some instances, the active agent is selected from the group consisting of ergot alkaloid, 5-hydroxytryptaminel (5-HT1) receptor agonist, CGRP antagonist, NK-1 receptor antagonist, antihistamine, antiemetic agent, decongestant, opioid receptor agonist, antibiotic, antifungal agent, sulfa drug, antituberculosis drug, antimicrobial agent, antiviral agent, hypnotic sedative, antiepileptic agent, narcotic analgesic, nonnarcotic analgesic, sedative drug, psychotherapeutic agent, muscle relaxant, antiallergic agent, anti-rheumatic drug, cardiotonic drug, antiarrhythmic agent, antihypertensive agent, diuretic agent, coronary vasodilator, antidementia drug, brain activator, brain circulation ameliorating agent, antiparkinsonian agent, antihyperlipidemic drug, antiulcer drug, obesity drug, diabetic drug, hemostatic drug, antithrombotic agent, migraine drug, antitussive drug, expectorant, respiratory stimulant, asthma drug, antidiarrheal drug, nonsteroidal antiinflammatory agent, antipodagric, therapeutic agent for urinary disease, drug for improving sexual function, agent for the uterus, steroid, prostaglandin, vitamin, antidote, therapeutic agent for heavy metal toxification, quit smoking agent, antianaphylactic agent, antitumor agent, immunostimulator, immunosuppressive drug, and any combination thereof. In some instances, the active agent is selected from the group consisting of didanosine, zidovudine, lamivudine, acyatazanavir, nelfenavir, sanilvudine, emtricitabine, polyinosinic-polycytidylic acid, oseltamivir, zanamivir, valganciclovir, peramivir, laninamivir, favipiravir, amantadine, amphotericin B, miconazole, fluconazole, itraconazole, ketoconazole, ketamine, pentobarbital sodium, thiopental, amopentobarbital, hexobarbital, lidocaine, triazolam, zopiclone, zolpidem, eszopiclone, etizolam, clotiazepam, brotizolam, lormetazepam, estazolam, midazolam, nitrazepam, flunitrazepam, diazepam, chlordiazepoxide HCl, alprazolam, lorazepam, ethyl loflazepate, bromazepam, rilmazafone, chloral hydrate, carbamazepine, clonazepam, zonisamide, sodium valproate, phenytoin, phenobarbital, primidone, gabapentin, opium, morphine, ethylmorphine, oxycodone, hydrocodone, codeine, dihydrocodeine, fentanyl, remifentanil, droperidol, levorphanol, methadone, meperidine, pethidine, buprenorphine, butorphanol, tramadol, tapentadol, nalfurafine, pentazocine, nalbuphine hydrochloride, nalorphine, eptazocine, levallorphan, sulpyrine, aspirin, acetaminophen, ergotamine, dihydroergotamine, sumatriptan, eletriptan, zolmitriptan, rizatriptan, naratriptan, almotriptan, frovatriptan, avitriptan, lasmiditan, olcegepant, telcagepant, donepezil, suxamethonium, pancuronium, sildenafil, vardenafil, apomorphine, tadalafil, atropine, scopolamine, homatropine methylbromide, chlorpromazine, digitoxin, levomepromazine, thioridazine, acepromazine, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, progesterone, testosterone, dehydroepiandrosterone, estrogen, estradiol, levonorgestrel, protamine, leucovorin, dimercaprol, deferoxamine, sodium thiosulfate, mifepristone, risperidone, olanzapine, thalidomide, civamide, acyclovir, valacyclovir, famciclovir, penciclovir, lopinavir, ritonavir, saquinavir, vidarabine, idoxuridine, nifedipine, nimodipine, amiodarone, loratadine, tretinoin, carmustin, beraprost sodium, and any combination thereof. In some instances, the active agent is a peptide or a peptide-related compound, wherein the peptide or peptide-related compound has a molecular weight of 50,000 Daltons or less. In some instances, the active agent is selected from the group consisting of insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, FK-506, octreotide, carperitide, pramlintide, lanreotide, eptifibatide, albiglutide, pasireotide, teriparatide, exenatide, liraglutide, emfuvirtide, ziconotide, ecallantide, mifamurtide, nesiritide, peglinesatide, afamelanotide, linaclotide, lixisenatide, teduglutide, bentiromide, cureletide diethylamine, degarelix, ghrelin, atrial natriuretic peptide, a peptide analog thereof, and any combination thereof. In some instances, the active agent is a small molecule drug. In some instances, the active agent is an anti-migraine drug. In some instances, the active agent is an ergot alkaloid. In some instances, the active agent is dihydroergotamine (DHE) or a pharmaceutically acceptable salt thereof. In some instances, the active agent is dihydroergotamine mesylate. In some instances, the active agent is indomethacin, midazolam, phenobarbital, or a pharmaceutically acceptable salt of any of the foregoing. In some instances, the active agent has an average particle size of about 5 microns or larger. In some instances, the particles have an average particle size of from about 15 to about 100 μm, or about 15-200 microns, as measured by laser diffraction. In some instances, the particles have an average particle size of from about 20 to about 50 μm, or about 50-150 microns, as measured by laser diffraction. In some instances, the particles are spray dried. In some instances, the active agent is spray dried onto the carrier, the thickening agent, or a combination thereof to form the particles. In some instances, the solubility is measured at a pH ranging from about 6.8 to about 7.4. In some instances, the particles comprise the carrier that is at least partially water insoluble at 37±0.5° C. In some instances, the water insolubility is measured at a pH ranging from about 6.8 to about 7.4. In some instances, the particles further comprise the thickening agent, and wherein the carrier has lower water solubility than that of the thickening agent. In some instances, the particles comprise the carrier that is at least partially adhesive to mucus. In some instances, the particles comprise the carrier that comprises an oligosaccharide, a polysaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, β cyclodextrin, or any combination thereof. In some instances, the particles comprise the carrier that has an average particle size of from about 10 to about 100 μm, as measured by laser diffraction. In some instances, the carrier has an average particle size of about 20 or 23 μm, as measured by laser diffraction. In some instances, the particles comprise the thickening agent that is at least partially water soluble at 37±0.5° C. In some instances, the water solubility is measured at a pH ranging from about 6.8 to about 7.4. In some instances, the particles further comprise the carrier, and wherein the thickening agent has higher water solubility than that of the carrier. In some instances, the particles comprise that the thickening agent binds to the active agent. In some instances, the particles further comprise the carrier, and wherein the thickening agent binds to the active agent and the carrier. In some instances, the particles comprise the thickening agent that comprises a polysaccharide. In some instances, the thickening agent comprises hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 µm, as measured by laser diffraction. In some instances, the particles have an average particle size of about 15 µm, or about 50-150 microns, as measured by laser diffraction. In some instances, the particles comprise the thickening agent, the sugar alcohol, and the carrier and have an average particle size of from about 10 to about 50 µm, or about 15-200 microns, as measured by laser diffraction. In some instances, the particles have an average particle size of about 20 µm, or about 50-150 microns, as measured by laser diffraction. In some instances, the pharmaceutical powder composition further comprises a fluidizing agent. In some instances, the fluidizing agent comprises a tribasic calcium phosphate. In some instances, the administration of the pharmaceutical powder composition improves the pharmacokinetic parameter of the active agent by at least about: 20%, 25%, 30%, 40%, 45%, 50%, 60%, 70%, 80%, 90%, 100%, 150%, 200%, 250%, 300%, 400%, or 500%, when compared to administration of the corresponding composition that comprises the active agent in the crystalline form. In some instances, the improved pharmacokinetic parameter comprises a greater relative bioavailability from 0 min to 15 min ($rBA_{0-15min}$), a greater relative bioavailability from 0 min to 30 min ($rBA_{0-30min}$), a greater relative bioavailability from 0 min to 60 min ($rBA_{0-60min}$), or any combination thereof. In some instances, the improved pharmacokinetic parameter comprises an average $rBA_{0-15min}$, and the improvement is at least about 100%, e.g., at least about: 115% or 150%. In some instances, the average $rBA_{0-15min}$ is about 150% to 1500% in serum of the subject. In some instances, the improved pharmacokinetic parameter comprises an average $rBA_{0-30\ min}$, and the improvement is at least about 80%, e.g., at least about 115%. In some instances, the improvement is about 400%. In some instances, the improved pharmacokinetic parameter comprises an average $rBA_{0-60min}$, and the improvement is at least 100%, e.g., at least about 115%. In some instances, the improvement is about 200%. In some instances, the improved pharmacokinetic parameter comprises a higher maximum blood concentration ($C_{max}$). In some instances, the improved pharmacokinetic parameter comprises a shorter time to reach maximum blood concentration ($T_{max}$). In some instances, the improved pharmacokinetic parameter comprises an increased area under the curve (AUC) for blood concentration-time profile. In some instances, the pharmaceutical powder composition further comprises an additional active agent. In some instances, the additional active agent comprises caffeine, which is amorphous, crystalline, at least 20% of amorphous by weight of the caffeine, or any combination thereof. In some instances, at least about: 25%, 30%, 40%, 45%, 50%, 55%, 60%, 65%, 70%, 75%, 80%, 85%, 90%, 95%, or 98% by weight of the active agent is amorphous. In some instances, the pharmaceutical powder composition retains at least about: 80%, 85%, 90%, or 95% by weight of the active agent in a closed container after a period of at least about: 30, 60, 120, 180, 360, 720, or 1080 days. In some instances, the container is kept at about 20° C. to about 40° C. at a standard atmosphere pressure with a relative humidity of about 50% to about 75%. In some instances, the container is kept at about 25° C. at a standard atmosphere pressure with a relative humidity of about 50%. In some instances, the crystalline form comprises a polymorph. In some instances, the method is used in the treatment of a disease or a condition in the human subject. In some instances, the disease or condition is a headache, amyotrophic lateral sclerosis, Parkinson's disease, stress, anxiety, nausea, emesis, aggression, pain, neuropathic pain, sleeplessness, insomnia, restless leg syndrome, depression, or any combination thereof. In some instances, the disease or condition is a headache. In some instances, the headache is a migraine headache, a cluster headache, a hemicrania continua headache, a chronic headache, a tension headache, a chronic tension headache, or any combination thereof. In some instances, the headache is a migraine headache. In some instances, the headache is a migraine headache with aura. In some instances, the headache is a migraine headache without aura. In some instances, the headache is moderate to severe. In some instances, the headache is acute. In some instances, the pharmaceutical powder composition is administered for at least one day, two days, three days, four days, five days, six days, one week, one month, or one year. In some instances, the administration of the pharmaceutical powder composition is 1, 2, 3, 4, 5, 6, 7, or 8 times daily. In some instances, the pharmaceutical powder composition is in a single unit dose. In some instances, the pharmaceutical powder composition is a unit dose of from about 5 mg to about 50 mg, e.g., about 20 mg. In some instances, a unit dosage of the pharmaceutical powder composition contains about 0.1 mg to about 10 mg of the active agent, e.g., about 4 mg. In some instances, the subject is a primate. In some instances, the subject is a human. In some instances, the subject is a monkey.

In some cases, the present disclosure provides for a method of making an intranasal pharmaceutical powder composition, comprising spray drying, freeze-drying, or melt-extruding an active agent with at least one member selected from the group consisting of a thickening agent, a carrier, a pH adjusting agent, a sugar alcohol, and any combination thereof, to produce particles, wherein: at least about 20 percent by weight of the active agent in the particles is amorphous as determined by X-ray diffraction; when the active agent has a crystalline form, a solubility of the active agent in a crystalline form in an aqueous liquid ranges from about 0.1 µg/mL to about 1 mg/mL in water at a temperature of 37±0.5° C.; and the particles have an average particle size of about 10 microns to about 300 microns, as measured by laser diffraction. In some instances, the particles comprise the active agent and the thickening agent. In some instances, the particles comprise the active agent and the carrier. In some instances, the particles comprise the active agent, the carrier, and the thickening agent. In some instances, the method further comprises blending the particles with an additional amount of the carrier. In some instances, the method further comprises blending the particles with an additional carrier, additional thickening agent, or any combination thereof. In some instances, the particles comprise the active agent and are free from the thickening agent, the carrier, or a combination thereof. In some instances, the solubility is measured at a pH ranging from about 6.8 to about 7.4. In some instances, the particles comprise the carrier that is at least partially water insoluble at 37±0.5° C. In some instances, the water insolubility is measured at a pH ranging from about 6.8 to about 7.4. In some instances, the particles further comprise the thickening agent, and wherein the carrier has lower water solubility than that of the thickening agent. In some instances, the particles comprise the carrier that is at least partially adhesive to mucus. In some instances, the particles comprise the carrier that comprises an oligosaccharide, a polysaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, β cyclodextrin, or any combination thereof. In some instances, the particles have an average particle size of from about 15 to about 100 μm, as measured by laser diffraction. In some instances, the carrier has an average particle size of about 20 to about 50 μm, as measured by laser diffraction. In some instances, the particles comprise the thickening agent that is at least partially water soluble 37±0.5° C. In some instances, the water solubility is measured at a pH ranging from about 6.8 to about 7.4. In some instances, the particles further comprise the carrier, and wherein the thickening agent has higher water solubility than that of the carrier. In some instances, the particles comprise the thickening agent that binds to the active agent. In some instances, the particles further comprise the carrier, and wherein the thickening agent binds to the active agent and the carrier. In some instances, the particles comprise thickening agent that comprises a polysaccharide. In some instances, the thickening agent comprises hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 μm, or about 15-200 microns, as measured by laser diffraction. In some instances, the particles have an average particle size of about 15 μm, or about 50-150 microns, as measured by laser diffraction. In some instances, the particles comprise the thickening agent, the sugar alcohol, and the carrier and have an average particle size of from about 10 to about 50 μm, as measured by laser diffraction. In some instances, the particles an average particle size of about 20 μm-100 μm, 20-50 μm, or about 50-150 microns, as measured by laser diffraction. In some instances, the active agent is spray dried, freeze-dried, or melt-extruded with the thickening agent. In some instances, the method further comprises using a fluid bed granulation, e.g., after mixing all the components.

In some cases, the present disclosure provides for a use of an intranasal pharmaceutical powder composition disclosed herein in the treatment of a disease or condition. In some instances, the disease or condition is a headache, amyotrophic lateral sclerosis (ALS), Parkinson's disease, stress/anxiety, nausea, emesis, aggression, pain, neuropathic pain, sleeplessness, insomnia, restless leg syndrome, or depression. In some instances, the disease or condition is a headache. In some instances, the headache is a migraine headache, a cluster headache, a hemicrania continua headache, a chronic headache, a tension headache, a chronic tension headache, or any combination thereof. In some instances, the headache is a migraine headache. In some instances, the headache is a migraine headache with aura. In some instances, the headache is a migraine headache without aura. In some instances, the headache is moderate to severe. In some instances, the headache is acute. In some instances, the pharmaceutical powder composition is administered for at least one day, two days, three days, four days, five days, six days, one week, one month, or one year. In some instances, the intranasal pharmaceutical powder composition is administered 1, 2, 3, 4, 5, 6, 7, or 8 times daily for the treatment. In some instances, the intranasal pharmaceutical powder composition is in a single unit dose, e.g., in an amount of about 5-50 mg or about 20 mg. In some instances, a unit dosage of the intranasal pharmaceutical powder composition contains about 0.1 mg to about 10 mg of the active agent, e.g., about 4 mg. In some instances, the subject is a primate. In some instances, the subject is a human. In some instances, the subject is a monkey.

In some cases, the present disclosure provides for a device that contains a pharmaceutical powder composition disclosed herein. In some instances, the device is for a single use.

In some cases, an active agent disclosed herein has an average particle size larger than 5 μm.

In some cases, an active agent disclosed herein is suspended in methanol before spray drying or freeze-drying.

In some cases, an active agent is present in an amount of about 1-30% (e.g., 1-10%) by weight based on a weight of the particles or a pharmaceutical powder composition, for example about: 20%, or 3%.

In some cases, particles comprise a thickening agent that is present in an amount of about 0.05-2% or about 0.05-10% by weight based on a weight of the particles or a pharmaceutical powder composition, for example about 0.3% or about 5%. In some instances, particles comprise a sugar alcohol that is present in an amount of about 20-95% by weight based on a weight of the particles or a pharmaceutical powder composition, for example about: 20%, 25%, 40%, 60%, 25%, 50%, 75%, or 90%. In some instances, particles comprise the pH adjusting agent that is present in an amount of about 1-40% by weight based on a weight of the particles or a pharmaceutical powder composition, for example about: 2.5%, 5%, 15%, or 25%.

In some cases, a particle or composition disclosed herein comprises a pH adjusting agent. In some instances, the pH adjusting agent is selected from the group consisting of ascorbic acid, sodium ascorbate, tartaric acid, sodium tartrate, potassium tartrate, calcium tartrate, lithium tartrate, citric acid, sodium citrate, potassium citrate, calcium citrate, lithium citrate, phosphoric acid, sodium dihydrogenphosphate, sodium monohydrogenphosphate, lithium phosphate, potassium phosphate, calcium phosphate, sodium carbonate, sodium hydrogencarbonate, lactic acid, sodium lactate, potassium lactate, calcium lactate, acetic acid, sodium acetate, potassium acetate, calcium acetate, propionic acid, sulphuric acid, sodium sulphate, potassium sulphate, boric acid, sodium borate, maleic acid, lithium maleate, sodium maleate, potassium maleate, calcium maleate, succinic acid, lithium succinate, sodium succinate, potassium succinate, calcium succinate, fumaric acid, glutamic acid, formic acid, malic acid, hydrochloric acid, nitric acid, sodium hydroxide, potassium hydroxide, triethanolamine, diisopropanolamine, ammonia solution, monoethanole amine, diethanoleamine, triethanoleamine meglumine, sodium citrate, sodium bicarbonate, potassium bicarbonate, and any combination thereof.

In some cases, a particle or composition disclosed herein comprises a sugar alcohol. In some instances, the sugar alcohol is selected from the group consisting of mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof.

In some cases, a pharmacokinetic parameter disclosed herein is determined with an analysis of a blood or plasma sample collected at one or more time points of about 2, 5, 10, 15, 20, 30, 45, 60, 120, or 180 minutes after intranasal administration. In some instances, the analysis comprises a measurement of a plasma concentration of DHE, 8'-hydroxy-DHE, or a combination thereof in the blood or plasma sample. In some instances, the analysis is conducted with liquid chromatography (LC), mass spectrometry (MS), or a combination thereof. In some instances, the analysis is conducted with a LC/MS/MS method.

In some instances, the pharmaceutical powder composition disclosed herein comprises dihydroergotamine or a pharmaceutically acceptable salt thereof, mannitol, and microcrystalline cellulose. In some instances, the pharmaceutical powder composition further comprises HPMC. In some cases, the present disclosure provides a pharmaceutical powder composition that comprises: 1) about 1-8 mg such as 4 mg of dihydroergotamine or a pharmaceutically acceptable salt thereof 2) about 5-15 mg such as 5 mg of mannitol; and 3) about 5-15 mg such as 11 mg of microcrystalline cellulose. In some instances, the pharmaceutical powder composition has an average particle size diameter of about 20 to about 100 microns. In some instances, the pharmaceutical powder composition is for intransal administration. In some cases, the present disclosures provides a pharmaceutical powder composition that comprises: 1) dihydroergotamine or a pharmaceutically acceptable salt thereof that is present in about 20% of a total weight of the pharmaceutical powder composition; optionally 2) HPMC that is present in about 5% of the total weight of the pharmaceutical powder composition; 3) mannitol that is present in about 25% of the total weight of the pharmaceutical powder composition; and 4) microcrystalline cellulose that is present in about 50% or 55% of the total weight of the pharmaceutical powder composition, and wherein the pharmaceutical powder composition have an average particle size diameter of about 50 to about 150 microns. In some instances, the pharmaceutical powder composition is for intransal administration. In some cases, the present disclosures provides a pharmaceutical powder composition that comprises: 1) about 4 mg of dihydroergotamine or a pharmaceutically acceptable salt thereof; 2) about 1 mg of HPMC; 3) about 5 mg of mannitol; and 4) about 10 mg of microcrystalline cellulose, and wherein the pharmaceutical powder composition have an average particle size diameter of about 50 to about 150 microns. In some instances, the pharmaceutical powder composition is for intransal administration.

In some cases, the present disclosure provides particles that comprise an active agent, a carrier, a sugar alcohol, or any combination thereof. In some instances, the particles further comprise a thickening agent. In some instances, the particles are substantially uniform. In some instances, at least about: 10%, 15%, 20%, 30%, 40%, 50%, 60%, 70%, 80%, 90%, or 95% by weight of the particles are agglomerated, aggregated, or a combination thereof. In some instances, about: 10%-15%, 20%-30%, 40%-50%, 60%-70%, 80%-90%, 95%-99%, 10%-25%, 20%-40%, 40%-60%, 60%-80%, 80%-95%, 10%-30%, 10%-40%, 10%-50%, 30%-70%, 50%-90%, or 70%-99% by weight of the particles are agglomerated, aggregated, or a combination thereof. In some instances, the particles are substantially agglomerated, aggregated, or a combination thereof. In some instances, the active agent is aggregated or agglomerated, with the carrier, the sugar alcohol, or a combination thereof. In some instances, the sugar alcohol is aggregated or agglomerated, with the carrier. In some instances, the active agent is DHE or a pharmaceutically acceptable salt thereof. In some instances, the thickening agent is HPMC. In some instances, the carrier is microcrystalline cellulose. In some instances, the sugar alcohol is mannitol. In some instances, an average diameter of the particles is about 15 microns to about 200 microns, for example about 50 microns to about 150 microns, or about 20 microns to about 50 microns.

In some instances, the intranasal pharmaceutical powder composition disclosed herein comprises particles that have one or more following features: at least some of the particles disclosed herein substantially contain a single ingredient selected from the group consisting of an active agent, a thickening agent, a carrier, a pH adjusting agent, and a sugar alcohol; or at least some of the particles contain a single ingredient selected from the group consisting of the active agent, the thickening agent, the carrier, the pH adjusting agent, and the sugar alcohol; or at least some of the particles contain at least two ingredients selected from the group consisting of the active agent, the thickening agent, the carrier, the pH adjusting agent, and the sugar alcohol; or the intranasal pharmaceutical powder composition further comprises particles that comprise the active agent and are free from the thickening agent, the carrier, or a combination thereof; or at least some of the particles are aggregates; or at least some of the particles are agglomerates; or any combination thereof. In some cases, the present disclosure provides agglomerated particles that comprise an active agent, a thickening agent, a carrier, and a sugar alcohol. In some instances, the active agent is DHE or a pharmaceutically acceptable salt thereof. In some instances, the thickening agent is HPMC. In some instances, the carrier is microcrystalline cellulose. In some instances, the sugar alcohol is mannitol. In some instances, an average diameter of the agglomerated particles is about 15 microns to about 200 microns. In some instances, the average diameter of the agglomerated particles is about 50 microns to about 150 microns.

Additional aspects and advantages of the present disclosure will become readily apparent to those skilled in this art from the following detailed description, wherein only illustrative embodiments of the present disclosure are shown and described. As will be realized, the present disclosure is capable of other and different instances, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative instances, in which the principles of the invention are utilized, and the accompanying drawings (also "figure" and "FIG." herein), of which:

DETAILED DESCRIPTION

Figure 1A:
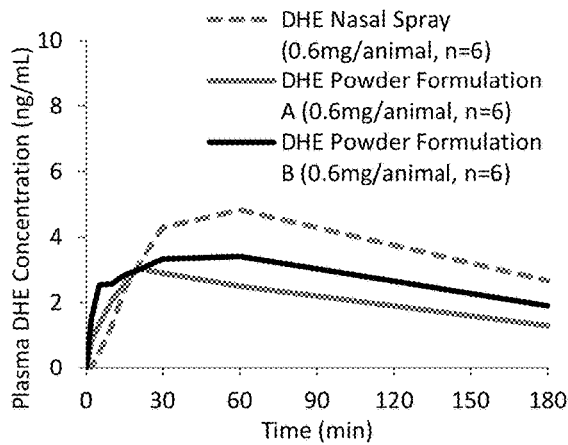
FIGS. 1A to 1F are a group of line graphs comparing DHE pharmacokinetic profiles in monkeys from testing various DHE formulations, for 0-180 min.
Figure 1B:
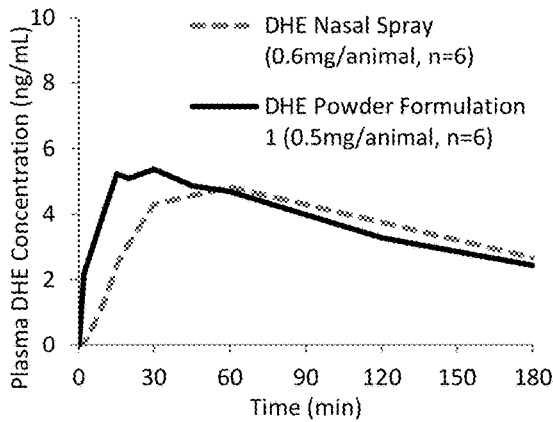
Figure 1C:
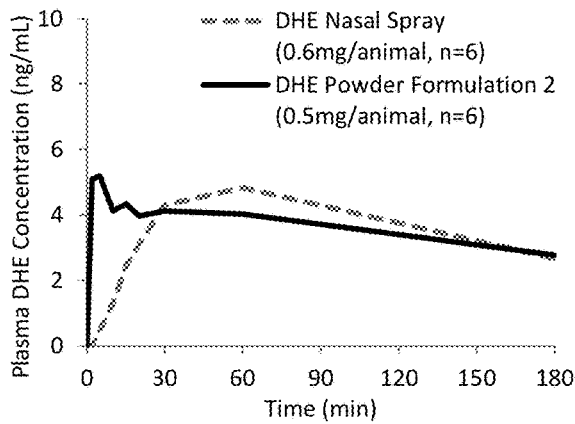
Figure 1D:
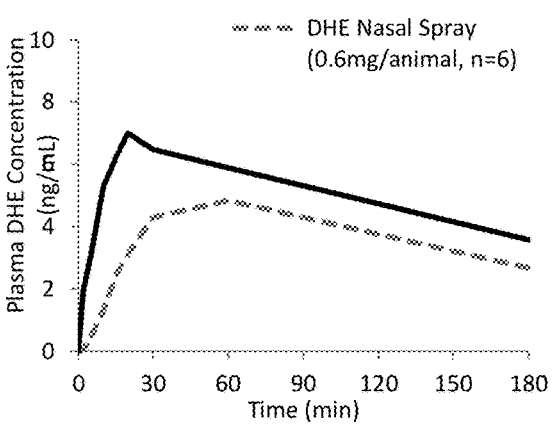
Figure 1E:
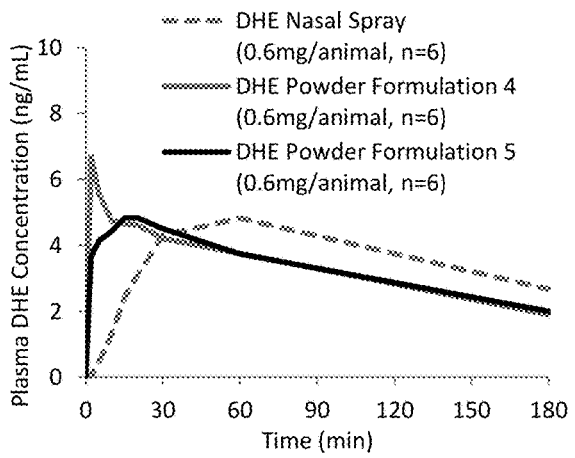
Figure 1F:
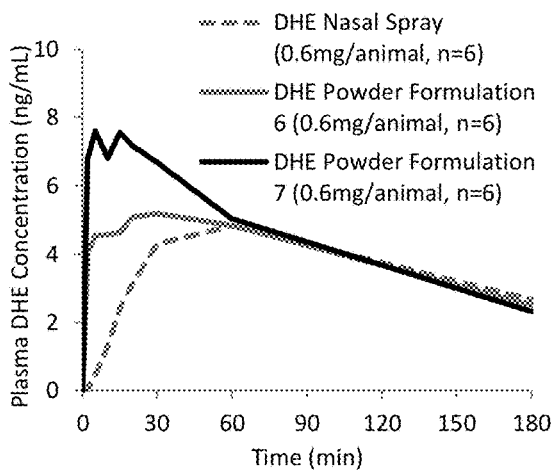
Figure 2A:
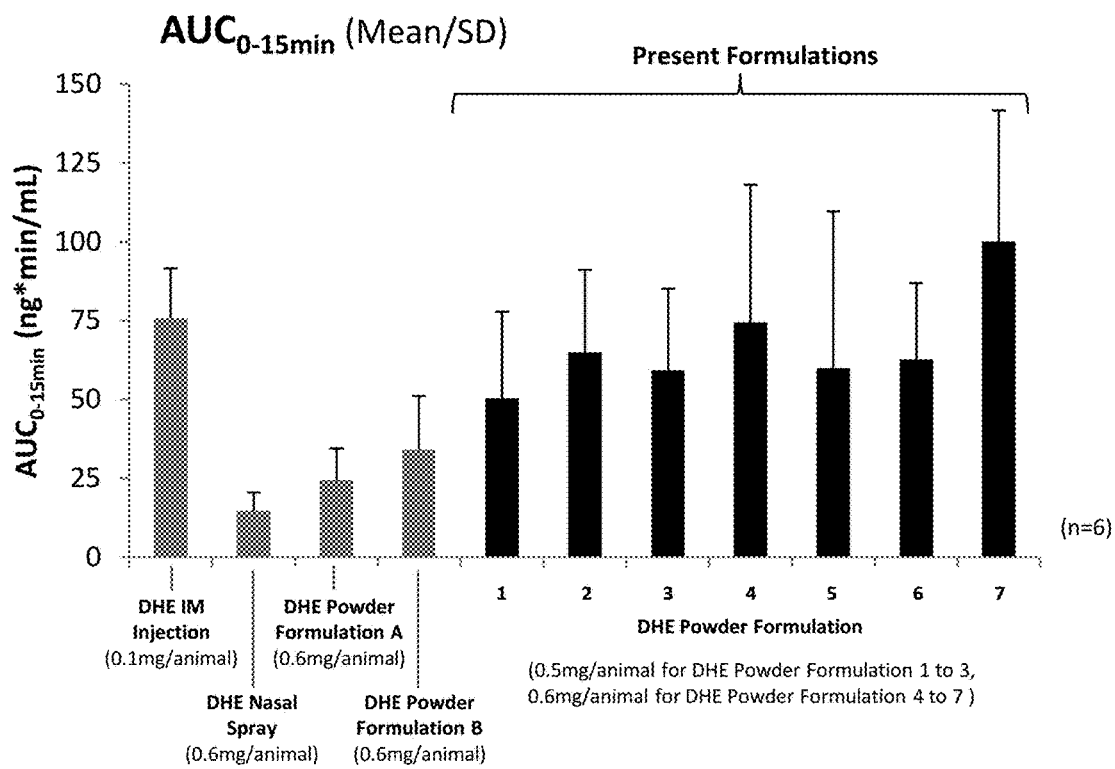
FIGS. 2A and 2B are a group of bar graphs comparing AUC profiles of various DHE formulations, tested in monkeys.
Figure 2B:
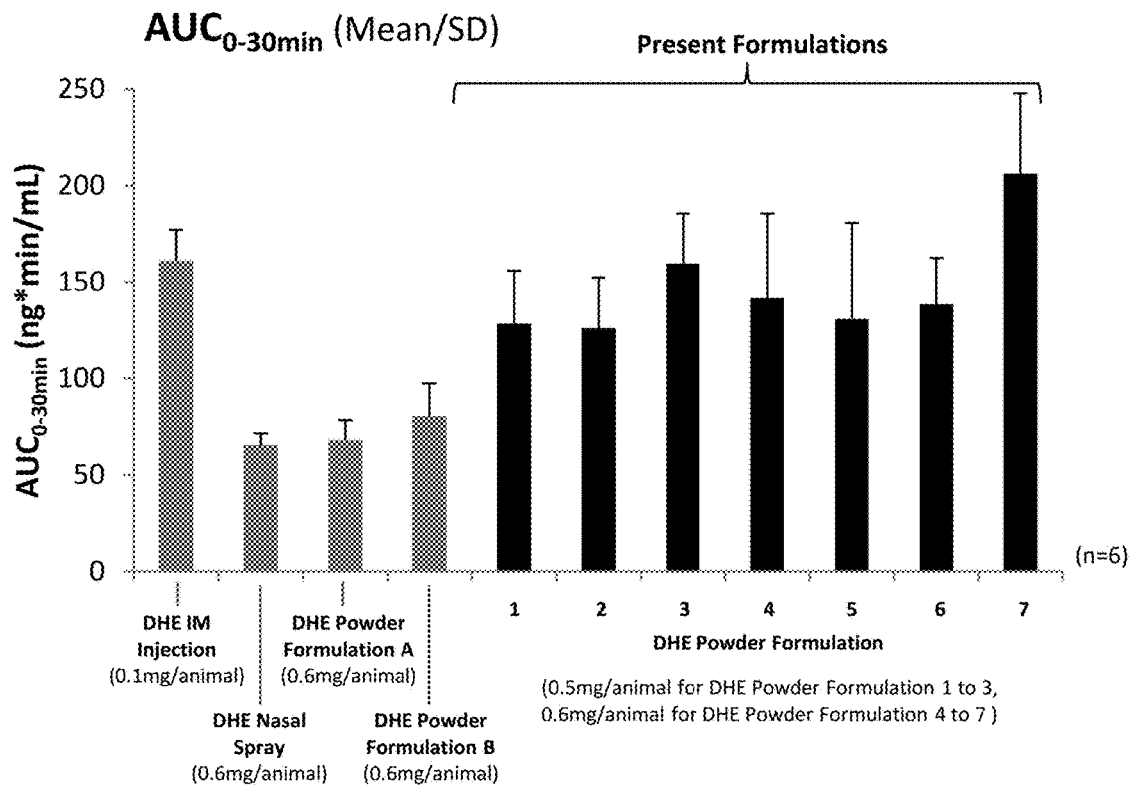

Unless defined otherwise, all technical and scientific terms used herein have the same meaning as commonly understood by one of the ordinary skill in the art to which this invention belongs. Although any methods and materials similar or equivalent to those described herein can be used in the practice or testing of the compositions or unit doses herein, some methods and materials are now described. Unless mentioned otherwise, the techniques employed or contemplated herein are standard methodologies. The materials, methods and examples are illustrative only and not limiting.

The details of one or more inventive instances are set forth in the accompanying drawings, the claims, and the description herein. Other features, objects, and advantages of the inventive instances disclosed and contemplated herein can be combined with any other instance unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some instances herein contemplate numerical ranges. When a numerical range is provided, unless otherwise indicated, the range includes the range endpoints. Unless otherwise indicated, numerical ranges include all values and subranges therein as if explicitly written out. Unless otherwise indicated, any numerical ranges and/or values herein can be at 80-125% of the numerical ranges and/or values.

A standard atmosphere (symbol: atm) is a unit of pressure defined as 101325 Pa (1.01325 bar), equivalent to 760 mmHg (torr), 29.92 inHg, or 14.696 psi.

In some instances, improvement is calculated as the following:

Improvement=$(|I-C|/C) \times D_f/D_c \times 100\%$

I=Improved value from a present composition
C=Control value from a comparator or conventional composition $D_f$=Dose of the present composition
$D_c$=Dose of the comparator or conventional composition Unless otherwise indicated, relative bioavailability (rBA) is equal to [(AUC of preparation with amorphous API/Dose of preparation with amorphous)/(AUC of preparation with 100% crystal/Dose of preparation of 100% crystal)×100%].

In some instances, a buffering agent is selected from the group consisting of sodium phosphate, sodium hydrogenphosphate, anhydrous sodium dihydrogenphosphate, crystalline sodium dihydrogenphosphate, disodium hydrogenphosphate, potassium phosphate, potassium dihydrogenphosphate, dipotassium phosphate, boric acid, borax, sodium acetate, citric acid, citric anhydride, sodium citrate, sodium glutamate, creatinine, and phosphate buffered saline.

Unless otherwise indicated, the term "thickening agent" refers to an excipient that increases a particle size of an active agent and/or viscosity of a composition. In some instances, a thickening agent disclosed herein binds to an active agent and/or a carrier via a non-covalent interaction, e.g., hydrogen bonding or van der Waals force.

Unless otherwise indicated, "average particle size" can refer to a particle size distribution of a powder in its non-aggregated state. In some instances, an average particle size refers to a mean particle size, for example calculated as a sum of size measurements of all measurable particles divided by a total number of particles measured. In some instances, an average particle size refers to a median particle size, for example indicating that about 50% of all measurable particles measured have a particle size less than the defined median particle size value, and that about 50% of all measurable particles measured have a particle size greater than the defined median particle size value. In some instances, an average particle size refers to a mode particle size, for example indicating the most frequently-occurring particle size value. In some instances, for spherical particles, an average particle size is a measurement of a particle's diameter. In some instances, for non-spherical particles, an average particle size is a measurement of longest or shortest diameters, perimeter, projected area, or by an equivalent spherical diameter. Primary particle diameter can be determined using a laser-diffraction particle size analyzer. In some instances, the particle size analyzer can be Mastersizer 2000 manufactured by Malvern Instruments Limited.

Pharmacokinetic data disclosed herein (e.g., $C_{max}$, $T_{max}$, $AUC_{0-t}$, $AUC_{0-180\ minutes}$, $AUC_{0-inf}$, $T_{1/2}$) can be measured from a primate, preferably a monkey, and preferably a Cynomolgus monkey, after a powder composition disclosed herein is administered. Alternatively, the pharmacokinetic data disclosed herein (e.g., $C_{max}$, $T_{max}$, $AUC_{0-t}$, $AUC_{0-180\ minutes}$, $AUC_{0-inf}$, $T_{1/2}$) can be measured from a human subject after a powder composition disclosed herein is administered. In some instances, an active agent such as dihydroergotamine, or a complex, chelate, salt, hydrate, polymorph, or ion pair thereof is administered at a rate such that a mean peak plasma concentration ($C_{max}$) of 8-hydroxy dihydroergotamine is higher than 10,000 pg/ml, and a mean time to $C_{max}$ ($T_{max}$) of 8-hydroxy dihydroergotamine is longer than 45 minutes.

Presented herein are compositions, comprising an active agent. In some instances, the active agent is in a free base form. In some instances, the active agent is in a pharmaceutically acceptable salt form. In some instances, the term "substantially" can mean 80-100% of a referred subject matter. In some instances, agglomerate can mean a loose accumulation of separate particles bonded by weak physical forces. In some instances, aggregate can mean a dense cluster of separate particles bonded by strong chemical or sinter forces.

Intranasal administration, as used herein in the context of the powder compositions presented herein, unless otherwise noted, refers to administration whereby at least 95±5% of the powder composition is administered to the nasal cavity as measured by multiple path particle dosimetry (MPPD) model analysis, a computational model used to estimate human airway particle dosimetry (see, e.g., Anjilvel, S. and Asgharian, B. (1995) Fundam. Appl. Toxicol. 28, 41-50; and National Institute for Public Health and the Environment (RIVM) (2002) Multiple Path Particle Dosimetry Model (MPPD v 1.0): A Model for Human and Rat Airway Particle Dosimetry. Bilthoven, The Netherlands. RIVA Report 650010030), or via an Andersen Cascade Impactor.

In some instances, not less than 90% of the particles in the powder compositions presented herein have a diameter less than 150 μm, and not more than 5% of the particles in the powder compositions have a diameter less than 10 μm. In some instances, the overall average particle size of the particles in the powder compositions presented herein is about 15 to about 30 μm, about 18 to about 25 μm, about 18 to about 20 μm, or about 20 μm.

In some instances, presented herein is a method of treating a disease or condition, e.g., pain, headache (e.g., migraine), hormone disorder, comprising intranasally administering to a human, a composition comprising an active agent, or a pharmaceutically acceptable salt thereof, microcrystalline cellulose, and tribasic calcium phosphate, wherein the composition is not a liquid solution or a liquid spray composition. Unless noted, such compositions are referred to herein as powder compositions. In some instances, a method disclosed herein comprises intranasally administering powder compositions comprising an active agent, microcrystalline cellulose with an average particle diameter size of about 100 μm or less, and tribasic calcium phosphate. Throughout, unless otherwise noted, "about" means within ±10% of a value. For example, if it is stated that a component makes up "about 70%" of a mixture, it is implied that the component makes up within a range of 63% and 77% of the mixture. In addition, in instances wherein "about" is used, it is to be understood that instances involving the exact value associated with "about" are also contemplated. For example, when an instance recites "about 0.5 milligram (mg) of an active agent," an instance reciting "0.5 mg of an active agent" is also contemplated and is described herein.

In some cases, provided herein are methods of treating a disease or condition, e.g., pain, headache (e.g., migraine), hormone disorder, comprising intranasally administering powder compositions comprising an active agent, a microcrystalline cellulose portion with an average particle size diameter of about 50-55 μm, e.g., 50 μm, comprising about 10% of the total weight of the powder composition, a microcrystalline cellulose portion with an average particle size of about 20 μm comprising about 3 to about 90%, e.g., 8 to about 90%, of the total weight of the powder composition and, optionally, a fluidizing agent. In some instances, the powder compositions utilized as part of the methods further comprise an active agent disclosed herein, e.g., caffeine, for example, anhydrous caffeine. Throughout, unless otherwise noted, percent (%) weight, in the context of the powder compositions presented herein, refers to weight per weight percent (%) (W/W %).

In some cases, presented herein are powder compositions that can be utilized in conjunction with the methods of treating a disease or condition, e.g., pain, headache (e.g., migraine), hormone disorder, wherein the powder compositions comprise an active agent or a pharmaceutically acceptable salt thereof. In some instances, provided herein are powder compositions comprising: a) an active agent b) microcrystalline cellulose, e.g., a microcrystalline cellulose with an average particle diameter size of about 100 μm or less; and c) tribasic calcium phosphate. In some instances, provided herein are powder compositions comprising an active agent, a microcrystalline cellulose portion with an average particle size diameter of about 50-55 μm, e.g., 50 μm, comprising about 10% of the total weight of the powder composition, a microcrystalline cellulose portion with an average particle size of about 20 μm comprising about 3% to about 90%, e.g., about 8 to about 90%, of the total weight of the powder composition and, optionally, a fluidizing agent. In some instances, the powder compositions further comprise an active agent disclosed herein, e.g. caffeine, for example, anhydrous caffeine. In some instances, greater than or equal to about 90% of the particles in the powder composition have a diameter less than 150 μm. In some instances, the overall average particle size of the composition is about 15 to about 30 μm, about 18 to about 25 μm, about 18 to about 20 μm, or about 20 μm. In some instances, less than or equal to about 5% of the particles in the powder composition have a diameter less than 10 μm. In some instances, greater than or equal to about 90% of the particles in the powder composition have a diameter less than 150 μm; and the overall average particle size of the composition is about 15 to about 30 μm, about 18 to about 25 μm, about 18 to about 20 μm, or about 20 μm; and less than or equal to about 5% of the particles in the powder composition have a diameter less than 10 μm.

In some cases, a powder composition disclosed herein comprises an active agent, microcrystalline cellulose, and tribasic calcium phosphate. In some instances, the microcrystalline cellulose comprises a first microcrystalline cellulose (e.g., average particle size of about 20 μm) and a second microcrystalline cellulose (e.g., average particle size of about 50 In).

In some cases, a powder composition disclosed herein has an angle of repose about 53° or less, for example, about 53°, 52°, 51°, 50°, 48°, 46°, 44°, 42°, 40°, 38°, 36°, 34°, 32°, 30°, 28°, 26°, 24°, 22°, 20° or less.

In some cases, presented herein are methods and compositions used for treating a disease or a condition, e.g., headache, pain, or hormone disorder. For example, the methods and compositions are used for treating migraine. In some instances, the methods of treating migraine are methods for the acute treatment of migraine headaches with or without aura. In some instances, at least a portion of the powder composition is administered to a single nostril of the human. In some instances, at least a portion of the powder composition is administered to each nostril of the human. For example, in some instances of the method, about half of the composition is administered to one nostril and about half of the composition is administered to the other nostril of the human.

In some cases, the present disclosure provides for a device that contains a pharmaceutical powder composition disclosed herein. In some instances, the device is for a single use.

Active Agents and Compositions

In some cases, an active agent disclosed herein is a non-peptide/non-protein drug. In some instances, the active agent is selected from the group consisting of ergot alkaloid, 5-hydroxytryptaminel (5-HT1) receptor agonist, CGRP antagonist, NK-1 receptor antagonist, antihistamine, antiemetic agent, decongestant, opioid receptor agonist, antibiotic, antifungal agent, sulfa drug, antituberculosis drug, antimicrobial agent, antiviral agent, hypnotic sedative, antiepileptic agent, narcotic analgesic, nonnarcotic analgesic, sedative drug, psychotherapeutic agent, muscle relaxant, antiallergic agent, anti-rheumatic drug, cardiotonic drug, antiarrhythmic agent, antihypertensive agent, diuretic agent, coronary vasodilator, antidementia drug, brain activator, brain circulation ameliorating agent, antiparkinsonian agent, antihyperlipidemic drug, antiulcer drug, obesity drug, diabetic drug, hemostatic drug, antithrombotic agent, migraine drug, antitussive drug, expectorant, respiratory stimulant, asthma drug, antidiarrheal drug, nonsteroidal antiinflammatory agent, antipodagric, therapeutic agent for urinary disease, drug for improving sexual function, agent for the uterus, steroid, prostaglandin, vitamin, antidote, therapeutic agent for heavy metal toxification, quit smoking agent, antianaphylactic agent, antitumor agent, immunostimulator, immunosuppressive drug, and any combination thereof. In some instances, the active agent is selected from the group consisting of didanosine, zidovudine, lamivudine, acyatazanavir, nelfenavir, sanilvudine, emtricitabine, polyinosinic-polycytidylic acid, oseltamivir, zanamivir, valganciclovir, peramivir, laninamivir, favipiravir, amantadine, amphotericin B, miconazole, fluconazole, itraconazole, ketoconazole, ketamine, pentobarbital sodium, thiopental, amopentobarbital, hexobarbital, lidocaine, triazolam, zopiclone, zolpidem, eszopiclone, etizolam, clotiazepam, brotizolam, lormetazepam, estazolam, midazolam, nitrazepam, flunitrazepam, diazepam, chlordiazepoxide HCl, alprazolam, lorazepam, ethyl loflazepate, bromazepam, rilmazafone, chloral hydrate, carbamazepine, clonazepam, zonisamide, sodium valproate, phenytoin, phenobarbital, primidone, gabapentin, opium, morphine, ethylmorphine, oxycodone, hydrocodone, codeine, dihydrocodeine, fentanyl, remifentanil, droperidol, levorphanol, methadone, meperidine, pethidine, buprenorphine, butorphanol, tramadol, tapentadol, nalfurafine, pentazocine, nalbuphine hydrochloride, nalorphine, eptazocine, levallorphan, sulpyrine, aspirin, acetaminophen, ergotamine, dihydroergotamine, sumatriptan, eletriptan, zolmitriptan, rizatriptan, naratriptan, almotriptan, frovatriptan, avitriptan, lasmiditan, olcegepant, telcagepant, donepezil, suxamethonium, pancuronium, sildenafil, vardenafil, apomorphine, tadalafil, atropine, scopolamine, homatropine methylbromide, chlorpromazine, digitoxin, levomepromazine, thioridazine, acepromazine, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, progesterone, testosterone, dehydroepiandrosterone, estrogen, estradiol, levonorgestrel, protamine, leucovorin, dimercaprol, deferoxamine, sodium thiosulfate, mifepristone, risperidone, olanzapine, thalidomide, civamide, acyclovir, valacyclovir, famciclovir, penciclovir, lopinavir, ritonavir, saquinavir, vidarabine, idoxuridine, nifedipine, nimodipine, amiodarone, loratadine, tretinoin, carmustin, beraprost sodium, and any combination thereof.

In some instances, the active agent is a small molecule drug, e.g., having a molecular weight of less than about 1000 grams/mole (g/mol), about 750 g/mol, or about 500 g/mol. In some instances, the active agent is an anti-migraine drug. In some instances, the active agent is an ergot alkaloid. In some instances, the active agent is dihydroergotamine (DHE) or a pharmaceutically acceptable salt thereof, e.g., DHE mesylate. In some instances, the active agent is indomethacin, midazolam, or phenobarbital. In some instances, the active agent is indomethacin or a pharmaceutically acceptable salt thereof. In some instances, the active agent is testosterone or a pharmaceutically acceptable salt thereof.

In some cases, an active agent disclosed herein is a peptide or a peptide-related compound, wherein the peptide or peptide-related compound has a molecular weight of about 10,000 Daltons (Da) or less, about 20,000 (Da) or less, about 30,000 (Da) or less, about 40,000 (Da) or less, or about 50,000 Daltons or less. In some instances, the active agent is selected from the group consisting of insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, FK-506, octreotide, carperitide, pramlintide, lanreotide, eptifibatide, albiglutide, pasireotide, teriparatide, exenatide, liraglutide, emfuvirtide, ziconotide, ecallantide, mifamurtide, nesiritide, peglinesatide, afamelanotide, linaclotide, lixisenatide, teduglutide, bentiromide, cureletide diethylamine, degarelix, ghrelin, atrial natriuretic peptide, a peptide analog thereof, and any combination thereof.

Methods and compositions presented herein can utilize an active agent in a freebase, salt, hydrate, polymorph, isomer, diastereomer, prodrug, metabolite, ion pair complex, or chelate form. An active agent can be formed using a pharmaceutically acceptable non-toxic acid or base, including an inorganic acid or base, or an organic acid or base. In some instances, an active agent that can be utilized in connection with the methods and compositions presented herein is a pharmaceutically acceptable salt derived from acids including, but not limited to, the following: acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. In some instances, the active agent is a salt of methanesulfonic acid. An alternative nomenclature of the methanesulfonic acid salt of DHE is DHE mesylate. For further description of pharmaceutically acceptable salts that can be used in the methods described herein see, for example, S. M. Barge et al., "Pharmaceutical Salts," 1977, J. Pharm. Sci. 66:1-19, which is incorporated herein by reference in its entirety.

In some cases, an average particle size of an active agent or a composition disclosed herein can be less than about 100 micrometer (μm), for example, about: 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 10 μm, 5 μm or less. In some instances, an average particle size of an active agent or a composition disclosed herein can be larger than 10 μm, for example, more than about: 250 μm, 200 μm, 190 µm, 180 µm, 170 µm, 160 µm, 150 µm, 140 µm, 130 µm, 120 µm, 110 µm, 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, or 15 µm. The particle size of an active agent or a powder composition can be about: 20-100 microns, 25-150 microns, 25-175 microns, 25-200 microns, 25-250 microns, 25-300 microns, 50-150 microns, 50-175 microns, 50-200 microns, 50-250 microns, 50-300 microns, 10-100 µm, for example, about: 15-90 µm, 15-80 µm, 15-70 µm, 15-60 µm, 15-50 µm, 15-40 µm, 15-30 µm, 15-20 µm, 15-20 µm, 10-90 µm, 10-80 µm, 10-70 µm, 10-60 µm, 10-50 µm, 10-40 µm, 10-30 µm, 10-20 µm, 20-90 µm, 20-80 µm, 20-70 µm, 20-60 µm, 20-50 µm, 20-40 µm, 20-30 µm, 30-90 µm, 30-80 µm, 30-70 µm, 30-60 µm, 30-50 µm, 30-40 µm, 40-90 µm, 40-80 µm, 40-70 µm, 40-60 µm, 40-50 µm, 50-90 µm, 50-80 µm, 50-70 µm, 50-60 µm, 60-90 µm, 60-80 µm, 60-70 µm, 70-90 µm, 70-80 µm, or 80-90 µm. The average particle size of the active agent or the composition can be about: 5.0 µm, 5.5 µm, 6.0 µm, 6.5 µm, 7.0 µm, 7.5 µm, 8.0 µm, 8.5 µm, 9.0 µm, 9.5 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, or 100 µm. In some instances, not less than 90% of the powder compositions presented herein have a particle diameter less than 150 µm, and not more than 5% of the particles have a diameter less than 5 µm. In some instances, the overall average particle size of the powder compositions presented herein are about 15 µm to about 30 µm, about 18 µm to about 25 µm, about 18 µm to about 20 µm, or about 20 µm.

In some cases, a total weight of a powder composition comprises about 0.4% to about 46%, or about 0.4% to about 23% or about 0.4% to about 9%, or about 2% to about 9%, or about 4% to about 9% of an active agent. In some instances, the total weight of the powder composition comprises about 0.3% to about 37%, or about 0.3% to about 18% or about 0.3% to about 7%, or about 2% to about 7%, or about 3% to about 9% of an active agent or a pharmaceutically acceptable salt thereof.

In some cases, a composition disclosed herein further comprises an additional active agent, for example: an adenosine receptor antagonist, a phosphodiesterase inhibitor, an acetylcholinesterase inhibitor, a vasodilator, xanthine, caffeine, paraxanthine, theobromine, and theophylline. For example, the methods and compositions further comprise caffeine. The additional active agent (e.g., caffeine) can be at least about 1% of the total weight of the powder composition, for example about: 1%, 2%, 3%, 4%, 5%, 6%, 7%, 8%, 9%, 10%, 15%, 20%, 25%, 30%, 35%, 40%, 45%, 50%, 55%, 60% or more of the total weight of the powder composition. The additional active agent (e.g., caffeine) can be about 1% to 60% of the total weight of the powder composition, for example, about: 1%-60%, 1%-50%, 1%-40%, 1%-30%, 1%-20%, 1%-10%, 1%-5%, 10%-60%, 10%-50%, 10%-40%, 10%-30%, 10%-20%, 20%-60%, 20%-50%, 20%-40%, 20%-30%, 30%-60%, 30%-50%, 30%-40%, 40%-60%, 40%-50%, or 50%-60% of the total weight of the powder composition. In some instances, the powder composition comprises about 5% to 10% of an additional active agent (e.g., caffeine). In some instances, the caffeine is anhydrous caffeine. In some instances, the powder composition comprises about 10% to 15% of an additional active agent (e.g., caffeine).

In some cases, the present disclosure provides for an intranasal pharmaceutical powder composition comprising particles that comprise an active agent and at least one member selected from the group consisting of a thickening agent, a carrier, a pH adjusting agent, a sugar alcohol, and any combination thereof, wherein: at least about 10%, about 20%, about 30%, about 40%, or about 50% by weight of the active agent in the particles is amorphous as determined by X-ray diffraction; when the active agent has a crystalline form, a solubility of the active agent in a crystalline form in an aqueous liquid ranges from about 0.1 µg/mL to about 1 milligram/milliliter (mg/mL) in water at a temperature of 37±0.5° C.; the particles have an average particle size of about 10 microns to about 300 microns, as measured by laser diffraction; and when the intranasal pharmaceutical powder composition is administered, a pharmacokinetic parameter of the active agent improves by at least about 15%, compared to a corresponding composition that comprises the active agent in a crystalline form when administered. In some instances, the pharmaceutical powder composition further comprises particles that comprise the active agent and are free from the thickening agent, the carrier, the pH adjuster, the sugar alcohol, or a combination thereof. In some instances, the active agent is a non-peptide/non-protein drug. In some instances, the particles have an average particle size of from about 15 to about 100 µm, as measured by laser diffraction. In some instances, the particles have an average particle size of from about 20 to about 50 µm, as measured by laser diffraction. In some instances, the particles are spray dried. In some instances, the active agent is spray dried onto the carrier, the thickening agent, the pH adjuster, the sugar alcohol or a combination thereof to form the particles. In some instances, the solubility is measured at a pH of about 6.0, 6.1, 6.2, 6.3, 6.4, 6.5, 6.6, 6.7, 6.8, 6.9, 7.0, 7.1, 7.2, 7.3, 7.4, 7.5, 7.8, 7.9, 7.10, for example, ranging from about 6.8 to about 7.4. In some instances, the particles comprise the carrier that is at least partially water insoluble at 37±0.5° C. In some instances, the water insolubility is measured at a pH ranging from about 6.8 to about 7.4. In some instances, the particles further comprise the thickening agent, and wherein the carrier has lower water solubility than that of the thickening agent. In some instances, the particles comprise the carrier that is at least partially adhesive to mucus. In some instances, the particles comprise the carrier that comprises an oligosaccharide, a polysaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, β cyclodextrin, or any combination thereof. In some instances, the particles comprise the carrier that has an average particle size of from about 10 to about 100 µm, as measured by laser diffraction. In some instances, the carrier has an average particle size of about 20 µm, as measured by laser diffraction. In some instances, the particles comprise the thickening agent that is at least partially water soluble at 37±0.5° C. In some instances, the water solubility is measured at a pH ranging from about 6.8 to about 7.4. In some instances, the particles further comprise the carrier, and wherein the thickening agent has higher water solubility than that of the carrier. In some instances, the particles comprise that the thickening agent binds to the active agent. In some instances, the particles further comprise the carrier, and wherein the thickening agent binds to the active agent and the carrier. In some instances, the particles comprise the thickening agent that comprises a polysaccharide. In some instances, the thickening agent comprises hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 µm, or about 15-200 microns, as measured by laser diffraction. In some instances, the particles have an average particle size of about 15 µm, or about 50-150 microns, as measured by laser diffraction. In some instances, the particles comprise the thickening agent and the carrier and have an average particle size of from about 10 to about 50 µm, as measured by laser diffraction. In some instances, the particles have an average particle size of about 20 or about 23 µm, as measured by laser diffraction. In some instances, the pharmaceutical powder composition further comprises a fluidizing agent. In some instances, the fluidizing agent comprises a tribasic calcium phosphate. In some instances, the administration of the pharmaceutical powder composition improves the pharmacokinetic parameter of the active agent by at least about: 20%, 25%, 30%, 40%, 45%, 50%, 60%, 70%, 80%, 90%, 100%, 150%, 200%, 250%, 300%, 400%, or 500%, when compared to administration of the corresponding composition that comprises the active agent in the crystalline form. In some instances, the improved pharmacokinetic parameter comprises a greater relative bioavailability from 0 min to 15 min ($rBA_{0-15min}$), a greater relative bioavailability from 0 min to 30 min ($rBA_{0-30min}$), a greater relative bioavailability from 0 min to 60 min ($rBA_{0-60min}$), or any combination thereof. In some instances, the improved pharmacokinetic parameter comprises an average $rBA_{0-15min}$, and the improvement is at least about 100%, e.g., at least about: 115% or 150%. In some instances, the average $rBA_{0-15min}$ is about 150% to 1500% in serum of the subject. In some instances, the improved pharmacokinetic parameter comprises an average $rBA_{0-30min}$, and the improvement is at least about 80%, e.g., at least about 115%. In some instances, the improvement is about 400%. In some instances, the improved pharmacokinetic parameter comprises an average $rBA_{0-60min}$, and the improvement is at least 100%, e.g., at least about 115%. In some instances, the improvement is about 200%. In some instances, the improved pharmacokinetic parameter comprises a higher maximum blood concentration ($C_{max}$). In some instances, the improved pharmacokinetic parameter comprises a shorter time to reach maximum blood concentration (Tmax). In some instances, the improved pharmacokinetic parameter comprises an increased area under the curve (AUC) for blood concentration-time profile. In some instances, the pharmaceutical powder composition further comprises an additional active agent. In some instances, the additional active agent comprises caffeine, which is amorphous, crystalline, at least 20% of amorphous by weight of the caffeine, or any combination thereof. In some instances, at least about: 25%, 30%, 40%, 45%, 50%, 55%, 60%, 65%, 70%, 75%, 80%, 85%, 90%, 95%, or 98% by weight of the active agent is amorphous. In some instances, the pharmaceutical powder composition retains at least about: 80%, 85%, 90%, or 95% by weight of the active agent in a closed container after a period of at least about: 30, 60, 120, 180, 360, 720, or 1080 days. In some instances, the container is kept at about 15° C., about 20° C., about 30° C., about 40° C., about 50° C., about 60° C., or about 70° C., for example about 20° C. to about 40° C. at a standard atmosphere pressure with a relative humidity of about 50% to about 75%. For example, the relative humidity may be about 40%, about 45%, about 50%, about 55%, about 60%, about 65%, about 70%, about 75%, about 80%, or about 85%. In some instances, the container is kept at about 25° C. at a standard atmosphere pressure with a relative humidity of about 50%. In some instances, the crystalline form comprises a polymorph.

In some cases, an active agent disclosed herein has an average particle size (e.g., diameter) of 5 µm or larger than 5 µm.

In some cases, an active agent disclosed herein is suspended in methanol before spray drying.

In some cases, an active agent is present in an amount of about: 2-4%, 1-5%, 1-10%, 1-15%, 1-20%, 1-25%, 1-30%, 1-40%, 10-50%, 10-40%, 10-30%, or 15-25%, by weight based on a weight of the particles or a pharmaceutical powder composition, for example about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50%.

In some cases, particle size for each active agent, excipient and powder preparation are determined under a dry powder dispersion condition by a laser diffraction system (Mastersizer 2000, Malvern Instruments Ltd.).

Pharmacokinetics

Pharmacokinetic data disclosed herein (e.g., $C_{max}$, $T_{max}$, $AUC_{0-t}$, $AUC_{0-180\ minutes}$, $AUC_{0-inf}$, $T_{1/2}$) can be measured from a primate, preferably a monkey, and preferably a Cynomolgus monkey, after a powder composition disclosed herein is administered. Alternatively, the pharmacokinetic data disclosed herein (e.g., $C_{max}$, $T_{max}$, $AUC_{0-t}$, $AUC_{0-180\ minutes}$, $AUC_{0-inf}$, $T_{1/2}$) can be measured from a human subject after a powder composition disclosed herein is administered.

Presented herein are powder compositions comprising an active agent. In addition to such compositions, also presented herein are methods comprising intranasally administering powder compositions containing dihydroergotamine, or a pharmaceutically acceptable salt thereof. In some cases, the composition may not be a liquid solution or a liquid spray composition.

Methods disclosed herein can be used for treating a disease or condition, for example, for pain, for hormone disorder, or for rapid onset treatment of headache, including migraine, e.g., acute treatment of migraine with or without aura.

Compositions disclosed herein can comprise a) an active agent, wherein the total dose of an active agent administered is 0.1-10.0 mg; b) a microcrystalline cellulose comprising at least 15% of the total weight of the composition. In some cases, a mean $T_{max}$ of an active agent after administration of the powder composition may be about 1-120 minutes. The presented methods can comprise: intranasally administering to a human a powder composition comprising: a) an active agent, wherein the total dose of an active agent administered is 0.1-10.0 mg; b) microcrystalline cellulose comprising at least 15% of the total weight of the composition.

Compositions and methods disclosed herein may further comprise at least one of the following: a) wherein a mean $T_{max}$ of an active agent after administration of the powder composition is about 1 to about 120 minutes; b) wherein a ($AUC_{0-30\ min}/AUC_{0-inf}$)×100% of an active agent after administration of the powder composition is greater than 2.5%; c) wherein a ($AUC_{0-30\ min}/AUC_{0-inf}$)×100% of an active agent after administration of the powder composition is greater than 2.5% to 25%; d) wherein a ($AUC_{0-60\ min}/AUC_{0-inf}$)×100% of an active agent after administration of the powder composition is greater than 10%; e) wherein a ($AUC_{0-60\ min}/AUC_{0-inf}$)×100% of an active agent after administration of the powder composition is greater than 10% to 45%; f) wherein a ($AUC_{0-120\ min}/AUC_{0-inf}$)×100% of an active agent after administration of the powder composition is greater than 25%; g) wherein a $(AUC_{0-120\ min}/AUC_{0-inf})\times100\%$ of an active agent after administration of the powder composition is greater than 25% to 75%; h) wherein when the powder composition is administered to a primate, preferably a monkey, and preferably a Cynomolgus monkey, a $(AUC_{0-30\ min}/AUC_{0-inf})\times100\%$ is greater than 10%; i) wherein when the powder composition is administered to a primate, preferably a monkey, and preferably a Cynomolgus monkey, a $(AUC_{0-60\ min}/AUC_{0-inf})\times100\%$ is greater than 20%; j) wherein when the powder composition is administered to a primate, preferably a monkey, and preferably a Cynomolgus monkey, a $(AUC_{0-120\ min}/AUC_{0-inf})\times100\%$ is greater than 40%. The mean $T_{max}$ after administration of the powder composition can be measured from a primate, preferably a monkey, and preferably a Cynomolgus monkey.

In some instances, a $(AUC_{0-30\ min}/AUC_{0-inf})\times100\%$ of an active agent after administration of the powder composition is greater than 2.5%, for example, greater than 2.5%, 5%, 6%, 7%, 8%, 9%, 10%, 15%, 20%, 25%, or 30%. In some instances, the $(AUC_{0-30\ min}/AUC_{0-inf})\times100\%$ of an active agent after administration of the powder composition is greater than 2.5% to 75%, for example, 2.5% to 50%, 2.5% to 25%, 2.5% to 15%, or 2.5% to 5%. In some instances, a $(AUC_{0-60\ min}/AUC_{0-inf})\times100\%$ of an active agent after administration of the powder composition is greater than 5%, for example, greater than 5%, 6%, 7%, 8%, 9%, 10%, 15%, 20%, 25%, 30%, 35%, 40%, 45%, 50%, 55%, or 60%. In some instances, the $(AUC_{0-60\ min}/AUC_{0-inf})\times100\%$ of an active agent after administration of the powder composition is greater than 5% to 75%, for example, 5% to 50%, 5% to 25%, 5% to 15%, 5% to 10%, 10% to 50%, 10% to 45%, 10% to 25%, 10% to 15%, 15% to 50%, 15% to 25%, or 25% to 50%. In some instances, a $(AUC_{0-120\ min}/AUC_{0-inf})\times100\%$ of an active agent after administration of the powder composition is greater than 5%, for example, greater than 5%, 6%, 7%, 8%, 9%, 10%, 15%, 20%, 25%, 30%, 35%, 40%, 45%, 50%, 55%, 60%, 65%, 70%, or 75%. In some instances, the $(AUC_{0-120\ min}/AUC_{0-inf})\times100\%$ of an active agent after administration of the powder composition is greater than 15% to 75%, for example, 15% to 75%, 15% to 50%, 15% to 25%, 25% to 75%, 25% to 50%, or 50% to 75%.

In some instances, when the powder composition is administered to a primate, preferably a monkey, and preferably a Cynomolgus monkey, a $(AUC_{0-30\ min}/AUC_{0-inf})\times100\%$ of an active agent after administration of the powder composition is greater than 2.5%, for example, greater than 2.5%, 5%, 6%, 7%, 8%, 9%, 10%, 15%, 20%, 25%, or 30%. In some instances, the $(AUC_{0-30\ min}/AUC_{0-inf})\times100\%$ of an active agent after administration of the powder composition is greater than 2.5% to 75%, for example, 2.5% to 50%, 2.5% to 25%, 2.5% to 15%, or 2.5% to 5%. For example, the $(AUC_{0-30\ min}/AUC_{0-inf})\times100\%$ of an active agent after administration of the powder composition may be about 10%. In some instances, when the powder composition is administered to a primate, preferably a monkey, and preferably a Cynomolgus monkey, a $(AUC_{0-60\ min}/AUC_{0-inf})\times100\%$ of an active agent after administration of the powder composition is greater than 5%, for example, greater than 5%, 6%, 7%, 8%, 9%, 10%, 15%, 20%, 25%, 30%, 35%, 40%, 45%, 50%, 55%, or 60%. In some instances, the $(AUC_{0-60\ min}/AUC_{0-inf})\times100\%$ of an active agent after administration of the powder composition is greater than 5% to 75%, for example, 5% to 50%, 5% to 25%, 5% to 15%, 5% to 10%, 10% to 50%, 10% to 45%, 10% to 25%, 10% to 15%, 15% to 50%, 15% to 25%, or 25% to 50%. For example, the $(AUC_{0-60\ min}/AUC_{0-inf})\times100\%$ of an active agent after administration of the powder composition may be about 20%. In some instances, when the powder composition is administered to a primate, preferably a monkey, and preferably a Cynomolgus monkey, a $(AUC_{0-120\ min}/AUC_{0-inf})\times100\%$ of an active agent after administration of the powder composition is greater than 5%, for example, greater than 5%, 6%, 7%, 8%, 9%, 10%, 15%, 20%, 25%, 30%, 35%, 40%, 45%, 50%, 55%, 60%, 65%, 70%, or 75%. In some instances, the $(AUC_{0-120\ min}/AUC_{0-inf})\times100\%$ of an active agent after administration of the powder composition is greater than 15% to 75%, for example, 15% to 75%, 15% to 50%, 15% to 25%, 25% to 75%, 25% to 50%, or 50% to 75%. For example, the $(AUC_{0-120\ min}/AUC_{0-inf})\times100\%$ of an active agent after administration of the powder composition may be about 40%.

Compositions disclosed herein can comprise a) an active agent, wherein the total dose of DHE administered is 0.1-10.0 mg; and b) a microcrystalline cellulose comprising at least 15% of the total weight of the composition. In some cases, a mean $T_{max}$ of an active agent after administration of the powder composition is about 1-120 minutes. The presented methods can comprise: intranasally administering to a human a powder composition comprising: a) an active agent, wherein the total dose of an active agent administered is 0.1-10.0 mg; b) a microcrystalline cellulose comprises at least 15% of the total weight of the composition; wherein a mean $T_{max}$ of an active agent after administration of the powder composition is about 1-120 minutes. The mean $T_{max}$ after administration of the powder composition can be measured from a human subject.

In some instances, the methods and compositions comprise a mean $T_{max}$ of an active agent after administration of the composition of at least about 1 minutes, for example, at least about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 25 minutes, 30 minutes, 35 minutes, 40 minutes, 45 minutes, 50 minutes, 60 minutes, 90 minutes, or 120 minutes. The mean $T_{max}$ of an active agent after administration of the composition can be about 1 to about 120 minutes, for example, about 1-120 minutes, about 1-90 minutes, about 1-60 minutes, about 1-50 minutes, 1-40 minutes, 1-30 minutes, 1-20 minutes, 1-10 minutes, 1-5 minutes, about 1-2 minutes, about 5-120 minutes, about 5-90 minutes, about 5-60 minutes, about 5-50 minutes, 5-40 minutes, 5-30 minutes, 5-25 minutes, 5-20 minutes, 5-10 minutes, about 10-120 minutes, about 10-90 minutes, about 10-60 minutes, about 10-50 minutes, 10-40 minutes, 10-30 minutes, 10-20 minutes, about 20-120 minutes, about 20-90 minutes, about 20-60 minutes, about 20-50 minutes, 20-40 minutes, 20-30 minutes, about 30-120 minutes, about 30-90 minutes, about 30-60 minutes, about 30-50 minutes, 30-40 minutes, about 40-120 minutes, about 40-90 minutes, about 40-60 minutes, 40-50 minutes, about 50-120 minutes, about 50-90 minutes, about 50-60 minutes, about 60-120 minutes, about 60-90 minutes, or about 90-120 minutes. The mean $T_{max}$ after administration of the powder composition can be measured from a primate, preferably a monkey, and preferably a Cynomolgus monkey. The mean $T_{max}$ after administration of the powder composition can be measured from a human subject.

In some instances, the methods and compositions comprise a mean $C_{max}$ of an active agent after administration of the composition of at least about 0.01 nanogram/milliliter (ng/mL), for example, at least about 0.01 ng/mL, 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1 ng/mL, 1.5 ng/mL, 2 ng/mL, 2.5 ng/mL, 3 ng/mL, 3.5 ng/mL, 4 ng/mL, 4.5 ng/mL, 5 ng/mL, 5.5 ng/mL, 6 ng/mL, 6.5 ng/mL, 7 ng/mL, 7.5 ng/mL, 8 ng/mL, 8.5 ng/mL, 9 ng/mL, 9.5 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 110 ng/mL, 120 ng/mL, 130 ng/mL, 140 ng/mL, or 150 ng/mL. The mean $C_{max}$ of an active agent after administration of the composition can be about 0.1 to about 150 ng/mL, for example, about 0.1-150 ng/mL, 0.1-130 ng/mL, 0.1-110 ng/mL, 0.1-90 ng/mL, 0.1-70 ng/mL, 0.1-50 ng/mL, 0.1-30 ng/mL, 0.1-10 ng/mL, 0.1-5 ng/mL, 0.1-1.0 ng/mL, 0.1-0.5 ng/mL, 1-150 ng/mL, 1-130 ng/mL, 1-110 ng/mL, 1-90 ng/mL, 1-70 ng/mL, 1-50 ng/mL, 1-30 ng/mL, 1-10 ng/mL, 1-5 ng/mL, 5-150 ng/mL, 5-130 ng/mL, 5-110 ng/mL, 5-90 ng/mL, 5-70 ng/mL, 5-50 ng/mL, 5-30 ng/mL, 5-10 ng/mL, 10-150 ng/mL, 10-130 ng/mL, 10-110 ng/mL, 10-90 ng/mL, 10-70 ng/mL, 10-50 ng/mL, 10-30 ng/mL, 30-150 ng/mL, 30-130 ng/mL, 30-110 ng/mL, 30-90 ng/mL, 30-70 ng/mL, 30-50 ng/mL, 50-150 ng/mL, 50-130 ng/mL, 50-110 ng/mL, 50-90 ng/mL, 50-70 ng/mL, 70-150 ng/mL, 70-130 ng/mL, 70-110 ng/mL, 70-90 ng/mL, 90-150 ng/mL, 90-130 ng/mL, 90-110 ng/mL, 110-150 ng/mL, 110-130 ng/mL, or 130-150 ng/mL. The mean $C_{max}$ after administration of the powder composition can be measured from a primate, preferably a monkey, and preferably a Cynomolgus monkey. The mean $C_{max}$ after administration of the powder composition can be measured from a human subject.

In some instances, the methods and compositions comprise a mean $AUC_{0-inf}$ of an active agent after administration of the composition of at least about 0.5 nanogram·hour/milliliter (ng·h/mL), for example, at least about 0.5 ng·h/mL, 1 ng·h/mL, 2 ng·h/mL, 3 ng·h/mL, 4 ng·h/mL, 5 ng·h/mL, 6 ng·h/mL, 7 ng·h/mL, 8 ng·h/mL, 9 ng·h/mL, 10 ng·h/mL, 20 ng·h/mL, 30 ng·h/mL, 40 ng·h/mL, 50 ng·h/mL, 60 ng·h/mL, 70 ng·h/mL, 80 ng·h/mL, 90 ng·h/mL, 100 ng·h/mL, 200 ng·h/mL, 300 ng·h/mL, 400 ng·h/mL, 500 ng·h/mL, 600 ng·h/mL, or 700 ng·h/mL. The mean $AUC_{0-inf}$ of an active agent after administration of the composition can be about 0.5 to about 700 ng·h/mL, for example, about 0.5-700 ng·h/mL, 0.5-500 ng·h/mL, 0.5-300 ng·h/mL, 0.5-100 ng·h/mL, 0.5-80 ng·h/mL, 0.5-60 ng·h/mL, 0.5-40 ng·h/mL, 0.5-20 ng·h/mL, 0.5-10 ng·h/mL, 0.5-5 ng·h/mL, 0.5-2 ng·h/mL, 0.5-1 ng·h/mL, 1-700 ng·h/mL, 1-500 ng·h/mL, 1-300 ng·h/mL, 1-100 ng·h/mL, 1-80 ng·h/mL, 1-60 ng·h/mL, 1-40 ng·h/mL, 1-20 ng·h/mL, 1-10 ng·h/mL, 1-5 ng·h/mL, 10-700 ng·h/mL, 10-500 ng·h/mL, 10-300 ng·h/mL, 10-100 ng·h/mL, 10-80 ng·h/mL, 10-60 ng·h/mL, 10-40 ng·h/mL, 10-20 ng·h/mL, 20-700 ng·h/mL, 20-500 ng·h/mL, 20-300 ng·h/mL, 20-100 ng·h/mL, 20-80 ng·h/mL, 20-60 ng·h/mL, 20-40 ng·h/mL, 40-700 ng·h/mL, 40-500 ng·h/mL, 40-300 ng·h/mL, 40-100 ng·h/mL, 40-80 ng·h/mL, 40-60 ng·h/mL, 60-700 ng·h/mL, 60-500 ng·h/mL, 60-300 ng·h/mL, 60-100 ng·h/mL, 60-80 ng·h/mL, 80-700 ng·h/mL, 80-500 ng·h/mL, 80-300 ng·h/mL, 80-100 ng·h/mL, 100-700 ng·h/mL, 100-500 ng·h/mL, 100-300 ng·h/mL, 300-700 ng·h/mL, 300-500 ng·h/mL, or 500-700 ng·h/mL. The mean $AUC_{0-inf}$ after administration of the powder composition can be measured from a primate, preferably a monkey, and preferably a Cynomolgus monkey. The mean $AUC_{0-inf}$ after administration of the powder composition can be measured from a human subject.

In some instances, the methods and compositions comprise a mean $AUC_{0-t}$ of an active agent after administration of the composition of at least about 0.5 ng·h/mL, for example, at least about 0.5 ng·h/mL, 1 ng·h/mL, 2 ng·h/mL, 3 ng·h/mL, 4 ng·h/mL, 5 ng·h/mL, 6 ng·h/mL, 7 ng·h/mL, 8 ng·h/mL, 9 ng·h/mL, 10 ng·h/mL, 20 ng·h/mL, 30 ng·h/mL, 40 ng·h/mL, 50 ng·h/mL, 60 ng·h/mL, 70 ng·h/mL, 80 ng·h/mL, 90 ng·h/mL, 100 ng·h/mL, 200 ng·h/mL, 300 ng·h/mL, 400 ng·h/mL, 500 ng·h/mL, 600 ng·h/mL, or 700 ng·h/mL. The mean $AUC_{0-inf}$ of an active agent after administration of the composition can be about 0.5 to about 700 ng·h/mL, for example, about 0.5-700 ng·h/mL, 0.5-500 ng·h/mL, 0.5-300 ng·h/mL, 0.5-100 ng·h/mL, 0.5-80 ng·h/mL, 0.5-60 ng·h/mL, 0.5-40 ng·h/mL, 0.5-20 ng·h/mL, 0.5-10 ng·h/mL, 0.5-5 ng·h/mL, 0.5-2 ng·h/mL, 0.5-1 ng·h/mL, 1-700 ng·h/mL, 1-500 ng·h/mL, 1-300 ng·h/mL, 1-100 ng·h/mL, 1-80 ng·h/mL, 1-60 ng·h/mL, 1-40 ng·h/mL, 1-20 ng·h/mL, 1-10 ng·h/mL, 1-5 ng·h/mL, 10-700 ng·h/mL, 10-500 ng·h/mL, 10-300 ng·h/mL, 10-100 ng·h/mL, 10-80 ng·h/mL, 10-60 ng·h/mL, 10-40 ng·h/mL, 10-20 ng·h/mL, 20-700 ng·h/mL, 20-500 ng·h/mL, 20-300 ng·h/mL, 20-100 ng·h/mL, 20-80 ng·h/mL, 20-60 ng·h/mL, 20-40 ng·h/mL, 40-700 ng·h/mL, 40-500 ng·h/mL, 40-300 ng·h/mL, 40-100 ng·h/mL, 40-80 ng·h/mL, 40-60 ng·h/mL, 60-700 ng·h/mL, 60-500 ng·h/mL, 60-300 ng·h/mL, 60-100 ng·h/mL, 60-80 ng·h/mL, 80-700 ng·h/mL, 80-500 ng·h/mL, 80-300 ng·h/mL, 80-100 ng·h/mL, 100-700 ng·h/mL, 100-500 ng·h/mL, 100-300 ng·h/mL, 300-700 ng·h/mL, 300-500 ng·h/mL, or 500-700 ng·h/mL. The mean $AUC_{0-inf}$ after administration of the powder composition can be measured from a primate, preferably a monkey, and preferably a Cynomolgus monkey. The mean $AUC_{0-inf}$ after administration of the powder composition can be measured from a human subject. The measurement can be taken 5 minutes, 10 minutes, 20 minutes, 30 minutes, 60 minutes, 90 minutes, 120 minutes, 180 minutes, 240 minutes, 300 minutes, 360 minutes, 420 minutes, or 480 minutes.

In some instances, the methods and compositions comprise a mean $T_{1/2}$ of an active agent after administration of the composition of at least about 10 minutes, for example, at least about 10 minutes, 20 minutes, 30 minutes, 40 minutes, 50 minutes, 60 minutes, 70 minutes, 80 minutes, 90 minutes, 100 minutes, 120 minutes, 150 minutes, 200 minutes, 250 minutes, or 300 minutes. The mean $T_{1/2}$ of an active agent after administration of the composition can be about 10 to about 300 minutes, for example, about 10-300 minutes, 10-250 minutes, 10-200 minutes, 10-150 minutes, 10-120 minutes, 10-100 minutes, 10-80 minutes, 10-60 minutes, 10-40 minutes, 10-20 minutes, 20-300 minutes, 20-250 minutes, 20-200 minutes, 20-150 minutes, 20-120 minutes, 20-100 minutes, 20-80 minutes, 20-60 minutes, 20-40 minutes, 40-300 minutes, 40-250 minutes, 40-200 minutes, 40-150 minutes, 40-120 minutes, 40-100 minutes, 40-80 minutes, 40-60 minutes, 60-300 minutes, 60-250 minutes, 60-200 minutes, 60-150 minutes, 60-120 minutes, 60-100 minutes, 60-80 minutes, 80-300 minutes, 80-250 minutes, 80-200 minutes, 80-150 minutes, 80-120 minutes, 80-100 minutes, 100-300 minutes, 100-250 minutes, 100-200 minutes, 100-150 minutes, 100-120 minutes, 120-300 minutes, 120-250 minutes, 120-200 minutes, 120-150 minutes, 150-300 minutes, 150-250 minutes, 150-200 minutes, 200-300 minutes, 200-250 minutes, or 250-300 minutes. For example, the mean $T_{1/2}$ of an active agent after administration of the composition is about 100 to about 300 minutes. The mean $T_{1/2}$ after administration of the powder composition can be measured from a monkey (e.g., Cynomolgus monkeys). The mean $T_{1/2}$ after administration of the powder composition can be measured from a human subject.

In some instances, the methods presented herein comprising intranasally administering to a human a powder composition comprising an active agent, wherein the method further comprises at least one of the following: wherein a mean $T_{max}$ of an active agent after administration of the composition is about 2 to about 50 minutes; b) wherein a mean $C_{max}$ of an active agent after administration of the composition is about 0.1 to about 150 ng/mL; c) wherein a mean $AUC_{0-inf}$ of an active agent after administration of the composition is about 1 to about 700 ng·h/mL; d) wherein a mean $T_{1/2}$ of an active agent after administration of the composition is about 100 to about 300 minutes. In some instances, the mean $T_{max}$ of an active agent after administration of the composition is about 2 to about 50 minutes. In some instances, the mean $C_{max}$ of an active agent after administration of the composition is about 0.1 to about 150 ng/mL. In some instances, the mean $AUC_{0-inf}$ of an active agent after administration of the composition is about 1 to about 700 ng·h/mL. In some instances, the mean $T_{1/2}$ of an active agent after administration of the composition is about 100 to about 300 minutes. The mean $T_{max}$, $C_{max}$, $AUC_{0-inf}$, and/or $T_{1/2}$ after administration of the powder composition can be measured from a primate, preferably a monkey, and preferably a Cynomolgus monkey. The mean $T_{max}$, $C_{max}$, $AUC_{0-inf}$, and/or $T_{1/2}$ after administration of the powder composition can be measured from a human subject.

In one case of an active agent, the mean $T_{max}$ may be about 10 to about 30 minutes, the mean $C_{max}$ can be about 0.5 to about 6 ng/mL, the mean $AUC_{0-inf}$ can be about 1 to about 15 ng·h/mL, and the mean $T_{1/2}$ can be about 100 to about 300 minutes. In another case, the mean $T_{max}$ may be about 10 to about 50 minutes, the mean $C_{max}$ can be about 1 to about 15 ng/mL, the mean $AUC_{0-inf}$ can be about 10 to about 50 ng·h/mL, and the mean $T_{1/2}$ can be about 100 to about 300 minutes. In another case of an active agent, the mean $T_{max}$ may be about 10 to about 50 minutes, the mean $C_{max}$ can be about 2 to about 20 ng/mL, the mean $AUC_{0-inf}$ can be about 15 to about 110 ng·h/mL, and the mean $T_{1/2}$ can be about 100 to about 300 minutes. In another case of an active agent, the mean $T_{max}$ may be about 10 to about 50 minutes, the mean $C_{max}$ can be about 2 to about 50 ng/mL, the mean $AUC_{0-inf}$ can be about 15 to about 200 ng·h/mL, and the mean $T_{1/2}$ can be about 100 to about 300 minutes. The mean $T_{max}$, $C_{max}$, $AUC_{0-inf}$, and/or $T_{1/2}$ after administration of the powder composition can be measured from a primate, preferably a monkey, and preferably a Cynomolgus monkey. The mean $T_{max}$, $C_{max}$, $AUC_{0-inf}$, and/or $T_{1/2}$ after administration of the powder composition can be measured from a human subject.

In some cases, the powder composition is administered such that the intersubject variability in an active agent $C_{max}$ can be less than 50%. For example, the intersubject variability in an active agent $C_{max}$ may be less than 50%, 30%, 25%, 20%, 15%, 10%, or 5%. In some cases, the powder composition can be administered such that the intersubject variability in an active agent $T_{max}$ is less than 30%. For example, the intersubject variability in an active agent $T_{max}$ can be less than 30%, 25%, 20%, 15%, 10%, or 5%. In some cases, the powder composition is administered such that the intersubject variability in DHE $AUC_{0-inf}$ may be less than 30%. For example, the intersubject variability in an active agent $AUC_{0-inf}$ can be less than 30%, 25%, 20%, 15%, 10%, or 5%. In some cases, the powder composition is administered such that the intersubject variability in an active agent $T_{1/2}$ can be less than 30%. For example, the intersubject variability in an active agent $T_{1/2}$ may be less than 30%, 25%, 20%, 15%, 10%, or 5%. The intersubject variability in an active agent $T_{max}$, $C_{max}$, $AUC_{0-inf}$, and/or $T_{1/2}$ after administration of the powder composition can be measured from primates, preferably monkeys, and preferably a Cynomolgus monkeys. The intersubject variability in an active agent $T_{max}$, $C_{max}$, $AUC_{0-inf}$, and/or $T_{1/2}$ after administration of the powder composition can be measured from human subjects.

In some cases, a pharmacokinetic parameter disclosed herein is determined with an analysis of a blood sample or plasma sample collected at one or more time points of about: 2, 5, 10, 15, 20, 30, 45, 60, 120, or 180 minutes after intranasal administration. In some instances, the analysis comprises a measurement of a plasma concentration of DHE, 8'-hydroxy-DHE, or a combination thereof in the blood sample or plasma sample. In some instances, the analysis is conducted with liquid chromatography (LC), mass spectrometry (MS), or a combination thereof. In some instances, the analysis is conducted with a LC/MS/MS method.

In some instances, powder compositions herein further comprise an additional active agent disclosed herein, e.g., caffeine, for example, anhydrous caffeine. In some instances, the powder compositions utilized as part of the methods of treating headache, including migraine, comprise about 1-60%, about 1-25%, about 10-60%, or about 10-25% of an active agent. In some instances, the powder compositions utilized as part of the methods of treating headache, including migraine, comprise about 1%, about 5%, about 6%, about 10%, about 12%, about 20%, about 23%, about 39%, about 48%, about 50%, or about 58% of an active agent.

In some instances, an average particle size of the active agent is about 10-100 µm, for example, about 10 to 75 µm, about 10 to 50 µm, about 10-30 µm, about 10-20 µm, about 15-20 µm, about 10 µm, about 15 µm, about 16 µm, about 17 µm, about 18 µm, about 19 µm, or about 20 µm. In some instances, not less than 90% of the active agent's particles in the powder compositions presented herein have a diameter less than 150 µm, and not more than 5% of the caffeine particles in the powder composition have a diameter less than 10 µm. In some instances, the overall average particle size of the active agent's particles in the powder compositions presented herein is about 15 to about 30 µm, about 18 to about 25 µm, about 18 to about 20 µm, or about 20 µm.

In some instances, a powder composition comprises about an active agent (e.g., about: 0.5 mg, 1.0 mg, 1.5 mg, 2 mg) and is administered such that the mean $T_{max}$ of an active agent is about 10-30 minutes. In some instances, the powder composition is administered such that the mean $T_{max}$ of an active agent is about 2-50 minutes. In some instances, the powder composition is administered such that the mean $T_{max}$ of an active agent is about 2-30 minutes. In some instances, the powder composition is administered such that the mean $C_{max}$ of an active agent is about 0.5-10 ng/mL. In some instances, the powder composition is administered such that the mean $AUC_{0-inf}$ of an active agent is about 1-15 ng·h/mL. In some instances, the powder composition is administered such that the mean $T_{max}$ of an active agent is about 2-30 minutes, the mean $C_{max}$ of an active agent is about 0.5-6 ng/mL, the mean $AUC_{0-inf}$ of an active agent is about 1-15 ng·h/mL, and the mean $T_{1/2}$ of an active agent is about 100-300 minutes. In some instances, the intersubject variability in an active agent $C_{max}$ is less than 30%.

In some instances, a powder composition comprises an active agent (e.g., DHE or a salt thereof, DHE mesylate). In some instances, the powder composition is administered to a single nostril of the human having a headache, including migraine. In some instances, a portion of the powder composition is administered to each nostril of the human having a headache, e.g., migraine. For example, in some instances, about half of the powder composition is administered to one nostril and about half of the powder composition is administered to the other nostril of the human in need thereof.

In some instances, a total dose of an active agent administered is about 0.1-6.0 mg. In some instances, the total dose of an active agent administered is about 0.5-6.0 mg. In some instances, the total dose of an active agent administered is about 1.0-4.0 mg. In some instances, the total dose of an active agent administered is about 1.0-5.0 mg. In some instances, the total dose of an active agent administered is about 0.1 mg, about 0.5 mg, about 1.0 mg, about 1.5 mg, about 2.0 mg, about 3.0 mg, about 4.0 mg, about 5.0 mg, about 7.5 mg, or about 10.0 mg. In some instances, the total dose is administered into a single nostril. In some instances, a portion of the total dose is administered into each nostril. In some instances, about half of the total dose is administered into one nostril and the remaining half is administered into the other nostril.

Excipients

In some cases, a composition disclosed herein comprises one or more excipients, e.g., different substance, or same substance but different sizes. In some instances, the excipient comprises a carrier, e.g., water-insoluble polysaccharide or oligosaccharide. In some instances, the carrier is selected from a group consisting of cellulose acetate, cellulose acetate butyrate, cellulose acetate propionate, cellulose acetate phthalate, chitosan, β-cyclodextrin, ethyl cellulose, hydroxypropylmethyl cellulose phthalate (HPMCP), microcrystalline cellulose, starch, and any combination thereof. In some instances, the excipient comprises a thickening agent, e.g., a water-soluble polysaccharide. In some instances, the thickening agent is selected from the group consisting of hydroxy propyl methyl cellulose (HPMC), acacia, alginic acid, colloidal silicone dioxide, carboxymethylcellulose calcium, gelatin, hydroxy propyl cellulose, hydroxyl propyl cellulose (hypromellose), methyl cellulose, sucrose, sodium alginate, sodium carboxy methyl cellulose, and any combination thereof. In some instances, the excipient comprises a first excipient (any excipient disclosed herein) and a second excipient (any excipient disclosed herein). In some instances, the excipient comprises a carrier (e.g., microcrystalline cellulose) and a thickening agent (e.g., HPMC).

In some instances, particles comprise a thickening agent that is present in an amount of about: 0.1-0.5%, 0.05-1%, 0.05-2%, 0.05-3%, 0.05-4%, 0.05-5%, 4-6%, 3-7%, 2-8%, 1-10%, or 1-20% by weight based on a weight of the particles or a pharmaceutical powder composition, for example about: 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, or 20 percent. In some instances, particles comprise microcrystalline cellulose that is present in an amount of about: 10-95%, 10-75%, 15-55%, 20-75%, 35-75%, or 40-75% by weight based on a weight of the particles or a pharmaceutical powder composition, for example about: 10%, 20%, 30%, 40%, 50%, 60%, 70%, 75%, 80%, 85%, 90%, or 95%. In some instances, particles comprise a sugar alcohol that is present in an amount of about: 10-95%, 10-75%, 15-55%, 20-75%, 35-75%, or 40-75% by weight based on a weight of the particles or a pharmaceutical powder composition, for example about: 10%, 20%, 30%, 40%, 50%, 60%, 70%, 75%, 80%, 85%, 90%, or 95%. In some instances, particles comprise the pH adjusting agent that is present in an amount of about: 10-20%, 20-30%, 5-25%, 15-35%, or 5-40% by weight based on a weight of the particles or a pharmaceutical powder composition, for example about: 5%, 6%, 7%, 8%, 9%, 10%, 15%, 20%, 25%, 30%, 35%, or 40%.

In some instances, a particle or composition disclosed herein comprises a pH adjusting agent. In some instances, the pH adjusting agent is selected from the group consisting of ascorbic acid, sodium ascorbate, tartaric acid, sodium tartrate, potassium tartrate, calcium tartrate, lithium tartrate, citric acid, sodium citrate, potassium citrate, calcium citrate, lithium citrate, phosphoric acid, sodium dihydrogenphosphate, sodium monohydrogenphosphate, lithium phosphate, potassium phosphate, calcium phosphate, sodium carbonate, sodium hydrogencarbonate, lactic acid, sodium lactate, potassium lactate, calcium lactate, acetic acid, sodium acetate, potassium acetate, calcium acetate, propionic acid, sulphuric acid, sodium sulphate, potassium sulphate, boric acid, sodium borate, maleic acid, lithium maleate, sodium maleate, potassium maleate, calcium maleate, succinic acid, lithium succinate, sodium succinate, potassium succinate, calcium succinate, fumaric acid, glutamic acid, formic acid, malic acid, hydrochloric acid, nitric acid, sodium hydroxide, potassium hydroxide, triethanolamine, diisopropanolamine, ammonia solution, monoethanole amine, diethanoleamine, triethanoleamine meglumine, sodium citrate, sodium bicarbonate, potassium bicarbonate, and any combination thereof. In some instances, a pH adjusting agent disclosed herein is acetic acid; adipic acid; ammonium aluminum sulphate; ammonium bicarbonate; ammonium carbonate; ammonium citrate, dibasic; ammonium citrate, monobasic; ammonium hydroxide; ammonium phosphate, dibasic; ammonium phosphate, monobasic; calcium acetate; calcium acid pyrophosphate; calcium carbonate; calcium chloride; calcium citrate; calcium fumarate; calcium gluconate; calcium hydroxide; calcium lactate; calcium oxide; calcium phosphate, dibasic; calcium phosphate, monobasic; calcium phosphate, tribasic; calcium sulphate; carbon dioxide; citric acid; cream of tartar; fumaric acid; gluconic acid; glucono-delta-lactone; hydrochloric acid; lactic acid; magnesium carbonate; magnesium citrate; magnesium fumarate; magnesium hydroxide; magnesium oxide; magnesium phosphate; magnesium sulphate; malic acid; manganese sulphate; metatartaric acid; phosphoric acid; potassium acid tartrate; potassium aluminum sulphate; potassium bicarbonate; potassium carbonate; potassium chloride; potassium citrate; potassium fumarate; potassium hydroxide; potassium lactate; potassium phosphate, dibasic; potassium phosphate, tribasic; potassium sulphate; potassium tartrate; potassium tripolyphosphate; sodium acetate; sodium acid pyrophosphate; sodium acid tartrate; sodium aluminum phosphate; sodium aluminum sulphate; sodium bicarbonate; sodium bisulphate; sodium carbonate; sodium citrate; sodium fumarate; sodium gluconate; sodium hexametaphosphate; sodium hydroxide; sodium lactate; sodium phosphate, dibasic; sodium phosphate, monobasic; sodium phosphate, tribasic; sodium potassium hexametaphosphate; sodium potassium tartrate; sodium potassium tripolyphosphate; sodium pyrophosphate, tetrabasic; sodium tripolyphosphate; sulphuric acid; *sulphurous* acid; tartaric acid; or any combination thereof.

In some instances, a particle or composition disclosed herein comprises a sugar alcohol. In some instances, the sugar alcohol is selected from the group consisting of mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof. In some instances, the sugar alcohol has 3, 4, 5, 6, 7, 12, 18, or 24 carbons.

In some instances, compositions may further comprise a fluidizing agent. For example, the fluidizing agent is a metal salt (e.g., a calcium salt) or a phosphate salt. In some instances, the fluidizing agent is a calcium phosphate salt, e.g., tribasic calcium phosphate. The tribasic calcium phosphate can be about 0.1% to about 5.0% of the total weight of the powder composition, for example about: 0.1%-5%, 0.1%-4%, 0.1%-3%, 0.1%-2%, 0.1%-1%, 0.1%-0.5%, 0.5%-5%, 0.5%-4%, 0.5%-3%, 0.5%-2%, 0.5%-1%, 1%-5%, 1%-4%, 1%-3%, 1%-2%, 2%-5%, 2%-4%, 2%-3%, 3%-5%, 3%-4%, or 4%-5% of the total weight of the powder composition. In some instances, the tribasic calcium phosphate is about 0.5% to about 1.0% of the total weight of the powder composition. In some instances, the tribasic calcium phosphate is about 0.5% to about 1.5% of the total weight of the powder composition. In some instances, the tribasic calcium phosphate is about 0.8% of the total weight of the powder composition.

In some cases, an excipient has an average particle size of about 100 µm or less, e.g., about: 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 10 µm, 5 µm or less. In some instances, a composition herein may comprise a first excipient with an average particle diameter size of about 30 µm or less, and a second excipient with an average particle size diameter of about 30 to about 100 µm. The first excipient may have an average particle diameter size of about 30 µm or less, for example, about: 30-25 µm, 30-20 µm, 30-15 µm, 30-10 µm, 30-5 µm, 25-20 µm, 25-15 µm, 25-10 µm, 25-5 µm, 20-15 µm, 20-10 µm, 20-5 µm, 15-10 µm, 15-5 µm or 10-5 µm. In some instances, the first excipient has an average particle diameter size of about 15-30 µm. In some instances, the first excipient has an average particle diameter size of about 18-20 µm. In some instances, the first excipient has an average particle diameter size of about 20 µm. The second excipient may have an average particle diameter size of about 30 to about 100 µm, for example, about: 30-90 µm, 30-80 µm, 30-70 µm, 30-60 µm, 30-50 µm, 30-40 µm, 40-90 µm, 40-80 µm, 40-70 µm, 40-60 µm, 40-50 µm, 50-90 µm, 50-80 µm, 50-70 µm, 50-60 µm, 60-90 µm, 60-80 µm, 60-70 µm, 70-90 µm, 70-80 µm, or 80-90 µm. In some instances, the second excipient has an average particle diameter size of about 45-65 µm. In some instances, the second excipient has an average particle diameter size of about 45-55 µm. In some instances, the second excipient has an average particle diameter size of about 50-55 µm. In some instances, the second excipient has an average particle diameter size of about 50 µm. In some instances, the first excipient has an average particle diameter size of about 15 to about 30 µm and the second excipient has an average particle diameter size of about 45 to about 65 µm. In some instances, the first excipient has an average particle size of about 20 µm and the second excipient has an average particle size diameter of about 50 to about 55 µm. In some instances, the first excipient has an average particle diameter size of about 20 µm, and the second excipient has an average particle size diameter of about 50 µm. In some cases, the excipient is substantially free of particles with an average particle diameter size of about 31 to about 44 µm. In some instances, the excipient is substantially free of particles with an average particle diameter size of about 31 to about 49 µm. In some cases, substantially free of particles with an average particle diameter size means less than 15%, 10%, 5%, or 2% of all the particles fall into the given range.

In some cases, one or more excipient(s) (e.g., microcrystalline cellulose, HPMC, mannitol, TCP) may comprise at least about 5% of the total weight of the powder composition, for example, at least about: 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 98% of the total weight of the powder composition. The excipient(s) may comprise about 15% to about 99% of the total weight of the powder composition, for example, about: 15%-99%, 20%-99%, 30%-99%, 40%-99%, 50%-99%, 60%-99%, 70%-99%, 80%-99%, 90%-99%, 15%-90%, 20%-90%, 30%-90%, 40%-90%, 50%-90%, 60%-90%, 70%-90%, 80%-90%, 15%-80%, 20%-80%, 30%-80%, 40%-80%, 50%-80%, 60%-80%, 70%-80%, 15%-70%, 20%-70%, 30%-70%, 40%-70%, 50%-70%, 60%-70%, 15%-60%, 20%-60%, 30%-60%, 40%-60%, 50%-60%, 15%-50%, 20%-50%, 30%-50%, 40%-50%, 15%-40%, 20%-40%, 30%-40%, 15%-30%, 20%-30%, or 15%-20% of the total weight of the powder composition. In some instances, the first excipient comprises about 10 to about 90% of the total weight of the powder composition, for example, about: 10%-90%, 15%-90%, 20%-90%, 30%-90%, 40%-90%, 50%-90%, 60%-90%, 70%-90%, 80%-90%, 10%-80%, 15%-80%, 20%-80%, 30%-80%, 40%-80%, 50%-80%, 60%-80%, 70%-80%, 10%-70%, 15%-70%, 20%-70%, 30%-70%, 40%-70%, 50%-70%, 60%-70%, 10%-60%, 15%-60%, 20%-60%, 30%-60%, 40%-60%, 50%-60%, 10%-50%, 15%-50%, 20%-50%, 30%-50%, 40%-50%, 10%-40%, 15%-40%, 20%-40%, 30%-40%, 10%-30%, 15%-30%, 20%-30%, 10%-20%, 15%-20%, or 10%-15% of the total weight of the powder composition. In some instances, the first excipient comprises about 70% to about 90% of the total weight of the powder composition. In some instances, the first excipient comprises about 70% to about 90% of the total weight of the powder composition. In some instances, the second excipient comprises about 5% to about 15% of the total weight of the powder composition, for example, about 5%-15%, 5%-10%, or 10%-15% of the total weight of the powder composition. In some instances, the second excipient comprises about 10% of the total weight of the powder composition. For example, the first excipient comprises about 8% to about 90% of the total weight of the composition, and the second excipient comprises about 10% of the total weight of the composition. In some instances, the first excipient is about 5% to about 90% of the total weight of the powder composition, and the second excipient is about 10% of the total weight of the powder composition.

With respect to the microcrystalline cellulose component of the powder compositions presented herein, generally, acceptable microcrystalline cellulose can include microcrystalline cellulose obtained by decomposing cellulose materials such as pulp by either or both of acid and alkaline hydrolyses, then purifying the hydrolysate, and crushing or grinding it before, during, or after drying. Microcrystalline cellulose of a select average particle diameter size can be obtained, for example, via appropriate processing, e.g., via fine grinding using a high-speed rotary impact mill or air attrition mill as necessary, and size sorting. In some instances, microcrystalline cellulose components utilized as part of the microcellulose of the powder compositions presented herein can include products available under the trade names of Ceolus® PH-F20JP (e.g., average particle size about 20-23 microns, bulk density about 0.23 g/cm$^3$, repose angle not less than 60 degrees), Ceolus® PH-301 (e.g., average particle size about 50 microns, bulk density about 0.41 g/cm$^3$, repose angle about 41 degrees), Ceolus® PH-101 (e.g., average particle size about 50 microns, bulk density about 0.29 g/cm$^3$, repose angle about 45 degrees), Ceolus® PH-102 (e.g., average particle size about 90 microns, bulk density about 0.3 g/cm³, repose angle about 42 degrees), and Ceolus® PH-302 (available from Asahi Kasei Corporation, e.g., average particle size about 90 microns, bulk density about 0.43 g/cm³, repose angle about 38 degrees), and Avicel® PH-105 (e.g., average particle size about 20 microns, bulk density about 0.20-0.30 g/cm³), Avicel® PH-101 (e.g., average particle size about 50 microns, bulk density about 0.26-0.31 g/cm³), Avicel® PH-102 (e.g., average particle size about 100 microns, bulk density about 0.28-0.33 g/cm³), Avicel® PH-301 (e.g., average particle size about 50 microns, bulk density about 0.34-0.45 g/cm³), and Avicel® PH-302 (available from FMC Biopolymer Corporation, e.g., average particle size about 100 microns, bulk density about 0.35-0.46 g/cm³). In some instances, powder compositions that can be used in conjunction with the methods and compositions presented herein can comprise Ceolus® PH-F20JP and Ceolus® PH-301.

Average particle size diameters, for example, the average particle size diameters of the microcrystalline portions of the powder compositions described herein, can be determined using standard techniques, for example, via a laser-diffraction particle size distribution analyzer or via sorting methods. The average particle diameter size refers to a diameter that divides particles into two groups of equal numbers: a group with greater diameters and a group with smaller diameters. The average diameter size determined using a laser-diffraction particle size distribution analyzer corresponds to 50% volume in a determined cumulative particle size distribution curve. The average particle diameter size can, for example, be determined by a sorting method that corresponds to 50% (W/W) on a cumulative particle size distribution curve that can be obtained by sorting an appropriate amount of the particle being assessed, for an appropriate time, e.g., ten minutes, on an electromagnetic sieve shaker, using standard sieves and weighing the sample remaining on each sieve.

In some instances, the microcrystalline cellulose component of the composition comprises a first microcrystalline cellulose portion with an average particle diameter size of about 30 μm or less, and a second microcrystalline cellulose portion with an average particle size diameter of about 30-100 μm. In some instances, the first microcrystalline cellulose portion has an average particle diameter size of about 15-30 μm. In some instances, the first microcrystalline cellulose portion has an average particle diameter size of about 18-20 μm. In some instances, the first microcrystalline cellulose portion has an average particle diameter size of about 20 μm. In some instances, the second microcrystalline cellulose portion has an average particle diameter size of about 45-65 μm. In some instances, the second microcrystalline cellulose portion has an average particle diameter size of about 45-55 μm. In some instances, the second microcrystalline cellulose portion has an average particle diameter size of about 50-55 μm. In some instances, the second microcrystalline cellulose portion has an average particle diameter size of about 50 μm. In some instances, the first microcrystalline cellulose portion has an average particle diameter size of about 20 μm, and the second microcrystalline cellulose portion has an average particle size diameter of about 50 μm. In some instances, the first microcrystalline cellulose portion has an average particle diameter size of about 30 μm or less, for example, about 15-30 μm, about 18-20 μm, or about 20 μm, and the second microcrystalline cellulose portion has an average particle diameter size of about 45-65 μm, about 45-55 μm, about 50-55 μm, or about 50 μm.

In some instances, the microcrystalline cellulose component of the powder composition comprises about 10 to about 99%, e.g., about 15 to about 99%, of the total weight of the composition. In some instances, the microcrystalline cellulose component of the powder composition comprises about 53 to about 99%, about 76 to about 99%, about 76 to about 97%, about 90 to about 97%, or about 90 to about 95% of the total weight of the composition. In some instances, the microcrystalline cellulose component of the powder composition comprises about 10 to about 98%, about 18 to about 98%, about 18 to about 91%, about 67 to about 91%, or about 67 to about 83%. In some instances, the microcrystalline cellulose component of the powder composition comprises about 53%, about 76%, about 90%, about 95%, about 97%, or about 99% of the total weight of the composition. In some instances, the microcrystalline cellulose component of the powder composition comprises about 10%, about 18%, about 66%, about 83%, about 91%, or about 98% of the total weight of the composition. In some instances, the first microcrystalline cellulose portion comprises about 3.0 to about 90%, e.g., about 8.0 to about 90%, of the total weight of the composition, and the second microcrystalline cellulose portion comprises about 10% of the total weight of the composition. In some instances, the first microcrystalline cellulose portion comprises about 43 to about 89%, about 66 to about 89%, about 66 to about 87%, about 80 to about 87%, or about 80 to about 85% of the total weight of the composition, of the total weight of the composition, and the second microcrystalline cellulose portion comprises about 10% of the total weight of the composition. In some instances, the microcrystalline cellulose component of the powder composition comprises about 1 to about 88%, about 8 to about 88%, about 8 to about 81%, about 57 to about 81%, or about 57 to about 83%, and the second microcrystalline cellulose portion comprises about 10% of the total weight of the composition. In some instances, the microcrystalline cellulose component of the powder composition comprises about 43%, about 66%, about 80%, about 85%, about 87%, or about 89% of the total weight of the composition, and the second microcrystalline cellulose portion comprises about 10% of the total weight of the composition. In some instances, the microcrystalline cellulose component of the powder composition comprises about 1%, about 8%, about 57%, about 73%, about 81%, or about 88% of the total weight of the composition, and the second microcrystalline cellulose portion comprises about 10% of the total weight of the composition.

With respect to tribasic calcium phosphate (also known as hydroxyapatite), any pharmaceutically acceptable tribasic calcium phosphate can be used in conjunction with the methods and compositions presented herein. In some instances, the tribasic calcium phosphate utilized has an average particle diameter of about 10-100 μm, for example, about 10-75 μm, about 10-50 μm, about 10-30 μm, or about 10 μm. In some instances, not less than 90% of the tribasic calcium phosphate particles in the powder compositions presented herein have a diameter less than 150 μm, and not more than 5% of the particles in the powder composition have a diameter less than 10 μm. In some instances, the overall average particle size of the tribasic calcium phosphate particles in the powder compositions presented herein about 15 to about 30 μm, about 18 to about 25 μm, about 18 to about 20 μm, or about 20 μm.

In some instances, greater than or equal to about 90% of the tribasic calcium phosphate particles have a diameter less than 150 μm. In some instances, the overall average particle size of the tribasic calcium phosphate particles is about 15 to about 30 μm, about 18 to about 25 μm, about 18 to about 20 μm, or about 20 μm. In some instances, less than or equal to about 5% of the tribasic calcium phosphate particles have a diameter less than 10 μm. In some instances, for the tribasic calcium phosphate particles, greater than or equal to about 90% of the particles have a diameter less than 150 μm; and the overall average particle size is about 15 to about 30 μm, about 18 to about 25 μm, about 18 to about 20 μm, or about 20 μm; and less than or equal to about 5% of the particles have a diameter less than 10 μm.

In some instances, tribasic calcium phosphate comprises at least: about 0.1%, about 0.2%, about 0.3%, about 0.4%, about 0.5%, about 0.6%, about 0.7%, about 0.8%, about 0.9%, about 1%, about 1.5%, 2.0%, for example, 0.5-1.0% of the total weight of the composition. In specific instances of the methods of treating headache, including migraine, the tribasic calcium phosphate comprises about 0.8% of the total weight of the composition.

Doses

In some cases, a total dose of a powder composition administered can be at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, or 50 mg. The total dose of the powder composition administered can be about 0.1 to about 50 mg, for example, about 0.1-50.0 mg, about 0.1-25.0 mg, about 0.1-20.0 mg, about 0.1-15.0 mg, about 0.1-10.0 mg, about 0.1-5.0 mg, about 0.1-2.0 mg, about 0.1-1.0 mg, about 0.1-0.5 mg, about 0.2-50.0 mg, about 0.2-25.0 mg, about 0.2-20.0 mg, about 0.2-15.0 mg, about 0.2-10.0 mg, about 0.2-5.0 mg, about 0.2-2.0 mg, about 0.2-1.0 mg, about 0.2-0.5 mg, about 0.5-55.0 mg, 0.5-25.0 mg, about 0.5-20.0 mg, about 0.5-15.0 mg, about 0.5-10.0 mg, about 0.5-5.0 mg, about 0.5-2.0 mg, about 0.5-1.0 mg, about 1.0-25.0 mg, about 1.0-50.0 mg, about 1.0-20.0 mg, about 1.0-15.0 mg, about 1.0-10.0 mg, about 1.0-5.0 mg, about 1.0-2.0 mg, about 2.0-50.0 mg, about 2.0-25.0 mg, about 2.0-20.0 mg, about 2.0-15.0 mg, about 2.0-10.0 mg, about 2.0-5.0 mg, about 5.0-25.0 mg, about 5.0-20.0 mg, about 5.0-15.0 mg, about 5.0-10.0 mg, about 10.0-50.0 mg, about 0.5-25.0 mg, about 10.0-20.0 mg, about 10.0-15.0 mg, about 15.0-25.0 mg, or about 15.0-20.0 mg. For example, the total dose of the powder composition administered is about 25 mg.

In some cases, a powder composition comprises a total dose of an active agent administered of at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg. The powder composition may comprise a total dose of an active agent administered at about 0.1 to about 10.0 mg, for example, about 0.1-10.0 mg, about 0.1-9.0 mg, about 0.1-8.0 mg, about 0.1-7.0 mg, about 0.1-6.0 mg, about 0.1-5.0 mg, about 0.1-4.0 mg, about 0.1-3.0 mg, about 0.1-2.0 mg, about 0.1-1.0 mg, about 0.1-0.5 mg, about 0.2-10.0 mg, about 0.2-9.0 mg, about 0.2-8.0 mg, about 0.2-7.0 mg, about 0.2-6.0 mg, about 0.2-5.0 mg, about 0.2-4.0 mg, about 0.2-3.0 mg, about 0.2-2.0 mg, about 0.2-1.0 mg, about 0.2-0.5 mg, about 0.5-10.0 mg, about 0.5-9.0 mg, about 0.5-8.0 mg, about 0.5-7.0 mg, about 0.5-6.0 mg, about 0.5-5.0 mg, about 0.5-4.0 mg, about 0.5-3.0 mg, about 0.5-2.0 mg, about 0.5-1.0 mg, about 1.0-10.0 mg, about 1.0-5.0 mg, about 1.0-4.0 mg, about 1.0-3.0 mg, about 1.0-2.0 mg, about 2.0-10.0 mg, about 2.0-9.0 mg, about 2.0-8.0 mg, about 2.0-7.0 mg, about 2.0-6.0 mg, about 2.0-5.0 mg, about 2.0-4.0 mg, about 2.0-3.0 mg, about 5.0-10.0 mg, about 5.0-9.0 mg, about 5.0-8.0 mg, about 5.0-7.0 mg, about 5.0-6.0 mg, about 6.0-10.0 mg, about 6.0-9.0 mg, about 6.0-8.0 mg, about 6.0-7.0 mg, about 7.0-10.0 mg, about 7.0-9.0 mg, about 7.0-8.0 mg, about 8.0-10.0 mg, about 8.0-9.0 mg, or about 9.0-10.0 mg. For example, the total dose administered at about 0.5 mg. In some instances, the total dose administered is about 0.1-5 mg. In some instances, the total amount administered is about 0.5-5 mg. In some instances, the total amount administered is about 0.5-3 mg. In some instances, the total amount of administered is about 1-2 mg.

Methods of Making Compositions

The present disclosure also provides methods for making compositions disclosed herein, including spray-drying, freeze-drying, and melt-extruding.

In some cases, the present disclosure provides for a method of making an intranasal pharmaceutical powder composition, comprising spray drying/freeze-drying/melt-extruding an active agent and at least one member selected from the group consisting of a thickening agent, a carrier, a pH adjusting agent, a sugar alcohol, and any combination thereof, to produce particles, wherein: the particles comprise the active agent; at least about 20 percent by weight of the active agent in the particles is amorphous as determined by X-ray diffraction; when the active agent has a crystalline form, a solubility of the active agent in a crystalline form in an aqueous liquid ranges from about 0.1 μg/mL to about 1 mg/mL in water at a temperature of 37±0.5° C.; and the particles have an average particle size of about 10 microns to about 300 microns, as measured by laser diffraction. In some instances, the particles comprise the active agent and the thickening agent. In some instances, the particles comprise the active agent and the carrier. In some instances, the particles comprise the active agent, the carrier, and the thickening agent. In some instances, the method further comprises blending the particles with an additional amount of the carrier. In some instances, the method further comprises blending the particles with an additional carrier, additional thickening agent, or any combination thereof. In some instances, the particles comprise the active agent and are free from the thickening agent, the carrier, or a combination thereof. In some instances, the solubility is measured at a pH ranging from about 6.8 to about 7.4. In some instances, the particles comprise the carrier that is at least partially water insoluble at 37±0.5° C. In some instances, the water insolubility is measured at a pH ranging from about 6.8 to about 7.4. In some instances, the particles further comprise the thickening agent, and wherein the carrier has lower water solubility than that of the thickening agent. In some instances, the particles comprise the carrier that is at least partially adhesive to mucus. In some instances, the particles comprise the carrier that comprises an oligosaccharide, a polysaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, β cyclodextrin, or any combination thereof. In some instances, the particles have an average particle size of from about 15 to about 100 μm, as measured by laser diffraction. In some instances, the carrier has an average particle size of about 20 to about 50 μm, as measured by laser diffraction. In some instances, the particles comprise the thickening agent that is at least partially water soluble 37±0.5° C. In some instances, the water solubility is measured at a pH ranging from about 6.8 to about 7.4. In some instances, the particles further comprise the carrier, and wherein the thickening agent has higher water solubility than that of the carrier. In some instances, the particles comprise the thickening agent that binds to the active agent. In some instances, the particles further comprise the carrier, and wherein the thickening agent binds to the active agent and the carrier. In some instances, the particles comprise thickening agent that comprises a polysaccharide. In some instances, the thickening agent comprises hydroxypropyl methylcellulose (HPMC), HPMC acetate succinate, hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 μm, as measured by laser diffraction. In some instances, the particles have an average particle size of about 15 μm, as measured by laser diffraction. In some instances, the particles comprise the thickening agent and the carrier and have an average particle size of from about 10 to about 50 μm, as measured by laser diffraction. In some instances, the particles an average particle size of about 20 μm, as measured by laser diffraction.

In some cases, provided herein is a method for generating a composition, comprising spray-drying/freeze-drying/melt-extruding an active agent, optionally with a water insoluble polysaccharide muco-adhesive carrier (e.g., MCC), a sugar alcohol such as mannitol, and/or a water soluble polysaccharide viscosity increasing agent (e.g., HPMC). In some instances, the active agent is produced by grinding, evaporation, spray coating, or freeze-drying. In some instances, the method of making further comprises physically blending the active agent with additional muco-adhesive carrier (e.g., MCC) and/or a fluidizer (e.g., tribasic calcium phosphate). In some instances, provided herein are methods of manufacturing the spray dried particle (SDRP) with an active agent and muco-adhesive carrier (e.g., MCC), without viscosity increasing agent (e.g., HPMC). In some instances, provided herein are methods of manufacturing spray dried particles (SDRP) with an active agent and a viscosity increasing agent (e.g., HPMC), without a muco-adhesive carrier (e.g., MCC). In some instances, provided herein are methods of manufacturing spray dried particles (SDRP) with an active agent only, without a muco-adhesive carrier (e.g., MCC) or a viscosity increasing agent (e.g., HPMC).

A powder composition described herein can be made using standard techniques.

For example, the components of the powder compositions can be mixed while applying a shearing force, e.g., via a high shear mixer/stirrer. Alternatively, for example, the components of the powder compositions can be homogeneously mixed using, e.g., a mortar or V-blender.

A powder composition described herein can be intranasally administered utilizing any techniques known in the art. For example, the compositions can be administered utilizing a dispenser, for example a single use dispenser or a multi-use dispenser. In some instances, the powder compositions are administered using a device such as, for example, a device as described in US 2011/0045088 or in WO 2012/105236, each of which is incorporated herein by reference for its disclosure of devices that can be utilized to intranasally administer powder compositions to a primate, for example, to a human. In some instances, the device used to administer the powder composition is a Fit-lizer™ (SNBL, LTD) intranasal dispenser device.

In some instances, a powder composition presented herein is encapsulated prior to administration. For example, the powder compositions presented herein can be encapsulated in unit dose form. In some instances, the encapsulated powder compositions are released from the capsule prior to administration. In some instances, the powder compositions are released from the capsule upon administration. Powder compositions can, for example, be intranasally administered utilizing devices designed to accept and deliver powder compositions that have been encapsulated. In some instances, the fill weight of the capsule comprises an appropriate excess amount of the powder composition such that the desired dose is administered, taking into account a select administration device being utilized.

Methods of Use

In some cases, routes of administration of a pharmaceutical composition disclosed herein include nasal, pulmonary, buccal, or sublingual administration.

In some instances, the present disclosure provides for a method, comprising intranasally administering to a subject a pharmaceutical powder composition comprising particles that comprise an active agent and at least one member selected from the group consisting of a thickening agent, a carrier, a pH adjusting agent, a sugar alcohol, and any combination thereof, wherein at least about 20 percent by weight of the active agent in the particles is amorphous as determined by X-ray diffraction; when the active agent has a crystalline form, a solubility of the active agent in a crystalline form ranges from about 0.1 μg/mL to about 1 mg/mL in water at a temperature of 37±0.5° C. at a pH ranging from about 6.8 to about 7.4; the particles have an average particle size of about 10 microns to about 300 microns, as measured by laser diffraction; and the administration of the pharmaceutical powder composition improves a pharmacokinetic parameter of the active agent by at least about 15%, when compared to administration of a corresponding composition that comprises the active agent in a crystalline form. In some instances, the pharmaceutical powder composition further comprises particles that comprise the active agent and are free from the thickening agent, the carrier, or a combination thereof.

In some instances, a composition (e.g., an intranasal pharmaceutical powder composition) or a method disclosed herein is used in the treatment or prevention of a disease or a condition in the human subject. In some instances, the disease or condition is pain, hormone disorder, a headache, amyotrophic lateral sclerosis, Parkinson's disease, stress, anxiety, nausea, emesis, aggression, pain, neuropathic pain, sleeplessness, insomnia, restless leg syndrome, depression, or any combination thereof. In some instances, the disease or condition is a headache. In some instances, the headache is a migraine headache, a cluster headache, a hemicrania continua headache, a chronic headache, a tension headache, a chronic tension headache, or any combination thereof. In some instances, the headache is a migraine headache. In some instances, the headache is a migraine headache with aura. In some instances, the headache is a migraine headache without aura. In some instances, the headache is moderate to severe. In some instances, the headache is acute. In some instances, the pharmaceutical powder composition is administered for at least one day, two days, three days, four days, five days, six days, one week, one month, or one year. In some instances, the administration of the pharmaceutical powder composition is 1 time, 2 times, 3 times, 4 times, 5 times, 6 times, 7 times, or 8 times daily. In some instances, the pharmaceutical powder composition is in a single unit dose. In some instances, the pharmaceutical powder composition is a unit dose of from about 5 mg to about 50 mg. In some instances, a unit dosage of the pharmaceutical powder composition contains about 0.1 mg to about 25 mg of the active agent. In some instances, the subject is a primate. In some instances, the subject is a human. In some instances, the subject is a monkey.

In some instances, provided herein is a method of treating a disease or a condition, including pain, headache, or hormone disorder, comprising administering intranasally (e.g., through a nasal cavity) a powder compositions comprising an active agent. Other possible mucosal routes of administration include conjunctival administration, buccal administration, and sublingual administration. Buccal and sublingual have the advantage of being user friendly and non-invasive, and can be self-administered. Another alternative route to oral is transdermal, delivery of active agents through the patient's skin. The last form of administration is intradermal injection (administration to the dermis) and subcutaneous injection (administration to the fat layer below the skin). In some instances, the powder composition comprises an active agent, microcrystalline cellulose with an average particle diameter size of about 100 μm or less, and tribasic calcium phosphate. In some instaces, the powder composition comprises an active agent, a microcrystalline cellulose portion with an average particle size diameter of about 50-55 μm, e.g., about 50 μm, comprising about 10% of the total weight of the powder composition, a microcrystalline cellulose portion with an average particle size of about 20 μm comprising about 3 to about 90%, e.g., about 8 to about 90%, of the total weight of the powder composition and, optionally, a fluidizing agent. In some instances, the powder compositions utilized as part of the methods further comprise an active agent disclosed herein, e.g. caffeine, for example, anhydrous caffeine.

In some instances, the headache treated by the methods provided herein is a cluster headache, chronic daily headache, or migraine, including adult migraine or pediatric migraine. The migraine can be migraine with aura or migraine without aura. In some instances, the methods presented herein are methods for acute treatment of a human having a migraine with or without aura. In some instances, the methods presented herein are methods for chronic treatment of migraine with or without aura.

"Treating," or "Treatment" as used with a method disclosed herein, refers to the amelioration, reduction, or elimination of at least one symptom of the disorder being treated. In some instances, the methods of treating headache or pain ameliorate, reduce, or eliminate at least one or more symptoms. Symptoms of headache, e.g., cluster headache, chronic daily headache or migraine, may include pain. Symptoms can also include, for example, nausea, vomiting, photophobia, phonophobia, osmophobia (aversion to, or hypersensitivity to, odors), vertigo, and/or allodynia. The symptom or symptoms can, for example, be evaluated via a four point severity scale as follows: 0=none 1=mild symptom, not interfering with normal daily activities 2=moderate symptom, causing some restriction to normal activities 3=severe, leading to inability to perform normal daily activities. Alternatively, or additionally, a symptom or symptoms, including the four listed above, can be evaluated via a four-point functional disability scale that assesses the level of impairment a symptom has on a patient's ability to perform usual daily activities, as follows: 0=not at all impaired 1=slightly impaired 2=moderately impaired 3=severely or completely impaired. See Cephalalgia 1991; 11:1-12. In some instances, the headache or pain has a severity of more than about any of 1, 2, 3, 4, 5, 6, 7, 8, 9, or 10 on a scale of 0 to 10. In some instances, the intensity of headache or pain, for example, pain associated with migraine, can be measured according to a 4-point severity scale (0=no pain, 1=mild, 2=moderate, 3=severe). In some instances, the methods of treating headache, for example migraine, presented herein reduce the severity of headache pain, for example pain associated with migraine, by at least one point on such a 4-point severity scale.

In some instances, the methods of treating a disease or condition can ameliorate, reduce, or eliminate at least one symptom within 10 minutes, 15 minutes, 20 minutes, 25 minutes, 30 minutes, 45 minutes, 1 hour, 1.5 hours, 2 hours, 2.5 hours, 3 hours, or 4 hours of intranasally administering a powder composition presented herein. In some instances, the amelioration, reduction, or elimination of at least one symptom is sustained for about 3 hours, 4 hours, 5 hours, 6 hours, 8 hours, 12 hours, 18 hours, 36 hours, or 48 hours.

In some instances, presented herein is a method comprising: intranasally administering to a subject a powder composition comprising: a) an active agent, wherein the total dose of an active agent being administered is about 0.1-10.0 mg; b) a microcrystalline cellulose component with an average particle size diameter of about 100 μm or less; and c) tribasic calcium phosphate. Herein, unless otherwise noted, "the total dose of DHE being administered" and like phrasing means the total amount of parent DHE in the DHE form, e.g., amount of DHE free base in a pharmaceutically acceptable DHE salt, being administered. In some instances, the powder composition comprises DHE mesylate, and the total amount of DHE free base of the DHE mesylate being administered is about 0.1-10.0 mg. In some instances, the powder composition is administered to a single nostril of the subject. In some instances, a portion of the powder composition is administered to each nostril of the subject. For example, in some instances of the method, about half of the powder composition is administered to one nostril and about half of the powder composition is administered to the other nostril of the subject.

In some instances, for treating a disease or condition, a total amount of the powder composition administered is about: 5 mg, 10 mg, 15 mg, 20 mg, 25 mg, 30 mg, 35 mg, 40 mg, 45 mg, or 50 mg, into a single or both nostrils. In some instances, the total amount of the powder composition is administered into a single nostril. In some instances, a portion of the total amount of the powder composition is administered into each nostril. In some instances, about half of the total amount of the powder composition is administered into one nostril and the remaining half is administered into the other nostril.

In some instances, a total dose of an active agent administered is about 0.1-6.0 mg. In some instances, the total dose of an active agent administered is about 0.5-6.0 mg. In some instances, the total dose of an active agent administered is about 1.0-6.0 mg. In some instances, the total dose of an active agent administered is about 2.0-4.0 mg. In some instances, the total dose of an active agent administered is about 0.1 mg, about 0.5 mg, about 1.0 mg, about 1.5 mg, about 2.0 mg, about 3.0 mg, about 4.0 mg, about 5.0 mg, about 7.5 mg, or about 10.0 mg. In some instances, the total dose is administered into a single nostril. In some instances, a portion of the total dose is administered into each nostril. In some instances, about half of the total dose is administered into one nostril and the remaining half is administered into the other nostril.

In some instances, the methods of treating headache, including migraine, comprise administering the powder composition such that the mean $T_{max}$ of an active agent is about 10-50 minutes. In some instances, the mean $T_{max}$ of an active agent is about 10-30 minutes. In some instances, the mean $T_{max}$ of an active agent is about 5-50 minutes. In some instances, the mean $T_{max}$ of an active agent is about 5-30 minutes. In some instances, the mean $T_{max}$ of an active agent is about 2-50 minutes. In some instances, the mean $T_{max}$ of an active agent is about 2-30 minutes. In some instances, the methods of treating headache, including migraine, comprise administering the powder composition such that the mean $C_{max}$ of an active agent is about 0.5-100 ng/mL. In some instances, such methods of treating headache, including migraine, utilizing about 0.1-6.0 mg an active agent comprise administering the powder composition such that the mean $AUC_{0-inf}$ of an active agent is about 1-500 ng·h/mL. In some instances, the mean $AUC_{0-30\ min}$ of an active agent is about 1-500 ng·h/mL. In some instances, the methods of treating headache, including migraine, comprise administering the subject variability in an active agent $C_{max}$ is less than 30%.

In some instances, presented herein is a method of treating headache, including migraine, comprising: intranasally administering to a human having a headache, e.g., migraine, a powder composition comprising: a) an active agent, or a pharmaceutically acceptable salt thereof, wherein the total dose of an active agent being administered is about 0.1-6.0 mg; b) a microcrystalline cellulose component comprising a first microcrystalline cellulose portion with an average particle size of about 30 µm or less, for example, about 15-30 µm, about 18-20 µm, or about 20 µm, and a second microcrystalline cellulose portion with an average particle size diameter of about 45-65 µm, about 45-55 µm, about 50-55 µm, or about 50 µm, wherein the first microcrystalline cellulose portion comprises about 45 to about 90%, e.g., about 50 to about 90%, of the total weight of the composition, and the second microcrystalline portion comprises about 10% of the total weight of the composition; and c) tribasic calcium phosphate comprising about 0.5-1.0%, e.g., about 0.8%, of the total weight of the composition. In some instances, the powder composition is administered to a single nostril of the human having a headache, e.g., migraine. In some instances, a portion of the powder composition is administered to each nostril of the human having a headache. In some instances, about half of the powder composition is administered to one nostril and about half of the powder composition is administered to the other nostril of the human having a headache.

In some instances, for treating a headache for a condition or disease, for example pain, migraine headache, or hormone disorder, the powder composition further comprises an active agent disclosed herein, e.g., caffeine, for example, anhydrous caffeine, for example, about 1-25% of the active agent.

In some instances, for treating a headache for a condition or disease, a powder composition comprises about 0.1-6.0 mg of an active agent, and is administered such that the mean $T_{max}$ of an active agent is about 10-50 minutes. In some instances, the powder composition is administered such that the mean $T_{max}$ of an active agent is about 2-50 minutes. In some instances, the powder composition is administered such that the mean $T_{max}$ of an active agent is about 2-30 minutes. In some instances, the powder composition is administered such that the mean $C_{max}$ of an active agent is about 0.5-40 ng/mL. In some instances, the powder composition is administered such that the mean $AUC_{0-inf}$ of an active agent is about 1-200 ng·h/mL. In some instances, the powder composition is administered such that the mean $T_{1/2}$ of an active agent is about 100-300 minutes. In some instances, the subject variability in an active agent $C_{max}$ is less than 30%.

In some instances, presented herein is a method comprising: intranasally administering to a human in need thereof, a powder composition comprising: a) an active agent; b) an excipient component comprising a first excipient portion with an average particle size of about 30 µm or less, for example, about 15-30 µm, about 18-20 µm, or about 20 µm, and a second excipient portion with an average particle size diameter of about 45-65 µm, for example, about 45-55 µm or about 50-55 µm, e.g., about 50 µm, wherein the first excipient portion comprises about 80 to about 90%, e.g., about 85 to about 90%, of the total weight of the composition, and the second excipient portion comprises about 10% of the total weight of the composition; and c) fluidizing agent (e.g. tribasic calcium phosphate) comprising about 0.5-1.0%, e.g., about 0.8%, of the total weight of the composition. In some instances, the powder composition further comprises caffeine, for example, about 1-2% of an active agent disclosed herein, e.g. caffeine, for example, anhydrous caffeine.

In some instances, presented herein is a method of treating headache, including migraine, comprising: intranasally administering to a human in need thereof, a powder composition comprising: a) an active agent (e.g., DHE or a salt thereof, DHE mesylate), wherein the total dose of an active agent being administered is about 2.0 mg; b) a microcrystalline cellulose component comprising a first microcrystalline cellulose portion with an average particle size of about 30 µm or less, for example, about 15-30 µm, about 18-20 µm, or about 20 µm, and a second microcrystalline cellulose portion with an average particle size diameter of about 45-65 µm, for example, about 45-55 µm or about 50-55 µm, e.g., about 50 µm, wherein the first microcrystalline cellulose portion comprises about 75 to about 90%, e.g., about 80 to about 90%, of the total weight of the composition, and the second microcrystalline portion comprises about 10% of the total weight of the composition; and c) tribasic calcium phosphate comprising about 0.5-1.0%, e.g., about 0.8%, of the total weight of the composition. In some instances, the powder composition further comprises a thickening agent, for example HPMC, which can be present in about 0.1-5% of a total weight. In some instances, the powder composition further comprises a pH adjuster, for example ascorbic acid, which can be present in about 0.5-5% of a total weight. In some instances, the powder composition further comprises a sugar alcohol, for example mannitol, which can be present in about 10-95.0% of a total weight. In some instances, the powder composition further comprises an active agent, for example, about 5-10% of caffeine, e.g., anhydrous caffeine.

In some instances, of such methods of treating headache, including migraine, the powder composition further comprises a fluidizing agent. Fluidizing agents include but are not limited to tribasic calcium phosphate, hydrous silicon dioxide, light anhydrous silicic acid, crystalline cellulose, synthetic aluminum silicate, calcium silicate, titanium oxide, stearic acid, calcium stearate, magnesium stearate, talc, cornstarch, magnesium metasilicate aluminate, anhydrous calcium hydrogenphosphate, synthetic hydrotalcite, and magnesium metasilicate aluminate. In some instances, the fluidizing agent is tribasic calcium phosphate. In some instances, the tribasic calcium phosphate comprises about 0.5-1.0% of the total weight of the composition. In specific instances of the methods of treating migraine, the tribasic calcium phosphate comprises about 0.8% of the total weight of the composition.

In some instances, the powder compositions utilized as part of such methods of treating headache, including migraine, further comprises an active agent disclosed herein, e.g. caffeine, for example, anhydrous caffeine. In some instances, the powder compositions utilized as part of the methods of treating migraine comprise about 1-60% of an active agent.

In some cases, presented herein is a powder composition comprising one or more of an active agent (e.g., DHE, indomethacin, testosterone); a microcrystalline cellulose component (e.g., CEOLUS PH-F20JP, about 20-23 microns in particle size, or a mixture of CEOLUS PH-F20JP and CEOLUS PH-301); a thickening agent (e.g., HPMC); d) a sugar alcohol (e.g., mannitol, about 53-300 microns in particle size); a pH adjuster (e.g., ascorbic acid), a fluidizing agent (e.g., tribasic calcium phosphate); and, optionally an additional active agent disclosed herein, e.g. caffeine, for example, anhydrous caffeine. Examples of the powder composition are presented below in Table 1.

In some instances, the powder composition is prepared by fluid bed granulation of all its components. In some instances, the pharmaceutical powder composition comprises an active agent, a thickening agent, a carrier, and a sugar alcohol. In some instances, the active agent is amorphous, e.g., at least 20% amorphous. In some instances, the active agent is spray dried, e.g., with the thickening agent. In some instances, the thickening agent is a binder of low viscosity grade, e.g., HPMC. In some instances, the sugar alcohol is mannitol. In some instances, the sugar alcohol has a particle size diameter of about 53 to about 300 microns. In some instances, all components are aggregated together enough to withstand delivery from device and ensure deposition in same location. In some instances, the aggregation is loose enough for immediate break-up to individual components upon deposition on mucosa. In some instances, the particle size diameter of the powder composition is about 50 microns to about 150 microns, e.g., about 150 microns. In some instances, the powder composition has an angle of repose less than 55°, e.g., less than: 50°, 45°, 40°, 35°, 30°, or 25°. In some instances, the powder composition is free from a fluidizing agent.

TABLE 1

| Weight (mg) | w/w % of total powder composition | | | | |
|---|---|---|---|---|---|
| | MCC | HPMC | Mannitol | TCP | Ascorbic acid |
| | | | | | Active agent |
| 0.1-10 | 5-98 | 0.1-3 | 0 | 0.5-1.5 | 0 |
| 0.1-2 | 75-94 | 0.1-3 | 0 | 0.5-1.5 | 0 |
| 1-5 | 60-90 | 0.1-3 | 0 | 0.5-1.5 | 0 |
| 1-2 | 74-90 | 0.1-3 | 0 | 0.5-1.5 | 0 |
| 0.1 | 73-94 | 0.1-3 | 0 | 0.5-1.5 | 0 |
| 0.5 | 76-92 | 0.1-3 | 0 | 0.5-1.5 | 0 |
| 1.0 | 74-90 | 0.1-3 | 0 | 0.5-1.5 | 0 |
| 2.0 | 69-85 | 0.1-3 | 0 | 0.5-1.5 | 0 |
| 4.0 | 55-71 | 0.1-3 | 0 | 0.5-1.5 | 0 |
| 6.0 | 41-57 | 0.1-3 | 0 | 0.5-1.5 | 0 |
| 10.0 | 32-48 | 0.1-3 | 0 | 0.5-1.5 | 0 |
| 0.1-10 | 5-50 | 0.1-3 | 10-95 | 0.5-1.5 | 0 |
| 0.1-2 | 5-50 | 0.1-3 | 20-60 | 0.5-1.5 | 0 |
| 1-5 | 5-50 | 0.1-3 | 30-50 | 0.5-1.5 | 0 |
| 1-2 | 5-50 | 0.1-3 | 10-30 | 0.5-1.5 | 0 |
| 0.1 | 5-50 | 0.1-3 | 50-95 | 0.5-1.5 | 0 |
| 0.5 | 5-50 | 0.1-3 | 10-95 | 0.5-1.5 | 0 |
| 1.0 | 5-50 | 0.1-3 | 20-60 | 0.5-1.5 | 0 |
| 2.0 | 5-50 | 0.1-3 | 30-50 | 0.5-1.5 | 0 |
| 4.0 | 5-50 | 0.1-3 | 10-30 | 0.5-1.5 | 0 |
| 6.0 | 5-50 | 0.1-3 | 50-95 | 0.5-1.5 | 0 |
| 10.0 | 5-50 | 0.1-3 | 10-95 | 0.5-1.5 | 0 |
| 0.1-10 | 5-50 | 0.1-3 | 5-50 | 0.5-1.5 | 0.1-30 |
| 0.1-2 | 5-50 | 0.1-3 | 5-50 | 0.5-1.5 | 0.1-30 |
| 1-5 | 5-50 | 0.1-3 | 5-50 | 0.5-1.5 | 0.1-30 |
| 1-2 | 5-50 | 0.1-3 | 5-50 | 0.5-1.5 | 0.1-30 |
| 0.1 | 5-50 | 0.1-3 | 5-50 | 0.5-1.5 | 0.1-30 |
| 0.5 | 5-50 | 0.1-3 | 5-50 | 0.5-1.5 | 0.1-30 |
| 1.0 | 5-50 | 0.1-3 | 5-50 | 0.5-1.5 | 0.1-30 |
| 2.0 | 5-50 | 0.1-3 | 5-50 | 0.5-1.5 | 0.1-30 |
| 5.0 | 5-50 | 0.1-3 | 5-50 | 0.5-1.5 | 0.1-30 |
| 8.0 | 5-50 | 0.1-3 | 5-50 | 0.5-1.5 | 0.1-30 |
| 10.0 | 5-50 | 0.1-3 | 5-50 | 0.5-1.5 | 0.1-30 |
| 0.1-10 | 4-89 | 0 | 0 | 0 | 0 |
| 0.1-2 | 57-99 | 0 | 0 | 0 | 0 |
| 1-5 | 95-99 | 0 | 0 | 0 | 0 |
| 1-2 | 98-99 | 0 | 0 | 0 | 0 |
| 0.1 | 99 | 0 | 0 | 0 | 0 |
| 0.5 | 95 | 0 | 0 | 0 | 0 |
| 1.0 | 99 | 0 | 0 | 0 | 0 |
| 2.0 | 98 | 0 | 0 | 0 | 0 |
| 5.0 | 95 | 0 | 0 | 0 | 0 |
| 8.0 | 98 | 0 | 0 | 0 | 0 |
| 10.0 | 90 | 0 | 0 | 0 | 0 |
| 0.1-10 | 0 | 0.1-15 | 0 | 0 | 0 |
| 0.1-2 | 0 | 0.1-15 | 0 | 0 | 0 |
| 1-5 | 0 | 0.1-15 | 0 | 0 | 0 |
| 1-2 | 0 | 0.1-15 | 0 | 0 | 0 |
| 0.1 | 0 | 0.1-15 | 0 | 0 | 0 |
| 0.5 | 0 | 0.1-15 | 0 | 0 | 0 |
| 1.0 | 0 | 0.1-15 | 0 | 0 | 0 |
| 2.0 | 0 | 0.1-15 | 0 | 0 | 0 |
| 5.0 | 0 | 0.1-15 | 0 | 0 | 0 |
| 8.0 | 0 | 0.1-15 | 0 | 0 | 0 |
| 10.0 | 0 | 0.1-15 | 0 | 0 | 0 |
| 0.1-10 | 4-89 | 5-15 | 0 | 0.8 | 1-58 |
| 0.1-2 | 57-88 | 5-15 | 0 | 0.8 | 1-23 |
| 1-5 | 8-57 | 5-15 | 0 | 0.8 | 12-58 |
| 1-2 | 57-73 | 5-15 | 0 | 0.8 | 12-23 |
| 0.1 | 76-93.5 | 5-15 | 0 | 0.8 | 0.5-2 |
| 0.5 | 66-89.5 | 5-15 | 0 | 0.8 | 2.5-10 |
| 1.0 | 54-85 | 5-15 | 0 | 0.8 | 5-20 |
| 2.0 | 29-75 | 5-15 | 0 | 0.8 | 10-40 |
| 5.0 | 1-46 | 5-15 | 0 | 0.8 | 25-59 |
| 8.0 | 0.3-32 | 5-15 | 0 | 0.8 | 25-56 |
| 10.0 | 0.1-12 | 5-15 | 0 | 0.8 | 25-47 |
| 0.1-10 | 5-50 | 0.1-3 | 5-50 | 0 | 0 |
| 0.1-2 | 5-50 | 0.1-3 | 5-50 | 0 | 0 |
| 1-5 | 5-50 | 0.1-3 | 5-50 | 0 | 0 |
| 1-2 | 5-50 | 0.1-3 | 5-50 | 0 | 0 |
| 0.1 | 5-50 | 0.1-3 | 5-50 | 0 | 0 |
| 0.5 | 5-50 | 0.1-3 | 5-50 | 0 | 0 |
| 1.0 | 5-50 | 0.1-3 | 5-50 | 0 | 0 |
| 2.0 | 5-50 | 0.1-3 | 5-50 | 0 | 0 |
| 5.0 | 5-50 | 0.1-3 | 5-50 | 0 | 0 |
| 8.0 | 5-50 | 0.1-3 | 5-50 | 0 | 0 |
| 10.0 | 5-50 | 0.1-3 | 5-50 | 0 | 0 |
| 4 | 50 | 5 | 25 | 0 | 0 |
| 4 | 55 | 0 | 25 | 0 | 0 |
| 1 | 94.2 | 0 | 0 | 0.8 | 0 |
| 2 | 79.2 | 0 | 0 | 0.8 | 0 |

EXAMPLES

Example 1: Preparation of DHE Powder Compositions

The content and amount of ingredients of DHE compositions are shown in Table 2.

TABLE 2

Intranasal DHE Compositions

| Preparations | DHE/Formulation (mg/mg) | DHE | MCC-1 for SD | HPMC for SD | MCC-1 | Mannitol (mg) | pH Adjuster | MCC-2 | TCP |
|---|---|---|---|---|---|---|---|---|---|
| [Examples] | | | | | | | | | |
| DHE Powder Formulation 1 | 0.5/25 | 0.50 | — | — | 21.80 | — | — | 2.50 | 0.20 |
| DHE Powder Formulation 2 | 0.5/7.35 | 0.50 | 6.85 | — | — | — | — | — | — |
| DHE Powder Formulation 3 | 0.5/30 | 0.50 | 6.80 | — | 22.70 | — | — | — | — |
| DHE Powder Formulation 4 | 0.6/20 | 0.60 | 1.54 | 0.06 | 5.20 | 10.44 | — | 2.00 | 0.16 |
| DHE Powder Formulation 5 | 0.6/20 | 0.60 | 1.54 | 0.06 | — | 17.80 | — | — | — |
| DHE Powder Formulation 6 | 0.6/20 | 0.60 | 1.54 | 0.06 | 5.20 | 5.44 | 5.00 Ascorbic acid | 2.00 | 0.16 |
| DHE Powder Formulation 7 | 0.6/20 | 0.60 | 1.54 | 0.06 | — | 14.80 | 3.00 Tartaric acid | — | — |
| DHE Powder Formulation 8 | 4/20 | 4 | 10 | 1 | | 5 | | | |
| [Comparators] | | | | | | | | | |
| DHE Nasal Spray* | 0.04 mL × 4 | 0.60 | — | — | — | — | — | — | — |
| DHE Powder Formulation A | 0.6/20 | 0.60 | — | — | 17.24 | — | — | 2.00 | 0.16 |
| DHE Powder Formulation B | 0.6/20 | 0.60 | — | — | — | 16.40 | 3.00 Tartaric acid | — | — |

DHE, dihydroergotamine mesylate;
MCC-1, 1$^{st}$ microcrystalline cellulose (Ceolus ® PH-F20JP);
MCC-2, 2$^{nd}$ microcrystalline cellulose (Ceolus ® PH-301);
HPMC, hydroxypropylmethyl cellulose;
SD, spray drying;
TCP, tribasic calcium phosphate.
*Migranal Nasal Spray (Valeant Pharmaceuticals International, Inc.)

DHE Powder Formulation 9: about 1 to about 8 mg (e.g., 4 mg) of dihydroergotamine or a pharmaceutically acceptable salt thereof; about 5 to about 15 mg (e.g., 5 mg) of mannitol; and about 5 to about 15 mg (e.g., 11 mg) of microcrystalline cellulose. The average particle size diameter of the powder particles can be about 20 to about 100 microns.

DHE Powder Formulation 10: about 1 to about 8 mg (e.g., 4 mg) of dihydroergotamine or a pharmaceutically acceptable salt thereof; about 0.1 to 5 mg (e.g., 1 mg) HPMC; about 5 to about 15 mg (e.g., 5 mg) of mannitol; and about 5 to about 15 mg (e.g., 10 mg) of microcrystalline cellulose. The average particle size diameter of the powder particles can be about 20 to about 100 microns.

Methods of Making the compositions

1. Spray-Drying Methods

Spray-Dried DHE/MCC Mixture:

For DHE Powder Formulation 2 and 3, the spray-dried DHE/MCC mixture was prepared using methanol suspension mixture (at a ratio of 10:90) of DHE mesylate (Tokyo Chemical Industry, Co., Ltd.) and microcrystalline cellulose (Ceolus® PH-F20JP, Asahi Kasei Corporation) by a Buchi B-290, a spray-dryer.

Spray-Dried DHE/MCC/HPMC Mixture:

For DHE Powder Formulation 4 to 7, the spray-dried DHE/MCC/HPMC mixture was prepared using methanol suspension mixture (at a ratio of 24:73.6:2.4) of DHE mesylate (Euticals S.p.a.), microcrystalline cellulose (Ceolus® PH-F20JP, Asahi Kasei Corporation) and HPMC (Methocel E3 Premium LV, Dow Chemical Company) by a Buchi B-290, a spray-dryer.

Spray-Dried DHE/HPMC Mixture:

The spray-dried DHE/HPMC mixture was prepared using methanol solution mixture (at a ratio of 90:10) of DHE mesylate (Tokyo Chemical Industry, Co., Ltd.) and HPMC (Methocel E3 Premium LV, Dow Chemical Company) by a Buchi B-290, a spray-dryer.

Spray-Dried DHE/HPMC Mixture:

The spray-dried DHE/PVP mixture was prepared using methanol solution mixture (at a ratio of 90:10) of DHE mesylate (Tokyo Chemical Industry, Co., Ltd.) and PVP (Kollidon® 17PF, BASF SE) by a Buchi B-290, a spray-dryer.

2. Manufacturing Method of DHE Powder Formulations

DHE Powder Formulation 1:

According to the composition in Table 2, DHE Powder Formulation 1 was prepared by grinding DHE mesylate (Tokyo Chemical Industry, Co., Ltd.), two types of microcrystalline cellulose (Ceolus® PH-F20JP and Ceolus® PH-301, Asahi Kasei Corporation) and tribasic calcium phosphate (ICL Performance Products LP) in a mortar.

DHE Powder Formulation 2:

The spray-dried DHE/MCC mixture prepared was used.

DHE Powder Formulation 3:

According to the composition in Table 2, DHE Powder Formulation 3 was prepared by blending the spray-dried DHE/MCC mixture and microcrystalline cellulose (Ceolus® PH-F20JP, Asahi Kasei Corporation) in a bottle.

DHE Powder Formulation 4:

According to the compositions in Table 2, DHE Powder Formulation 4 was prepared by blending the spray-dried DHE/MCC/HPMC mixture, two types of microcrystalline cellulose (Ceolus® PH-F20JP and Ceolus® PH-301, Asahi Kasei Corporation), D-(−)-mannitol (Wako Pure Chemicals Industries, Ltd.) and tribasic calcium phosphate (ICL Performance Products LP) in a bottle.

DHE Powder Formulation 5:

According to the compositions in Table 2, DHE Powder Formulation 5 was prepared by blending the spray-dried DHE/MCC/HPMC mixture and D-(−)-mannitol (Wako Pure Chemicals Industries, Ltd.) in a bottle.

DHE Powder Formulation 6:

According to the compositions in Table 2, DHE Powder Formulation 6 was prepared by blending the spray-dried DHE/MCC/HPMC mixture, two types of microcrystalline cellulose (Ceolus® PH-F20JP and Ceolus® PH-301, Asahi Kasei Corporation), D-(−)-mannitol (Wako Pure Chemicals Industries, Ltd.), L-(+)-ascorbic acid (Wako Pure Chemicals Industries, Ltd.) and tribasic calcium phosphate (ICL Performance Products LP) in a bottle.

DHE Powder Formulation 7:

According to the compositions in Table 2, DHE Powder Formulation 7 was prepared by blending the spray-dried DHE/MCC/HPMC mixture, D-(−)-mannitol (Wako Pure Chemicals Industries, Ltd.) and L-(+)-tartaric acid (Wako Pure Chemicals Industries, Ltd.) in a bottle.

DHE Powder Formulation 8:

According to the compositions in Table 2, DHE Powder Formulation 8 was prepared by fluid bed granualation of the spray-dried DHE/HPMC mixture (about 5 microns), microcrystalline cellulose (Ceolus® PH-F20JP, about 20-23 microns), and mannitol (about 53-300 microns).

DHE Powder Formulation A:

According to the compositions in Table 2, DHE Powder Formulation A was prepared by blending the crystal form of DHE (Tokyo Chemical Industry, Co., Ltd.), two types of microcrystalline cellulose (Ceolus® PH-F20JP and Ceolus® PH-301, Asahi Kasei Corporation) and tribasic calcium phosphate (ICL Performance Products LP) in a bottle.

DHE Powder Formulation B:

According to the compositions in Table 2, DHE Powder Formulation A was prepared by blending the crystal form of DHE (Tokyo Chemical Industry, Co., Ltd.), L-(+)-tartaric acid (Wako Pure Chemicals Industries, Ltd.) and D-(−)-mannitol (Wako Pure Chemicals Industries, Ltd.) in a bottle.

Methods of Measurements

Particle size for each active agent, excipient, and powder preparation was determined under a dry powder dispersion condition by a laser diffraction system (Mastersizer 2000, Malvern Instruments Ltd.).

Example 2: Pharmacokinetic Study of Intranasal Dihydroergotamine Compositions in Primates The study described herein is designed to assess the pharmacokinetics of plasma dihydroergotamine (DHE) after intranasal administration using DHE powder compositions described herein, and to compare the pharmacokinetic profiles achieved via intranasal administration of such compositions with those of comparative DHE compositions administered via various dosing routes. The study utilizes Cynomolgus monkeys (*macaca fascicularis*, purpose bred) because the nasal cavity of such monkeys is morphologically similar to that in humans, and is commonly used as an experimental animal.

Methods

Animals. Six male Cynomolgus monkeys (*macaca fascicularis*, purpose bred), 4 to 6 years old are used, following accredited animal welfare standards.

Test Powder Compositions are listed in Table 2. Each DHE preparation was administered intramuscularly or intranasally to cynomolgus monkeys (3 to 6 kg). Bloods were collected chronologically into tube containing heparin sodium after dosing. DHE concentrations in plasma samples were determined using a LC-MS/MS (Triple Quad 6500 or API 4000, AB SCIEX).

The dose levels of the DHE powder compositions were set at 0.5 or 0.6 mg/body. As comparisons, the doses of the comparative compositions included ones set at 0.1 mg/body for IM injection and 0.6 mg/body for intranasal administration.

Powder DHE compositions were administered intranasally using a Fit-lizer dispenser as noted above, and administration was confirmed by use of a breath monitoring device.

Intranasal solutions were administered using a device manually actuated to deliver substance, and administration was confirmed by use of a breath monitoring device while holding the other nostril closed.

Intramuscular injections were performed into the brachial muscle using a disposable needle and syringe.

Sampling. Blood sampling for pharmacokinetic analyses was performed each dosing day. The sampling points were as follows: Before dosing, 2, 5, 10, 15, 20, 30, 60, 180 minutes after dosing (total: 9 points). Blood was drawn from the femoral vein with a syringe containing heparin sodium. The blood was immediately cooled on ice, centrifuged (4° C., 1710 cg, 3000 rpm, 15 minutes), and the plasma was stored in a deep freezer (−70° C. or below).

Pharmacokinetic Analysis. An LC/MS/MS analytical method was utilized for determination of DHE concentrations in plasma samples. $C_{max}$, $T_{max}$ and $AUC_{0-t}$ parameters were measured. Some of the results are summarized in Table 3 and Table 4 below and illustrated in FIGS. 1A to 1F and FIGS. 2A to 2B.

TABLE 3

Plasma DHE Concentrations after DHE Administration in Monkeys

| Preparations | N | Dose (mg) | | Time (min)/ Plasma DHE Concentration (ng/mL) | | | | | | | | |
|---|---|---|---|---|---|---|---|---|---|---|---|---|
| | | | | 0 | 2 | 5 | 10 | 15 | 20 | 30 | 60 | 180 |
| [Examples] | | | | | | | | | | | | |
| DHE Powder Formulation 1 | 6 | 0.5 | Mean SD | 0.00 0.00 | 2.17 2.32 | 2.89 1.99 | 4.07 1.89 | 5.23 1.85 | 5.09 1.73 | 5.37 1.56 | 4.69 0.87 | 2.43 0.35 |
| DHE Powder Formulation 2 | 6 | 0.5 | Mean SD | 0.00 0.00 | 5.09 2.83 | 5.19 2.64 | 4.11 1.35 | 4.33 1.91 | 3.97 1.50 | 4.12 1.39 | 4.02 1.25 | 2.77 0.97 |
| DHE Powder Formulation 3 | 6 | 0.5 | Mean SD | 0.01 0.02 | 1.95 1.57 | 3.08 2.22 | 5.30 2.22 | 6.21 1.89 | 6.99 1.78 | 6.47 1.47 | 5.88 1.26 | 3.58 0.83 |
| DHE Powder Formulation 4 | 6 | 0.6 | Mean SD | 0.00 0.00 | 6.70 5.19 | 5.56 3.63 | 4.74 2.53 | 4.66 1.66 | 4.61 1.42 | 4.21 1.08 | 3.76 0.82 | 1.91 0.43 |
| DHE Powder Formulation 5 | 6 | 0.6 | Mean SD | 0.00 0.00 | 3.65 3.53 | 4.14 3.81 | 4.43 3.70 | 4.83 3.05 | 4.84 2.41 | 4.51 1.88 | 3.74 1.09 | 2.00 0.52 |
| DHE Powder Formulation 6 | 6 | 0.6 | Mean SD | 0.00 0.00 | 4.03 2.01 | 4.54 2.10 | 4.57 1.69 | 4.63 1.51 | 5.08 1.26 | 5.19 1.41 | 4.84 0.55 | 2.51 0.56 |
| DHE Powder Formulation 7 | 6 | 0.6 | Mean SD | 0.00 0.00 | 6.77 3.31 | 7.60 4.41 | 6.80 2.45 | 7.55 1.76 | 7.18 1.42 | 6.68 1.44 | 5.04 0.73 | 2.32 0.53 |
| [Comparators] | | | | | | | | | | | | |
| DHE IM Injection | 6 | 0.1 | Mean SD | 0.00 0.00 | 2.57 0.78 | 5.15 1.47 | 6.46 1.93 | 6.54 1.32 | 5.69 0.78 | 5.29 0.88 | 3.81 0.29 | 1.72 0.15 |
| DHE Nasal Spray | 6 | 0.6 | Mean SD | 0.00 0.00 | 0.03 0.06 | 0.47 0.29 | 1.32 0.59 | 2.43 0.87 | 3.11 1.05 | 4.29 0.92 | 4.83 1.04 | 2.67 0.70 |
| DHE Powder Formulation A | 6 | 0.6 | Mean SD | 0.00 0.00 | 0.83 0.75 | 1.33 0.85 | 2.08 0.75 | 2.58 0.75 | 3.05 1.09 | 2.91 0.62 | 2.50 0.60 | 1.30 0.33 |
| DHE Powder Formulation B | 6 | 0.6 | Mean SD | 0.00 0.00 | 1.51 0.86 | 2.54 1.58 | 2.57 1.33 | 2.85 1.12 | 2.99 1.10 | 3.34 0.90 | 3.40 1.03 | 1.90 0.42 |

TABLE 4

DHE PK Parameters in Monkeys

| Preparations | N | Dose (mg) | | Tmax (min) | Cmax (ng/mL) | $AUC_{0-15\ min}$ | $AUC_{0-30\ min}$ | $AUC_{0-60\ min}$ | $AUC_{0-180\ min}$ |
|---|---|---|---|---|---|---|---|---|---|
| | | | | | | (ng * min/mL) | | | |
| [Examples] | | | | | | | | | |
| DHE Powder Formulation 1 | 6 | 0.5 | Mean SD | 30.0 13.4 | 6.0 1.7 | 50.4 27.4 | 128.5 49.5 | 279.3 78.6 | 706.5 132.2 |
| DHE Powder Formulation 2 | 6 | 0.5 | Mean SD | 5.8 2.7 | 7.3 6.1 | 64.9 26.4 | 126.0 45.3 | 248.1 83.5 | 655.4 206.6 |
| DHE Powder Formulation 3 | 6 | 0.5 | Mean SD | 26.7 17.5 | 7.3 1.9 | 59.2 26.0 | 159.6 43.4 | 344.9 77.4 | 912.6 177.6 |
| DHE Powder Formulation 4 | 6 | 0.6 | Mean SD | 14.7 23.3 | 7.3 4.4 | 74.3 43.9 | 141.6 62.9 | 261.2 89.0 | 601.3 152.2 |
| DHE Powder Formulation 5 | 6 | 0.6 | Mean SD | 25.8 18.0 | 5.6 3.2 | 59.9 49.9 | 130.8 84.3 | 254.6 127.9 | 599.1 219.9 |
| DHE Powder Formulation 6 | 6 | 0.6 | Mean SD | 30.0 25.1 | 5.9 1.6 | 62.7 24.4 | 138.3 41.7 | 288.7 66.4 | 730.0 121.5 |
| DHE Powder Formulation 7 | 6 | 0.6 | Mean SD | 15.8 9.7 | 9.0 3.5 | 100.2 41.4 | 206.4 59.5 | 382.1 87.6 | 823.7 154.0 |
| [Comparators] | | | | | | | | | |
| DHE IM Injection | 6 | 0.1 | Mean SD | 4.8 0.6 | 6.8 1.5 | 75.7 16.0 | 161.2 27.5 | 297.7 40.6 | 629.8 45.0 |
| DHE Nasal Spray | 6 | 0.6 | Mean SD | 60.0 0.0 | 4.8 1.0 | 14.6 5.9 | 65.5 19.1 | 202.3 46.1 | 652.3 139.1 |
| DHE Powder Formulation A | 6 | 0.6 | Mean SD | 25.0 5.5 | 3.2 0.9 | 24.3 10.2 | 68.2 22.0 | 149.3 39.3 | 377.4 93.0 |
| DHE Powder Formulation B | 6 | 0.6 | Mean SD | 40.8 22.9 | 3.8 1.2 | 33.9 17.2 | 80.2 31.7 | 181.3 58.6 | 499.7 138.2 |

Example 3: X-Ray Powder Diffraction (XYPD) Analysis

Figure 3A:
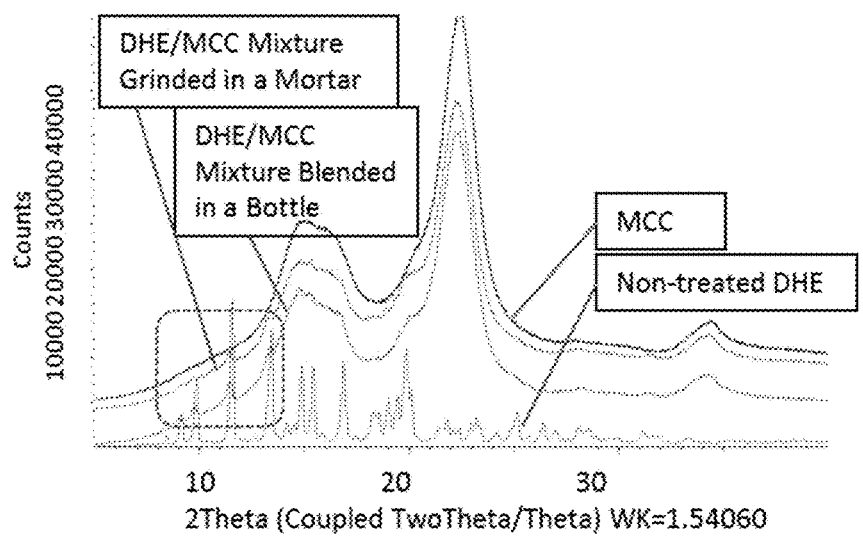
FIGS. 3A, 3B, and 3C are a group of X-ray diffraction spectra overlay comparing various DHE formulations.
Figure 3B:
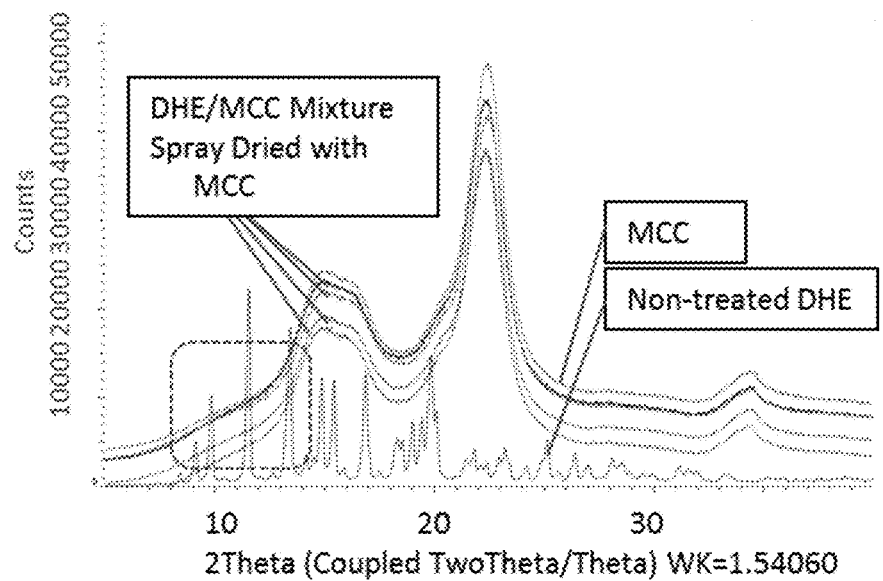
Figure 3C:
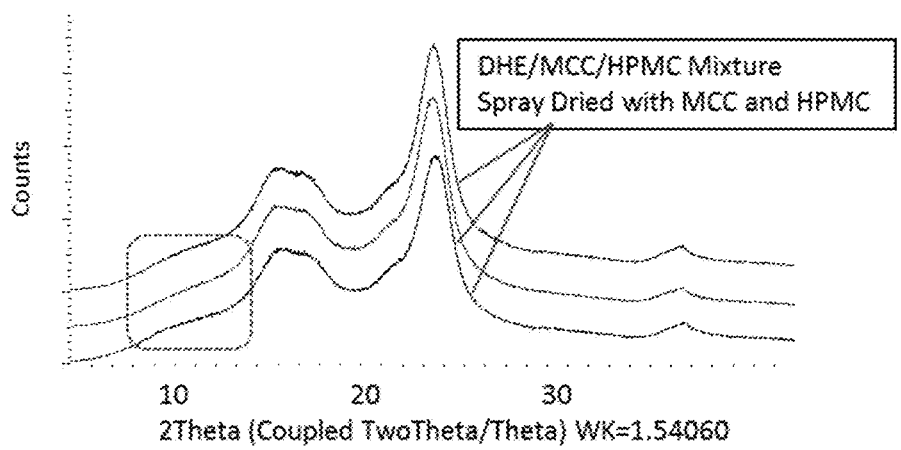

For non-treated DHE mesylate, spray-dried DHE/MCC mixture and spray-dried DHE/MCC/HPMC mixture, their XRPD were performed using a Brucker D2 Phaser X-ray diffractometer to evaluate the crystallinity of DHE. FIGS. 3A to 3C contain X-ray diffraction spectra overlay comparing several DHE preparations that comprise DHE alone or with MCC or MCC/HPMC.

Example 4: Scanning Electron Microscope (SEM) Analysis

Figure 4:
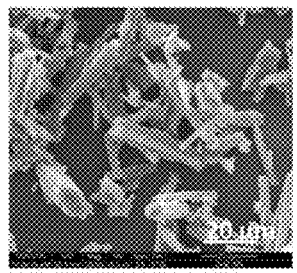
FIG. 4 is a group of scanning electron microscope (SEM) scans of various DHE formulations.
Figure 4:
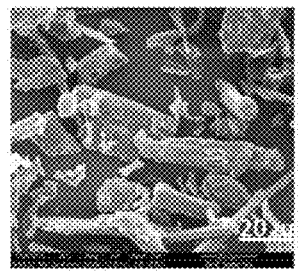
Figure 4:
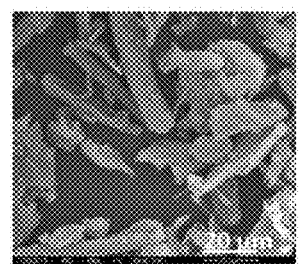
Figure 4:
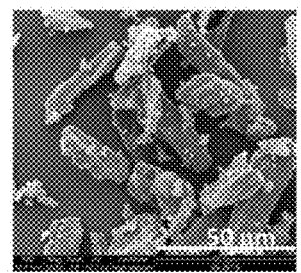
Figure 4:
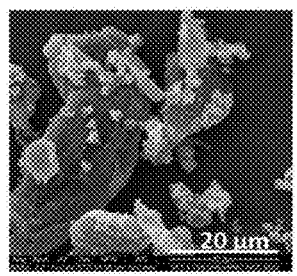
Figure 4:
Figure 4:
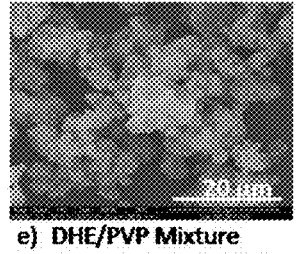

SEM samples were prepared by dispersing powder onto an adhesive carbon-coated sample stub a coating with a thin conductive layer of gold/palladium using a Polaron Autocoater E5200. Samples were analyzed using a FEI Quanta 200 SEM fitted with an Everhart-Thornley (secondary electron) detector, operating in high vacuum mode. FIG. 4 is a group of scanning electron microscope (SEM) scans of several DHE preparations that comprise DHE alone or with MCC, MCC/HPMC, or PVP.

Examples 5-1 and 5-2: Indomethacin

Physical Properties of Indomethacin
Type: Small Molecule
Molecular Weight: 357.0
Water solbility: 0.937 µg/mL (at 25° C.)
Log P: 4.27

Example 5-1

Indomethacin powder preparations were prepared by blending indomethacin spray-dried with MCC and HPMC, and additional MCC. The indomethacin powder formulation, indomethacin liquid suspension and an indomethacin powder formulation in a crystal form will be dosed to monkeys. Plasma indomethacin concentrations and the corresponding pharmacokinetic parameters for each preparation will be determined.

Example 5-2

Preparation of Intransal Indomethacin Compostions

Methods of Making the Compositions

Freeze-dried Indomethacin: For IMC Powder Formulation 1, the freeze-dried indomethacin was prepared using saturated indomethacin (Wako Pure Chemical Industries, Ltd.) solution dissolved with 50% ethanol by a freeze-dryer (Labconco FreeZone Triad Freeze Dry System, Thermo Fisher Scientific Inc.) under the following conditions.

| Step | Pre-set Temp (° C.) | Duration (h) | Temp Ramp (° C./min) | Vacuum (mTorr) |
|---|---|---|---|---|
| Sample Pre-Freezing | −80 | 1.5 | — | — |
|  | — | — | 1.0 |  |
| $1^{st}$ Drying | −35 | 14.5 | — | 105 |
|  | — | — | 0.25 |  |
| $2^{nd}$ Drying | 30 | 4.0 | — |  |
|  | — | — | 0.25 |  |

IMC Powder Formulation 1:

According to the composition in Table 5, IMC Powder Formulation 1 was prepared by grinding the freeze-dried indomethacin, two types of microcrystalline cellulose (Ceolus® PH-F20JP and Ceolus® PH-301, Asahi Kasei Corporation) and tribasic calcium phosphate (ICL Performance Products LP) in a mortar.

IMC Powder Formulation A:

According to the composition in Table 5, IMC Powder Formulation A was prepared by blending the crystal form of indomethacin (Wako Pure Chemical Industries, Ltd.), two types of microcrystalline cellulose (Ceolus® PH-F20JP and Ceolus® PH-301, Asahi Kasei Corporation) and tribasic calcium phosphate (ICL Performance Products LP) in a bottle.

TABLE 5

Intranasal Indomethacin Compositions

| Preparations | IMC/ Formulation (mg/mg) | IMC | MCC-1 for FD | HPMC for FD | MCC-1 | Mannitol (mg) | pH Adjuster | MCC-2 | TCP |
|---|---|---|---|---|---|---|---|---|---|
| [Examples] |  |  |  |  |  |  |  |  |  |
| IMC Powder Formulation 1 | 1/20 | 1.00 | — | — | 16.84 | — | — | 2.00 | 0.16 |
| [Comparator] |  |  |  |  |  |  |  |  |  |
| IMC Powder Formulation A | 1/20 | 1.00 | — | — | 16.84 | — | — | 2.00 | 0.16 |

IMC, indomethacin;
MCC-1, $1^{st}$ microcrystalline cellulose (Ceolus ® PH-F20JP);
MCC-2, $2^{nd}$ microcrystalline cellulose (Ceolus ® PH-301);
HPMC, hydroxypropylmethyl cellulose;
FD, freeze drying;
TCP, tribasic calcium phosphate.

Pharmacokinetic Study of Intranasal Indomethacin Compositions in Primates

TABLE 6

Plasma Indomethacin Concentrations after Intranasal Indomethacin Compositions Administration in Monkeys

| Preparations | N | Dose (mg) | | Time (min)/ Plasma IMC Concentration (ng/mL) | | | | |
|---|---|---|---|---|---|---|---|---|
| | | | | 0 | 10 | 30 | 60 | 120 | 240 |
| [Examples] | | | | | | | | | |
| IMC Powder Formulation 1 [Comparator] | 2 | 1.0 | Mean | BLQ | 493 | 207 | 62 | 23 | 36 |
| IMC Powder Formulation A | 2 | 1.0 | Mean | BLQ | 298 | 196 | 90 | 27 | 25 |

BLQ: Below the lower limit of quantification (<1 ng/mL)

TABLE 7

Indomethacin PK Parameters in Monkeys

| Preparations | N | Dose (mg) | | Tmax (min) | Cmax (ng/mL) | $AUC_{0\text{-}10\,min}$ | $AUC_{0\text{-}30\,min}$ | $AUC_{0\text{-}60\,min}$ | $AUC_{0\text{-}240\,min}$ |
|---|---|---|---|---|---|---|---|---|---|
| | | | | | | (ng * min/mL) | | | |
| [Examples] | | | | | | | | | |
| IMC Powder Formulation 1 [Comparator] | 2 | 1.0 | Mean | 10 | 493 | 2465 | 9465 | 13506 | 19601 |
| IMC Powder Formulation A | 2 | 1.0 | Mean | 10 | 298 | 1490 | 6245 | 10704 | 17296 |

The study described herein is designed to assess the pharmacokinetics of plasma indomethacin after intranasal administration using indomethacin powder compositions described herein, and to compare the pharmacokinetic profiles achieved via intranasal administration of such compositions with the comparative indomethacin composition administered intranasally. The study utilizes Cynomolgus monkeys (macaca fascicularis, purpose bred) because the nasal cavity of such monkeys is morphologically similar to that in humans, and is commonly used as an experimental animal.

Four male Cynomolgus monkeys (macaca fascicularis, purpose bred), 5 to 8 years old are used, following accredited animal welfare standards.

Test Powder Compositions are listed in Table 5. Each intranasal indomethacin composition was administered intranasally to cynomolgus monkeys (5 to 6 kg). Bloods were collected chronologically into tube containing heparin sodium after dosing. Indomethacin concentrations in plasma samples were determined using a LC-MS/MS (LC system: Shimadzu 30A, Shimadzu Corporation; MS/MS system: API4000, AB SCIEX). The dose level of the indomethacin powder compositions was set at 1.0 mg/body.

Intranasal indomethacin compositions were administered intranasally using a Fit-lizer dispenser as noted above, and administration was confirmed by use of a breath monitoring device.

Sampling. Blood sampling for pharmacokinetic analyses was performed each dosing day. The sampling points were as follows: Before dosing, 10, 30, 60, 120 and 240 minutes after dosing (total: 6 points). Blood was drawn from the femoral vein with a syringe containing heparin sodium. The blood was immediately cooled on ice, centrifuged (4° C., 1710 cg, 3000 rpm, 15 minutes), and the plasma was stored in a deep freezer (−70° C. or below).

Figure 5:
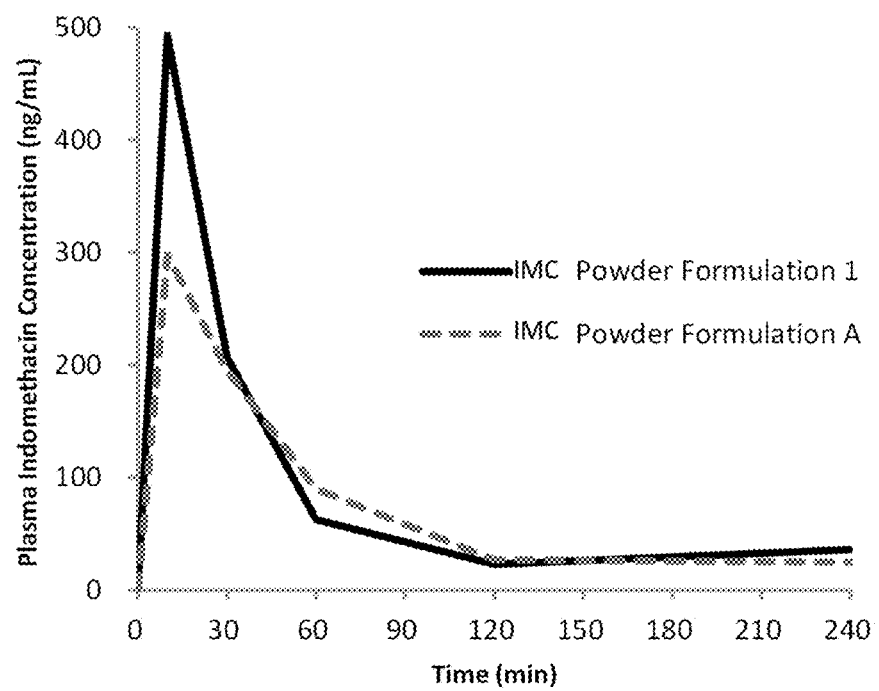
FIG. 5 is a graph showing plasma indomethacin concentration-time profiles in monkeys.

Pharmacokinetic Analysis. An LC/MS/MS analytical method was utilized for determination of indomethacin concentrations in plasma samples. Cmax, Tmax and AUC0-t parameters were measured. Some of the results are summarized in Table 6 and Table 7 below and illustrated in FIG. 5.

X-Ray Powder Diffraction (XRPD) Analysis

Figure 6:
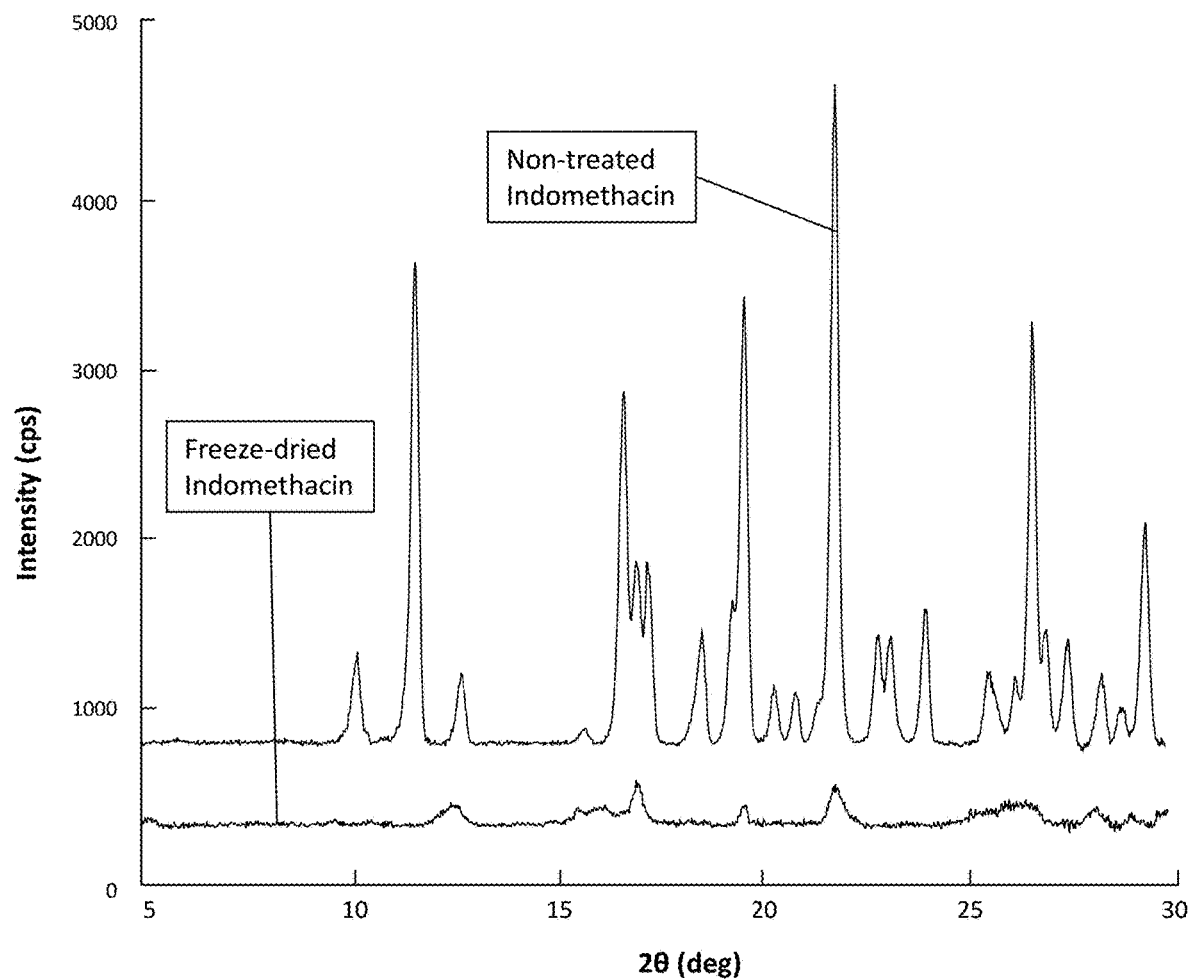
FIG. 6 is a graph showing X-ray diffraction spectra of freeze-dried indomethacin and non-treated indomethacin.

For non-treated indomethacin and freeze-dried indomethacin, their XRPD were performed using a Rigaku Ultima IV (Rigaku Corporation) to evaluate the crystallinity of indomethacin. FIG. 6 contain X-ray diffraction spectra overlay comparing several indomethacin preparations that comprise indomethacin alone.

Particle Size Analysis

For IMC Powder Formulation 1, containing the freeze-dried indomethacin, two types of microcrystalline cellulose (Ceolus® PH-F20JP and Ceolus® PH-301, Asahi Kasei Corporation) and tribasic calcium phosphate (ICL Performance Products LP), their particle size was analyzed by laser-diffraction method using a Mastersizer 2000 (Malvern Instruments Limited). Some of the results are summarized in Table 8. An average particle size (Volume under 50%) of IMC Powder Formulation 1 is 22.1 µm.

TABLE 8

Particle Size Distribution of Intranasal Indomethacin Compositions

| Preparations [Examples] | Dose (mg) | Amount (mg) | Particle Size (µm) | | |
|---|---|---|---|---|---|
| | | | Volume under 10% | Volume under 50% | Volume under 90% |
| IMC Powder Formulation 1 | 1.0 | 20.0 | 7.7 | 22.1 | 70.5 |

Example 6: Testosterone

Physical properties of Testosterone

Type: Small Molecule

Molecular Weight: 288.4

Water solubility: 23.4 µg/mL (at 25° C.)

Log P: 3.32

Preparations of Intranasal Testosterone Compositions

TABLE 9

Intranasal Testosterone Compositions

| Preparations | TSS/ Formulation (mg/mg) | TSS | MCC-1 for FD | HPMC for FD | MCC-1 | Mannitol (mg) | pH Adjuster | MCC-2 | TCP |
|---|---|---|---|---|---|---|---|---|---|
| [Examples] | | | | | | | | | |
| TSS Powder Formulation 1 [Comparator] | 2/20 | 2 | — | — | 15.84 | — | — | 2.00 | 0.16 |
| TSS Powder Formulation A | 2/20 | 2 | — | — | 15.84 | — | — | 2.00 | 0.16 |

TSS, testosterone;
MCC-1, 1$^{st}$ microcrystalline cellulose (Ceolus ® PH-F20JP);
MCC-2, 2$^{nd}$ microcrystalline cellulose (Ceolus ® PH-301);
HPMC, hydroxypropylmethyl cellulose;
FD, freeze drying;
TCP, tribasic calcium phosphate.

Methods of Making the Compositions

Freeze-dried testosterone: For TSS Powder Formulation 1, the freeze-dried testosteron was prepared using a 4 mg/mL solution of testosterone (Wako Pure Chemical Industries, Ltd.) dissolved with 50% ethanol solution by a freeze-dryer (Labconco FreeZone Triad Freeze Dry System, Thermo Fisher Scientific Inc.) under the following conditions.

| Step | Pre-set Temp (° C.) | Duration (h) | Temp Ramp (° C./min) | Vacuum (mTorr) |
|---|---|---|---|---|
| Sample Pre-Freezing | −80 | 1.5 | — | — |
| | | | 1.0 | |
| 1$^{st}$ Drying | −35 | 14.5 | — | 105 |
| | | | 0.25 | |
| 2$^{nd}$ Drying | 30 | 4.0 | — | |
| | | | 0.25 | |

Manufacturing Method of Testosterone Powder Formulations

TSS Powder Formulation 1:

According to the composition in Table 9, TSS Powder Formulation 1 was prepared by grinding the freeze-dried testosterone, two types of microcrystalline cellulose (Ceolus® PH-F20JP and Ceolus® PH-301, Asahi Kasei Corporation) and tribasic calcium phosphate (ICL Performance Products LP) in a mortar.

TSS Powder Formulation A:

According to the compositions in Table 9, TSS Powder Formulation A was prepared by blending the crystal form of testosterone (Wako Pure Chemical Industries, Ltd.), two types of microcrystalline cellulose (Ceolus® PH-F20JP and Ceolus® PH-301, Asahi Kasei Corporation) and tribasic calcium phosphate (ICL Performance Products LP) in a bottle.

Pharmacokinetic Study of Intranasal Testosterone Compositions in Promates

TABLE 10

Plasma Testosterone Concentrations after Intranasal Testosterone Compositions Administration in Monkeys

| Preparations | N | Dose (mg) | Time (min)/ Plasma TSS Concentration (ng/mL) | | | | | |
|---|---|---|---|---|---|---|---|---|
| | | | 0 | 10 | 30 | 60 | 120 | 240 |
| [Examples] | | | | | | | | |
| TSS Powder Formulation 1 [Comparator] | 1 | 2.0 | BLQ | 131.6 | 77.6 | 88.1 | 30.6 | 5.7 |
| TSS Powder Formulation A | 1 | 2.0 | BLQ | 83.7 | 84.4 | 68.7 | 27.6 | 6.3 |

BLQ: Below the lower limit of quantification (<4 ng/mL)

TABLE 11

Testosterone PK Parameters in Monkeys

| Preparations | N | Dose (mg) | Tmax (min) | Cmax (ng/mL) | AUC$_{0-10\ min}$ | AUC$_{0-30\ min}$ (ng * min/mL) | AUC$_{0-60\ min}$ | AUC$_{0-240\ min}$ |
|---|---|---|---|---|---|---|---|---|
| [Examples] | | | | | | | | |
| TSS Powder Formulation 1 [Comparator] | 1 | 2.0 | 10 | 131.6 | 658.0 | 2750.0 | 5235.5 | 10974.5 |
| TSS Powder Formulation A | 1 | 2.0 | 30 | 84.4 | 418.5 | 2099.5 | 4396.0 | 8485.5 |

The study described herein is designed to assess the pharmacokinetics of plasma testosterone after intranasal administration using testosterone powder compositions described herein, and to compare the pharmacokinetic profiles achieved via intranasal administration of such compositions with the comparative testosterone composition administered intranasally. The study utilizes Cynomolgus monkeys (*macaca fascicularis*, purpose bred) because the nasal cavity of such monkeys is morphologically similar to that in humans, and is commonly used as an experimental animal.

Two male Cynomolgus monkeys (*macaca fascicularis*, purpose bred), 5 to 8 years old are used, following accredited animal welfare standards.

Test powder compositions are listed in Table 9. Each intranasal testosterone composition was administered intranasally to cynomolgus monkeys (5 to 6 kg). Bloods were collected chronologically into tube containing heparin sodium after dosing. Testosterone concentrations in plasma samples were determined by immunoassay using the Abbott Architect i2000 (ARCHITECT® Testosterone, Abott Japan Inc.). The dose level of the testosterone powder compositions was set at 2.0 mg/body.

Intranasal testosterone compositions were administered intranasally using a Fit-lizer dispenser as noted above, and administration was confirmed by use of a breath monitoring device.

Sampling. Blood sampling for pharmacokinetic analyses was performed each dosing day. The sampling points were as follows: Before dosing, 10, 30, 60, 120 and 240 minutes after dosing (total: 6 points). Blood was drawn from the femoral vein with a syringe containing heparin sodium. The blood was immediately cooled on ice, centrifuged (4° C., 1710 cg, 3000 rpm, 15 minutes), and the plasma was stored in a deep freezer (−70° C. or below).

Figure 7:
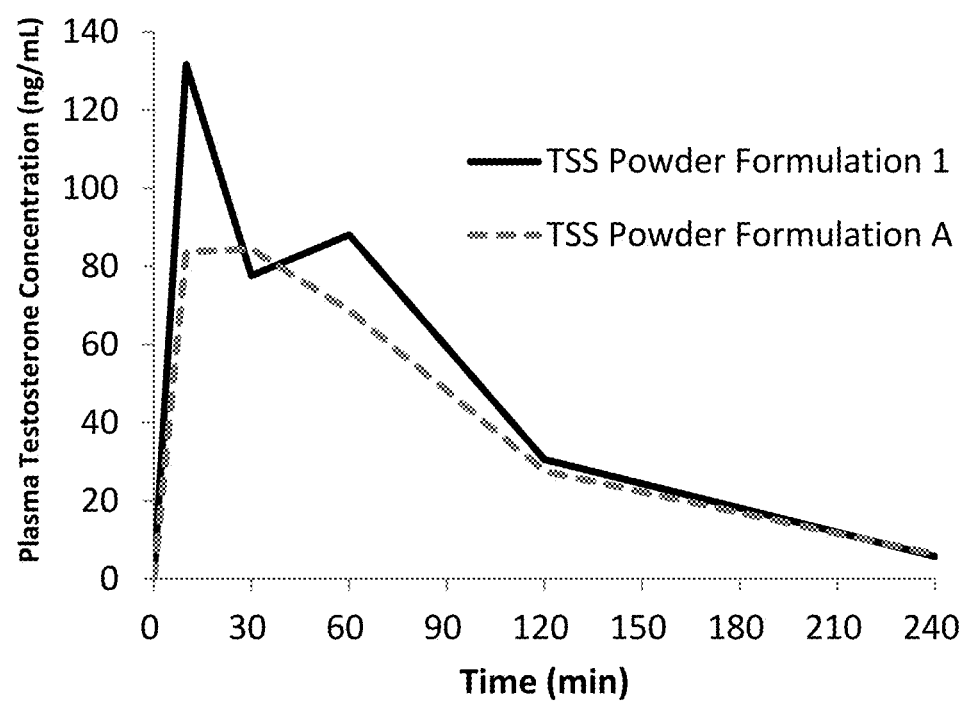
FIG. 7 is a graph showing plasma testosterone concentration-time profiles in monkeys.

Pharmacokinetic Analysis. An EIA method was utilized for determination of testosterone concentrations in plasma samples. Cmax, Tmax and AUC0-t parameters were measured. Some of the results are summarized in Table 10 and Table 11 below and illustrated in FIG. 7.

X-Ray Powder Diffraction (XRPD) Analysis

Figure 8:
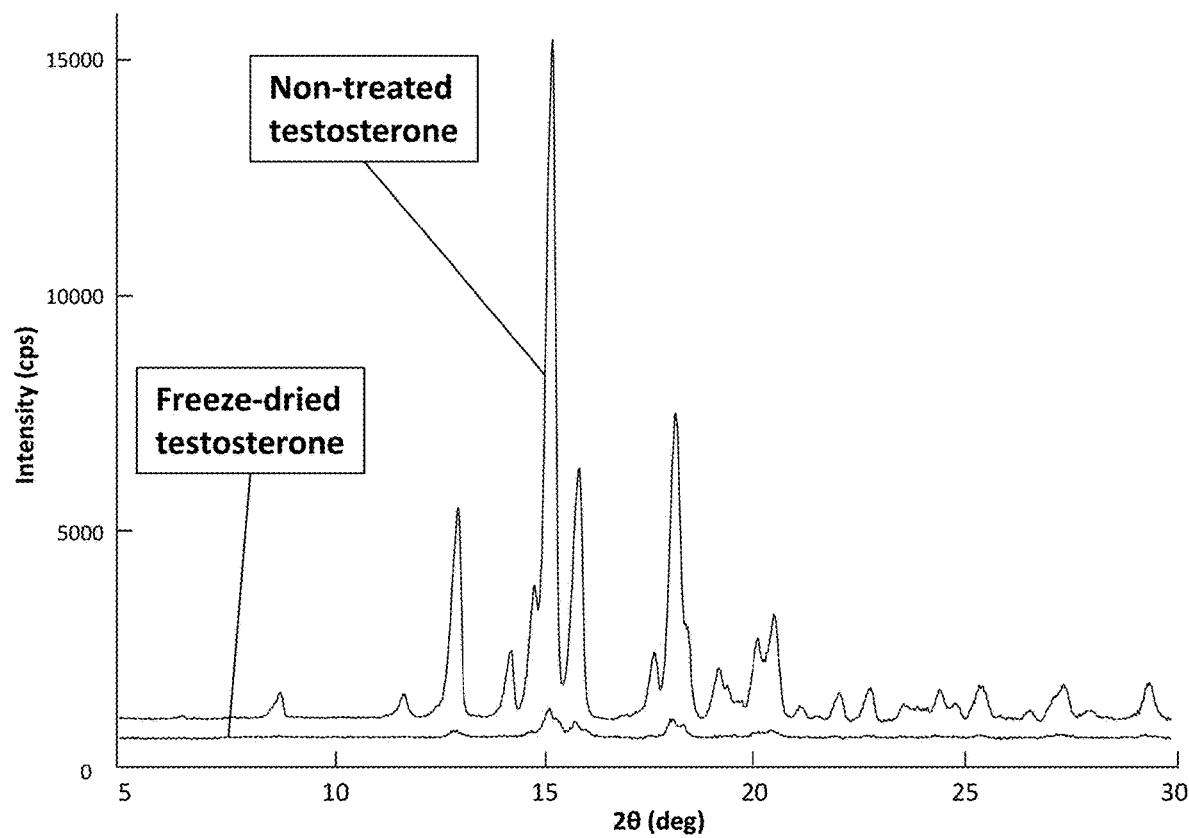
FIG. 8 is a graph comparing X-ray diffraction spectra of freeze-dried testosterone and non-treated testosterone.

For non-treated indomethacin, spray-dried indomethacin and freeze-dried indomethacin, their XRPD were performed using a Rigaku Ultima IV (Rigaku Corporation) to evaluate the crystallinity of testosterone. FIG. 8 contains X-ray diffraction spectra overlay comparing two testosterone preparations that comprise testosterone alone.

Particle Size Analysis

For TSS Powder Formulation 1, containing the freeze-dried testosterone, two types of microcrystalline cellulose (Ceolus® PH-F20JP and Ceolus® PH-301, Asahi Kasei Corporation) and tribasic calcium phosphate (ICL Performance Products LP), their particle size was analyzed by laser-diffraction method using a Mastersizer 2000 (Malvern Instruments Limited). Some of the results are summarized in Table 12. An average particle size (Volume under 50%) of TSS Powder Formulation 1 is 25.6 µm.

TABLE 12

Particle Size Distribution of Intranasal Testosterone Compositions

| Preparations [Examples] | Dose (mg) | Amount (mg) | Particle Size (µm) | | |
|---|---|---|---|---|---|
| | | | Volume under 10% | Volume under 50% | Volume under 90% |
| TSS Powder Formulation 1 | 2.0 | 20.0 | 8.7 | 25.6 | 107.2 |

Example 7: Midazolam

Midazolam powder preparations were prepared by blending midazolam spray-dried with MCC and HPMC, and additional MCC. The midazolam powder formulation, midazolam liquid suspension and a midazolam powder formulation in a crystal form will be dosed to monkeys. Plasma midazolam concentrations and the corresponding pharmacokinetic parameters for each preparation will be determined.

Example 8: Phenobarbital

Phenobarbital powder preparations were prepared by blending phenobarbital spray-dried with MCC and HPMC, and additional MCC. The phenobarbital powder formulation, phenobarbital liquid suspension and a phenobarbital powder formulation in a crystal form will be dosed to monkeys. Plasma phenobarbital concentrations and the corresponding pharmacokinetic parameters for each preparation will be determined.

Example 9: Treatment of Migraine with Intranasal Powder Composition

Three doses of present DHE powder formulations and DHE SC or IM injection will be administered intranasally in healthy humans to evaluate the pharmacokinetics, dose proportionality, safety, tolerability, the relative bioavailability to DHE injection.

Example 10: Preparation of Powder Compositions

A powder composition is made with an active agent disclosed in this application and one or more excipients disclosed herein, for example, a carrier (e.g., microcrystalline cellulose), a thickening agent (e.g., HPMC), a fluidizing agent (e.g., TCP), a sugar alcohol (e.g., mannitol), and a pH adjuster/pH adjusting agent (e.g., ascorbic acid, tartaric acid), in any amount disclosed herein.

The active agent can be is indomethacin, testosterone, midazolam, phenobarbital, or any combination thereof.

The active agent can also be didanosine, zidovudine, lamivudine, acyatazanavir, nelfenavir, sanilvudine, emtricitabine, polyinosinic-polycytidylic acid, oseltamivir, zanamivir, valganciclovir, peramivir, laninamivir, favipiravir, amantadine, amphotericin B, miconazole, fluconazole, itraconazole, ketoconazole, ketamine, pentobarbital sodium, thiopental, amopentobarbital, hexobarbital, lidocaine, triazolam, zopiclone, zolpidem, eszopiclone, etizolam, clotiazepam, brotizolam, lormetazepam, estazolam, midazolam, nitrazepam, flunitrazepam, diazepam, chlordiazepoxide HCl, alprazolam, lorazepam, ethyl loflazepate, bromazepam, rilmazafone, chloral hydrate, carbamazepine, clonazepam, zonisamide, sodium valproate, phenytoin, phenobarbital, primidone, gabapentin, opium, morphine, ethylmorphine, oxycodone, hydrocodone, codeine, dihydrocodeine, fentanyl, remifentanil, droperidol, levorphanol, methadone, meperidine, pethidine, buprenorphine, butorphanol, tramadol, tapentadol, nalfurafine, pentazocine, nalbuphine hydrochloride, nalorphine, eptazocine, levallorphan, sulpyrine, aspirin, acetaminophen, ergotamine, dihydroergotamine, sumatriptan, eletriptan, zolmitriptan, rizatriptan, naratriptan, almotriptan, frovatriptan, avitriptan, lasmiditan, olcegepant, telcagepant, donepezil, suxamethonium, pancuronium, sildenafil, vardenafil, apomorphine, tadalafil, atropine, scopolamine, homatropine methylbromide, chlorpromazine, digitoxin, levomepromazine, thioridazine, acepromazine, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, progesterone, testosterone, dehydroepiandrosterone, estrogen, estradiol, levonorgestrel, protamine, leucovorin, dimercaprol, deferoxamine, sodium thiosulfate, mifepristone, risperidone, olanzapine, thalidomide, civamide, acyclovir, valacyclovir, famciclovir, penciclovir, lopinavir, ritonavir, saquinavir, vidarabine, idoxuridine, nifedipine, nimodipine, amiodarone, loratadine, tretinoin, carmustin, beraprost sodium, or any combination thereof. The active agent can also be insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, FK-506, octreotide, carperitide, pramlintide, lanreotide, eptifibatide, albiglutide, pasireotide, teriparatide, exenatide, liraglutide, emfuvirtide, ziconotide, ecallantide, mifamurtide, nesiritide, peglinesatide, afamelanotide, linaclotide, lixisenatide, teduglutide, bentiromide, cureletide diethylamine, degarelix, ghrelin, atrial natriuretic peptide, a peptide analog thereof, or any combination thereof.

The examples and instances described herein are for illustrative purposes only and various modifications or changes suggested to persons skilled in the art are to be included within the spirit and purview of this application and scope of the appended claims.

What is claimed is:

1. An intranasal pharmaceutical powder composition, wherein the intranasal pharmaceutical powder composition comprises particles that comprise an active agent, a carrier, and at least one member selected from the group consisting of a thickening agent, a pH adjusting agent, a sugar alcohol, and any combination thereof, and wherein:
   the active agent comprises dihydroergotamine (DHE) or a pharmaceutically acceptable salt thereof, indomethacin or a pharmaceutically acceptable salt thereof, or testosterone or a pharmaceutically acceptable salt thereof;
   the carrier comprises a microcrystalline cellulose, wherein the microcrystalline cellulose is at least partially coated with the active agent;
   at least about 20 percent by weight of the active agent in the particles is amorphous as determined by X-ray diffraction;
   when the active agent has a crystalline form, a solubility of the active agent in a crystalline form in an aqueous liquid ranges from about 0.1 μg/mL to about 1 mg/mL in water at a temperature of 37±0.5° C.;
   the particles have an average particle size of about 10 microns to about 300 microns, as measured by laser diffraction; and
   when the intranasal pharmaceutical powder composition is administered to a human subject, a pharmacokinetic parameter of the active agent increases by at least about 15%, compared to a corresponding composition that comprises the active agent that is in a crystalline form when administered intranasally to a comparable human subject, as measured by a same method, and wherein the pharmacokinetic parameter comprises $AUC_{0-10min}$, $AUC_{0-15min}$, $AUC_{0-30min}$, $C_{max}$, or any combination thereof.

2. The intranasal pharmaceutical powder composition of claim 1, wherein:
   the intranasal pharmaceutical powder composition further comprises particles at least some of which substantially contain a single ingredient selected from the group consisting of the active agent, the thickening agent, the carrier, the pH adjusting agent, and the sugar alcohol; or
   the intranasal pharmaceutical powder composition further comprises particles at least some of which contain a single ingredient selected from the group consisting of the active agent, the thickening agent, the carrier, the pH adjusting agent, and the sugar alcohol; or
   the intranasal pharmaceutical powder composition further comprises particles at least some of which contain at least two ingredients selected from the group consisting of the active agent, the thickening agent, the carrier, the pH adjusting agent, and the sugar alcohol; or
   the intranasal pharmaceutical powder composition further comprises particles that comprise the active agent and are free from the thickening agent, the carrier, or a combination thereof; or
   at least some of the particles are aggregates; or
   at least some of the particles are agglomerates; or
   any combination thereof.

3. The intranasal pharmaceutical powder composition of claim 1, wherein the active agent is dihydroergotamine (DHE) or a pharmaceutically acceptable salt thereof.

4. The intranasal pharmaceutical powder composition of claim 3, wherein the active agent is DHE mesylate.

5. The intranasal pharmaceutical powder composition of claim 1, wherein the active agent is indomethacin or a pharmaceutically acceptable salt thereof.

6. The intranasal pharmaceutical powder composition of claim 1, wherein the active agent is testosterone or a pharmaceutically acceptable salt thereof.

7. The intranasal pharmaceutical powder composition of claim 1, wherein the carrier further comprises ethyl cellulose, cellulose acetate, cellulose acetate butyrate, cellulose acetate propionate, cellulose acetate phthalate, hydroxypropylmethylcellulose phthalate, starch, chitosan, or any combination thereof.

8. The intranasal pharmaceutical powder composition of claim 1, wherein the microcrystalline cellulose has an average particle size of about 20 μm to about 50 μm.

9. The intranasal pharmaceutical powder composition of claim 1, wherein the sugar alcohol is selected from the group consisting of mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof.

10. The intranasal pharmaceutical powder composition of claim 1, wherein the intranasal pharmaceutical powder composition comprises the active agent, the carrier that is microcrystalline cellulose, and the sugar alcohol that is mannitol.

11. The intranasal pharmaceutical powder composition of claim 1, wherein the intranasal pharmaceutical powder composition comprises the active agent that is dihydroergotamine or a pharmaceutically acceptable salt thereof, the carrier that is microcrystalline cellulose, and the sugar alcohol that is mannitol.

12. The intranasal pharmaceutical powder composition of claim 11, wherein the intranasal pharmaceutical powder composition further comprises the thickening agent that is hydroxypropyl methylcellulose (HPMC).

13. The intranasal pharmaceutical powder composition of claim 11,
wherein the intranasal pharmaceutical powder composition comprises:
1) the dihydroergotamine or a pharmaceutically acceptable salt thereof that is present in about 20% of a total weight of the intranasal pharmaceutical powder composition;
2) the mannitol that is present in about 25% of the total weight of the intranasal pharmaceutical powder composition; and
3) the microcrystalline cellulose that is present in about 55% of the total weight of the intranasal pharmaceutical powder composition, and
wherein the intranasal pharmaceutical powder composition has an average particle size diameter of about 20 to about 100 μm.

14. The intranasal pharmaceutical powder composition of claim 1, wherein the intranasal pharmaceutical powder composition comprises:
1) about 1 to about 8 mg of the dihydroergotamine or a pharmaceutically acceptable salt thereof;
2) about 5 to about 15 mg of the mannitol; and
3) about 5 to about 15 mg of the microcrystalline cellulose.

15. The intranasal pharmaceutical powder composition of claim 14,
wherein the intranasal pharmaceutical powder composition comprises:
1) about 4 mg of the dihydroergotamine or a pharmaceutically acceptable salt thereof;
2) about 5 mg of the mannitol; and
3) about 11 mg of the microcrystalline cellulose, and
wherein the intranasal pharmaceutical powder composition has an average particle size diameter of about 20 to about 100 μm.

16. The intranasal pharmaceutical powder composition of claim 1, wherein the intranasal pharmaceutical powder composition comprises the active agent that is indomethacin or a pharmaceutically acceptable salt thereof and the carrier that is microcrystalline cellulose, and further comprises tribasic calcium phosphate.

17. The intranasal pharmaceutical powder composition of claim 1, wherein the intranasal pharmaceutical powder composition comprises the active agent that is testosterone or a pharmaceutically acceptable salt thereof and the carrier that is microcrystalline cellulose, and further comprises tribasic calcium phosphate.

18. A method, comprising intranasally administering to a subject the intranasal pharmaceutical powder composition of claim 1.

19. The intranasal pharmaceutical powder composition of claim 11, wherein the intranasal pharmaceutical powder composition comprises:
1) about 1 to about 8 mg of the dihydroergotamine or a pharmaceutically acceptable salt thereof;
2) about 5 to about 15 mg of the mannitol;
3) about 5 to about 15 mg of the microcrystalline cellulose; and
4) the thickening agent that is hydroxypropyl methyl cellulose (HPMC).

20. The intranasal pharmaceutical powder composition of claim 12, wherein the intranasal pharmaceutical powder composition comprises:
1) the dihydroergotamine or a pharmaceutically acceptable salt thereof that is present in about 1% to about 30% of a total weight of the intranasal pharmaceutical powder composition;
2) the mannitol that is present in about 15% to about 55% of the total weight of the intranasal pharmaceutical powder composition;
3) the microcrystalline cellulose that is present in about 40% to about 75% of the total weight of the intranasal pharmaceutical powder composition, and
4) the hydroxypropyl methylcellulose (HPMC) that is present in about 0.05% to about 5% of the total weight of the intranasal pharmaceutical powder composition.

* * * * *